US008715326B2

(12) United States Patent
Champagne et al.

(10) Patent No.: US 8,715,326 B2
(45) Date of Patent: May 6, 2014

(54) DISTAL INTERPHALANGEAL FUSION DEVICE AND METHOD OF USE

(75) Inventors: Lloyd Champagne, Paradise Valley, AZ (US); Bruce King, Tucson, AZ (US); Omar Contento, Hillsboro, OR (US); Mike Lanham, Tucson, AZ (US); Donald J. Martin, Tucson, AZ (US)

(73) Assignee: Competitive Global Medical, LLC, Tucson, AZ (US)

( * ) Notice: Subject to any disclaimer, the term of this patent is extended or adjusted under 35 U.S.C. 154(b) by 663 days.

(21) Appl. No.: 12/869,675

(22) Filed: Aug. 26, 2010

(65) Prior Publication Data

US 2011/0054545 A1    Mar. 3, 2011

Related U.S. Application Data

(60) Provisional application No. 61/238,098, filed on Aug. 28, 2009.

(51) Int. Cl.
*A61B 17/86* (2006.01)

(52) U.S. Cl.
USPC ........... 606/320; 606/304; 606/315; 606/328; 606/104; 606/916

(58) Field of Classification Search
USPC ......... 606/300–321, 323, 326, 328, 104, 916; 623/17.14, 19.12, 20.22, 21.13, 21.16, 623/23.4; 411/383, 384, 388, 389, 412, 411/424; 403/90
See application file for complete search history.

(56) References Cited

U.S. PATENT DOCUMENTS 2,390,461 A    12/1945    Racz
(Continued)

FOREIGN PATENT DOCUMENTS

EP    1 632 200    3/2006    ............... A61F 2/42
(Continued)

OTHER PUBLICATIONS

International Search Report and Written Opinion of the International Searching Authority issued in related PCT application PCT/US2011/028646 dated May 3, 2011 (12 pgs).

(Continued)

*Primary Examiner* — Michael T Schaper
(74) *Attorney, Agent, or Firm* — Hayes Soloway P.C.

(57) ABSTRACT

Embodiments of the invention are directed to a distal interphalangeal ("DIP") fusion device for connecting a first bone of a patient to a second, adjacent bone of the patient. The device may include an anchor assembly and a compressor assembly. In another embodiment, a separate compressor base assembly is included. In yet another embodiment an access port assembly is included. The anchor assembly is rotationally coupled to one end of the compressor assembly, such that the compressor assembly may rotate about the anchor assembly within a semi-spherical zone (three degrees of rotational freedom) and translate axially (one degree of translational freedom). In an operative position, the anchor assembly is anchored in an intermediate phalanx of a digit of a patient, the compressor assembly is contained in a distal phalanx of the digit, and the distal phalanx is flexed relative to the intermediate phalanx to create a joint angle. The joint angle is then fixated for fusion by compressing the phalanges together in the flexed position by counter-rotation of the compressor assembly. An advantage of an embodiment of the invention is the screw threads may be matching which eliminates the need to pre-drill two different diameter pilot holes.

7 Claims, 47 Drawing Sheets

(56) References Cited

U.S. PATENT DOCUMENTS

| | | | |
|---|---|---|---|
| 4,119,092 A | 10/1978 | Gil | 128/92 D |
| 4,304,011 A | 12/1981 | Whelan, III | 3/1.91 |
| 4,352,212 A | 10/1982 | Greene et al. | 3/1.91 |
| 4,759,768 A | 7/1988 | Hermann et al. | 623/21 |
| 4,760,843 A | 8/1988 | Fischer et al. | 606/304 |
| 4,946,455 A | 8/1990 | Rosen | 604/403 |
| 5,011,497 A | 4/1991 | Persson et al. | 623/21 |
| 5,074,882 A | 12/1991 | Grammont et al. | |
| 5,129,903 A | 7/1992 | Luhr et al. | 606/71 |
| 5,147,386 A | 9/1992 | Carignan et al. | 623/21 |
| 5,251,520 A | 10/1993 | Lanham | |
| 5,334,184 A | 8/1994 | Bimman | |
| 5,405,401 A | 4/1995 | Lippincott, III et al. | 623/21 |
| 5,417,692 A | 5/1995 | Goble et al. | 606/73 |
| 5,522,903 A | 6/1996 | Sokolow et al. | 623/21 |
| 5,569,247 A | 10/1996 | Morrison | 606/61 |
| 5,591,166 A | 1/1997 | Bernhardt et al. | 606/61 |
| 5,628,740 A | 5/1997 | Mullane | 606/61 |
| 5,667,510 A | 9/1997 | Combs | |
| 5,683,466 A | 11/1997 | Vitale | 623/18 |
| 5,713,897 A | 2/1998 | Goble et al. | 606/53 |
| 5,827,285 A | 10/1998 | Bramlet | 606/60 |
| 5,984,970 A | 11/1999 | Bramlet | 623/21 |
| 6,284,001 B1 | 9/2001 | Knapp | 623/21.14 |
| 6,517,543 B1 | 2/2003 | Berrevoets et al. | 606/73 |
| 6,689,169 B2 | 2/2004 | Harris | 623/21.16 |
| 6,733,502 B2 | 5/2004 | Altarac et al. | 606/61 |
| 6,767,351 B2 | 7/2004 | Orbay et al. | 606/69 |
| 6,780,186 B2 | 8/2004 | Errico et al. | 606/71 |
| 7,041,106 B1 | 5/2006 | Carver et al. | 606/72 |
| 7,608,096 B2 | 10/2009 | Foley et al. | 606/280 |
| 7,717,958 B2 | 5/2010 | Cragg et al. | 623/17.12 |
| 7,740,648 B2 | 6/2010 | Young et al. | 606/286 |
| 8,048,134 B2 | 11/2011 | Partin | 606/320 |
| 2002/0198527 A1 | 12/2002 | Muckter | 606/73 |
| 2004/0172031 A1 | 9/2004 | Rubecamp et al. | 606/73 |
| 2005/0055023 A1 | 3/2005 | Sohngen et al. | |
| 2005/0216008 A1 | 9/2005 | Zwirnmann et al. | 606/69 |
| 2006/0149264 A1* | 7/2006 | Castaneda et al. | 606/73 |
| 2006/0235414 A1 | 10/2006 | Lim et al. | 606/73 |
| 2006/0271054 A1 | 11/2006 | Sucec et al. | 606/73 |
| 2007/0027230 A1 | 2/2007 | Beyar et al. | 523/117 |
| 2007/0055236 A1 | 3/2007 | Hudgins et al. | 606/61 |
| 2007/0096005 A1* | 5/2007 | March et al. | 248/549 |
| 2007/0185584 A1 | 8/2007 | Kaufmann et al. | 623/21.15 |
| 2007/0270855 A1 | 11/2007 | Partin | |
| 2007/0282342 A1 | 12/2007 | Niederberger et al. | 606/73 |
| 2008/0003054 A1* | 1/2008 | Fan | 403/122 |
| 2008/0065224 A1 | 3/2008 | Reigstad et al. | 623/18.11 |
| 2008/0140130 A1 | 6/2008 | Chan et al. | 606/280 |
| 2008/0195156 A1 | 8/2008 | Ainsworth et al. | 606/279 |
| 2008/0234678 A1 | 9/2008 | Gutierrez et al. | 606/60 |
| 2008/0300634 A1 | 12/2008 | Gray | 606/280 |
| 2009/0062868 A1 | 3/2009 | Casutt | 606/316 |
| 2009/0112269 A1 | 4/2009 | Lieberman et al. | 606/301 |
| 2009/0210016 A1 | 8/2009 | Champagne | 606/309 |
| 2009/0234359 A1 | 9/2009 | Onoue et al. | 606/71 |
| 2009/0248089 A1 | 10/2009 | Jacofsky et al. | 606/311 |
| 2009/0264934 A1 | 10/2009 | Youssef et al. | 606/280 |
| 2010/0004691 A1 | 1/2010 | Amato et al. | 606/280 |
| 2010/0036439 A1* | 2/2010 | Lavi | 606/308 |
| 2011/0004255 A1* | 1/2011 | Weiner et al. | 606/301 |
| 2011/0054545 A1 | 3/2011 | Champagne et al. | 606/301 |

FOREIGN PATENT DOCUMENTS

| | | | |
|---|---|---|---|
| FR | 2 651 119 | 8/1989 | A61F 2/42 |
| FR | 2 692 776 | 6/1992 | A61F 2/42 |
| WO | WO 95/33425 | 12/1995 | A61F 2/42 |
| WO | WO 97/22301 | 6/1997 | A61B 17/00 |
| WO | WO 02/30262 | 4/2002 | |
| WO | WO 2005/041793 | 5/2005 | A61F 2/44 |
| WO | WO 2010/026371 | 3/2010 | |
| WO | WO2010047688 | 4/2010 | A61B 17/58 |

OTHER PUBLICATIONS

International Search Report and Written Opinion issued in PCT Application Serial No. PCT/US10/46870 on Oct. 20, 2010, 12 pgs.

Office Action, U.S. Appl. No. 13/049,363 dated Oct. 16, 2012 (34 pgs).

International Search Report and the Written Opinion, dated Dec. 30, 2011 (10 pgs).

* cited by examiner

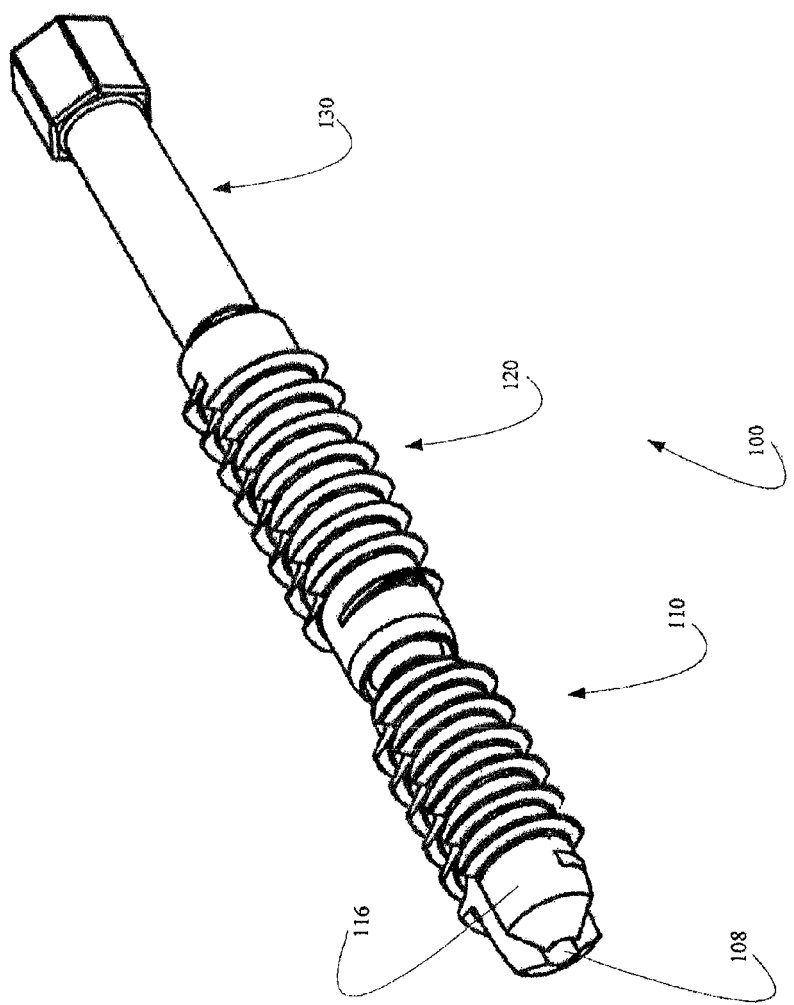

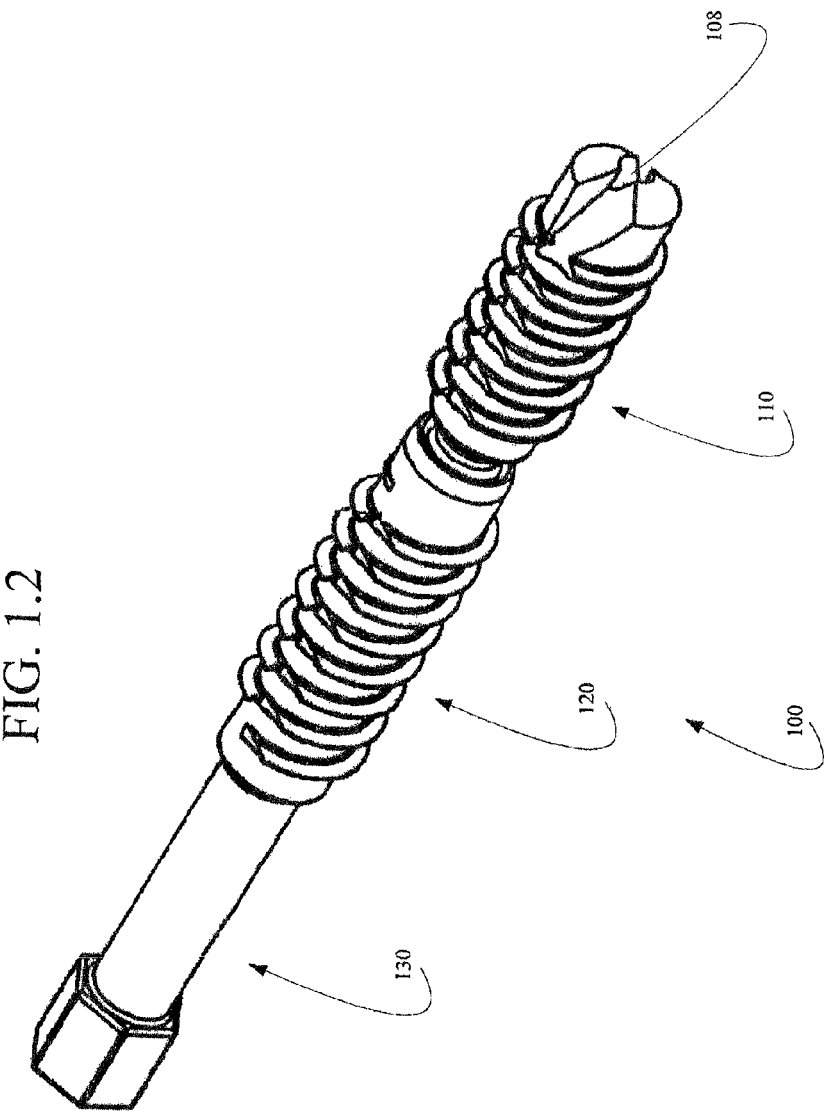
FIG. 1.2

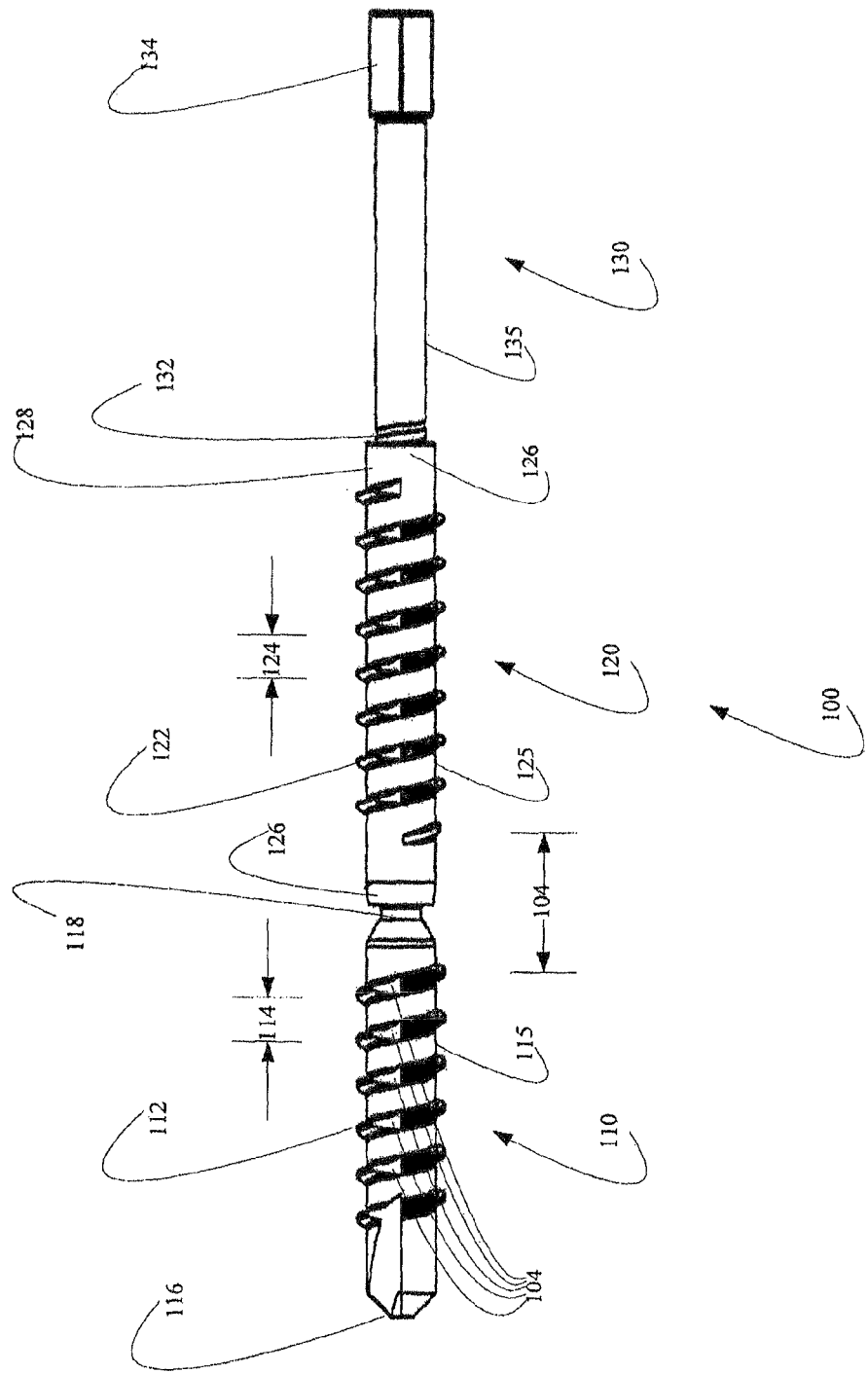
FIG. 1.3

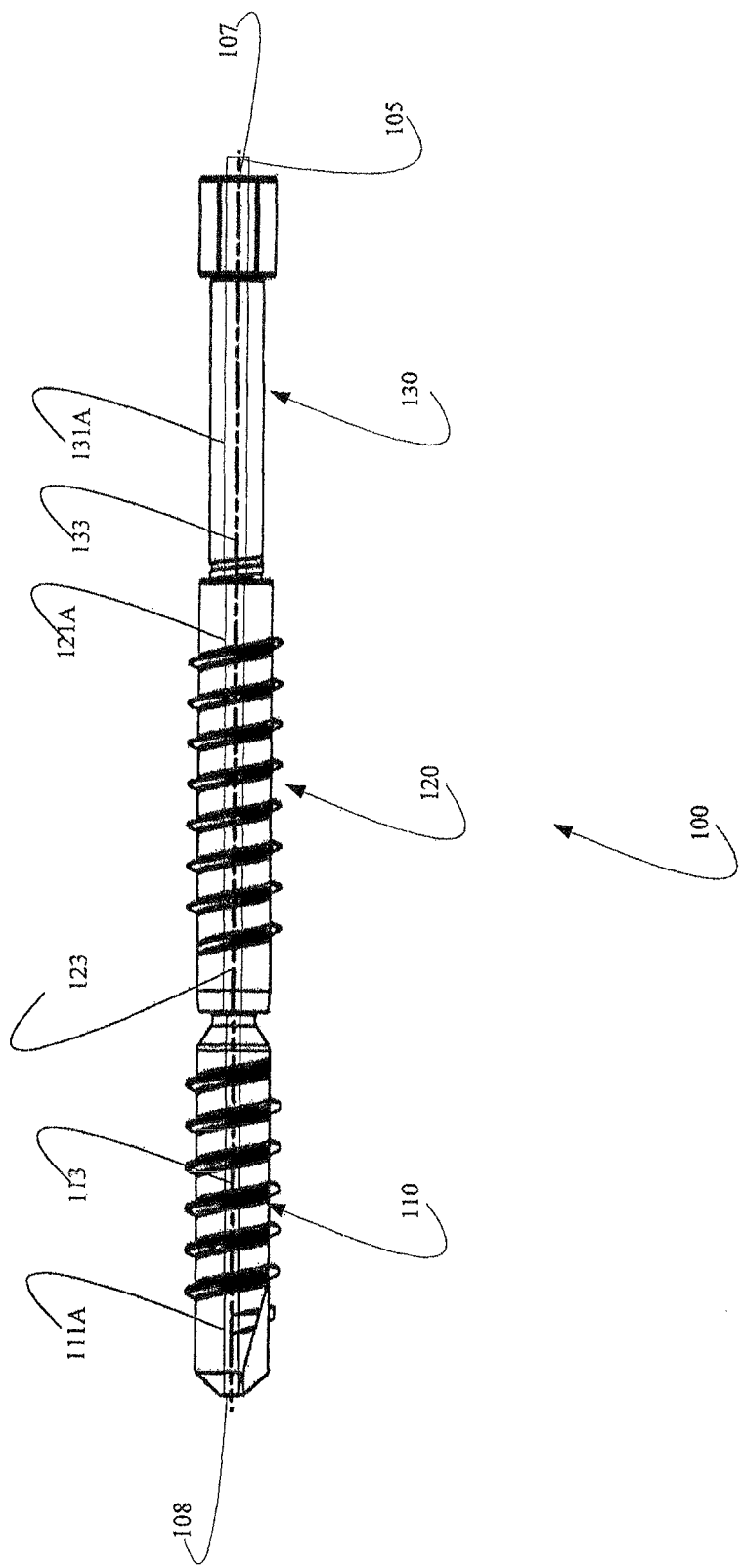
FIG. 1.4

FIG. 1.5
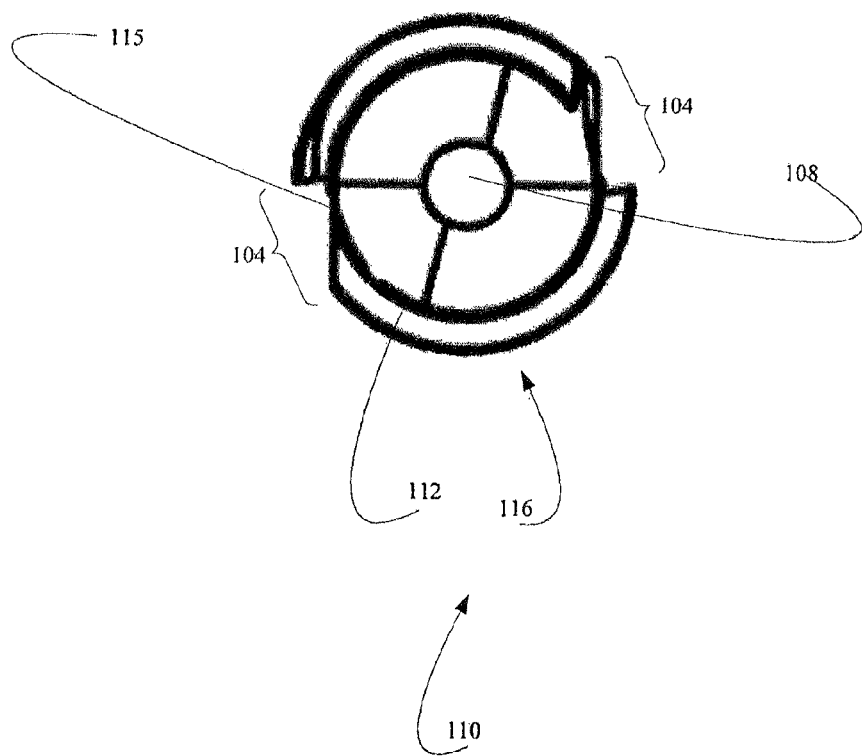

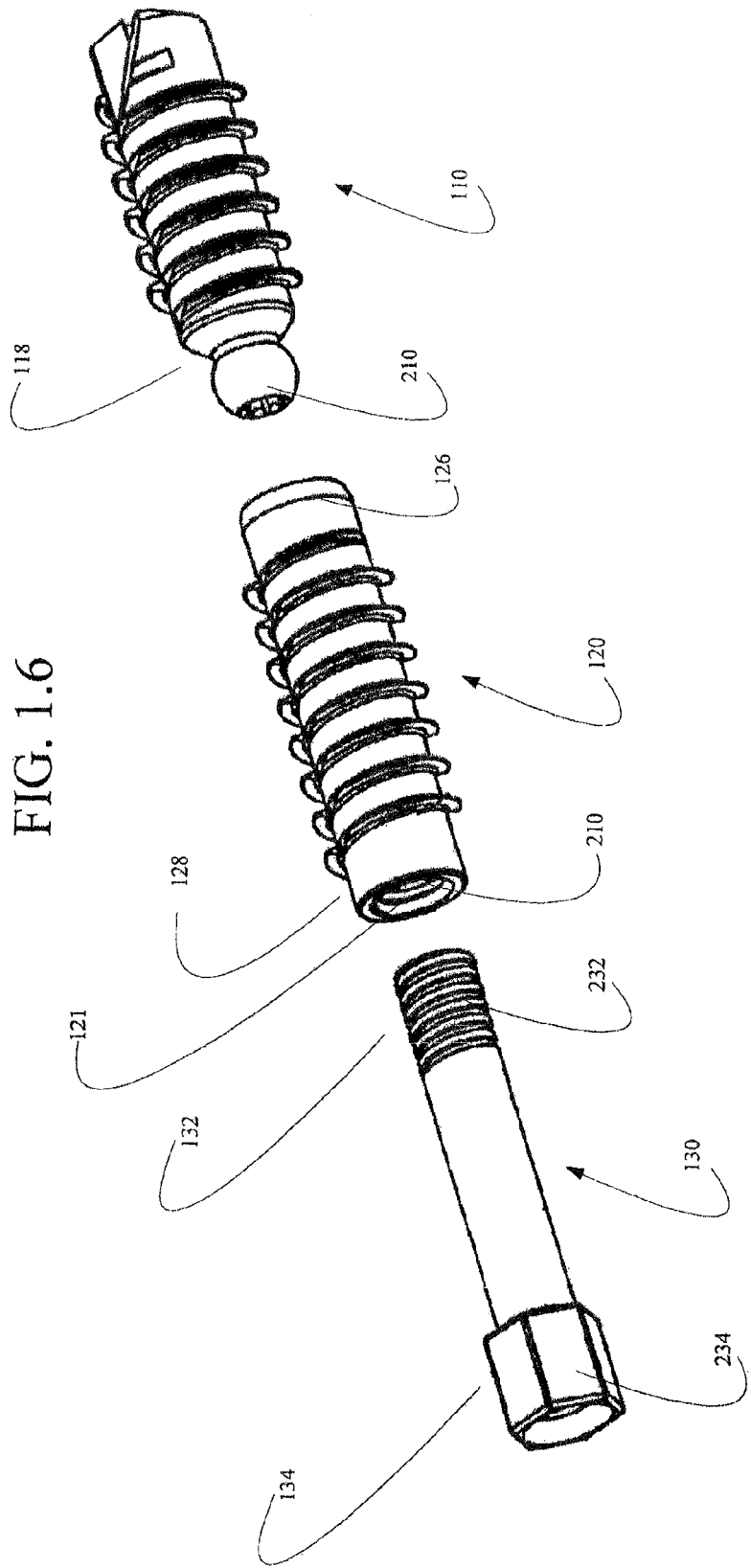
FIG. 1.6

FIG. 1.7
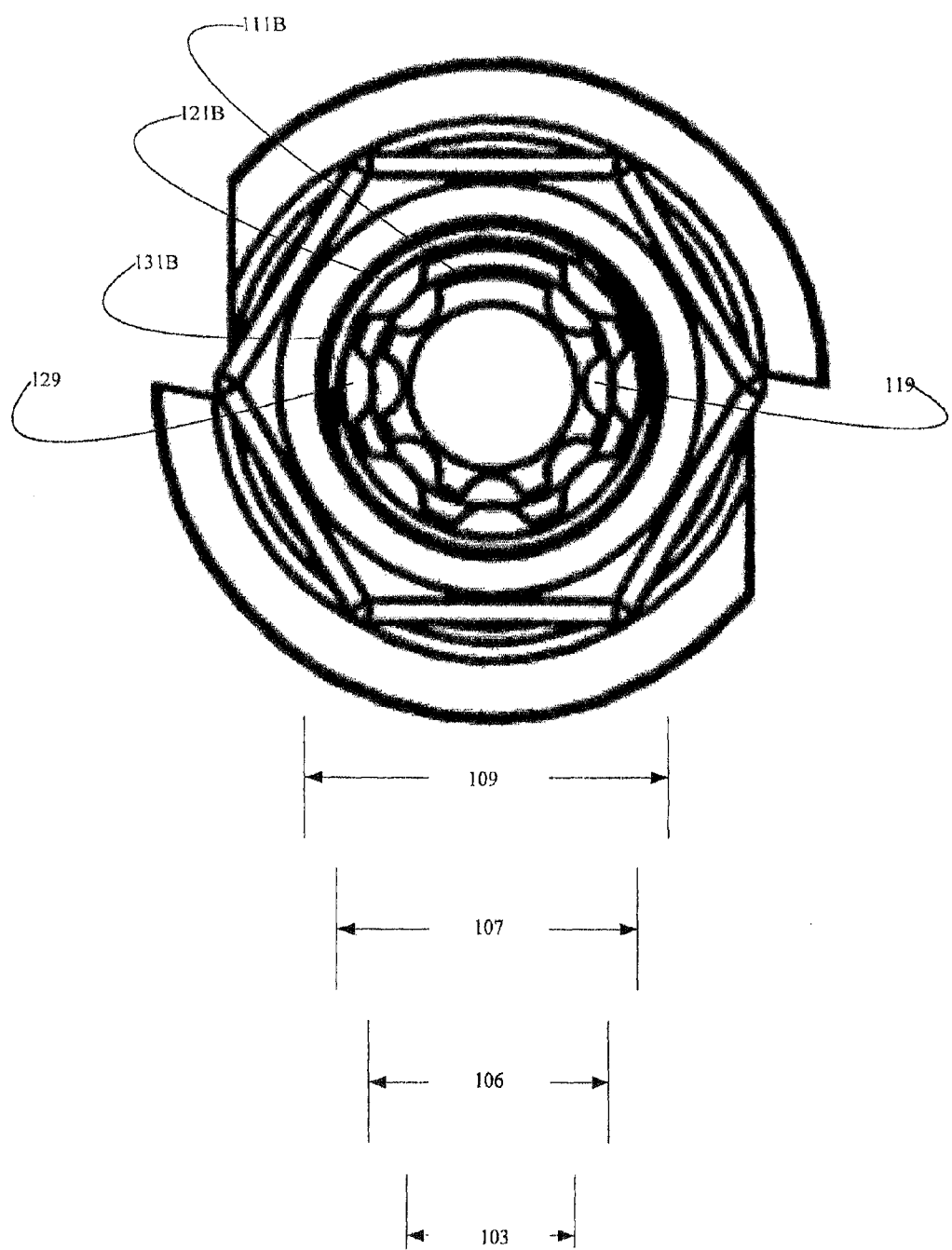

FIG. 1.8
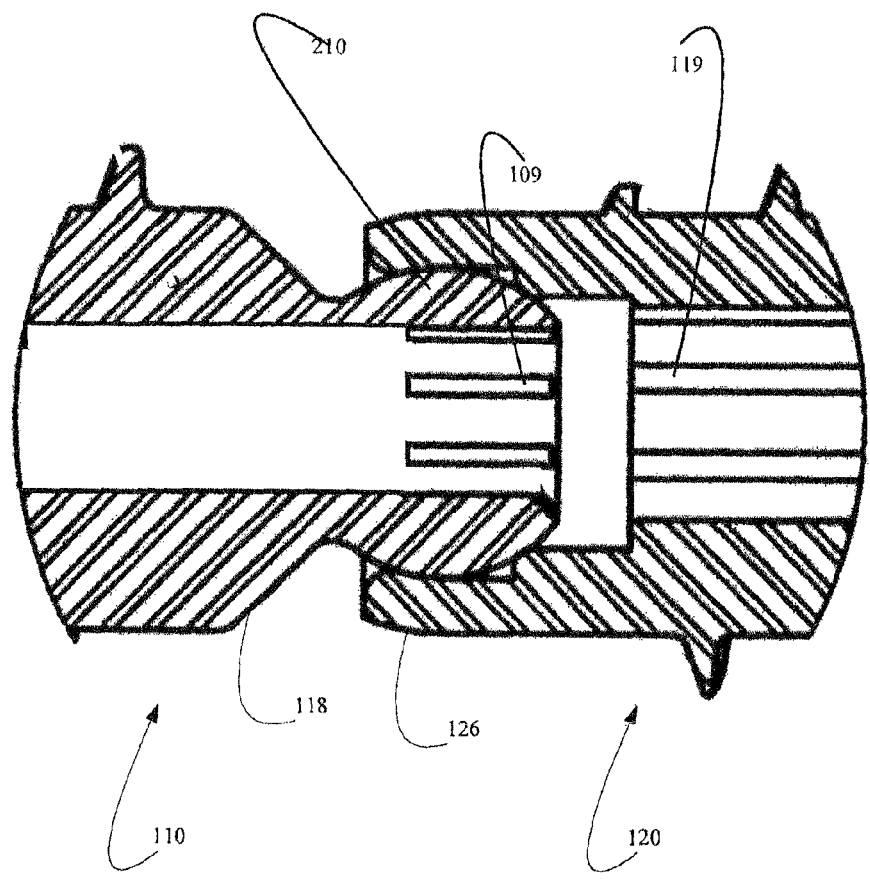

FIG. 1.9
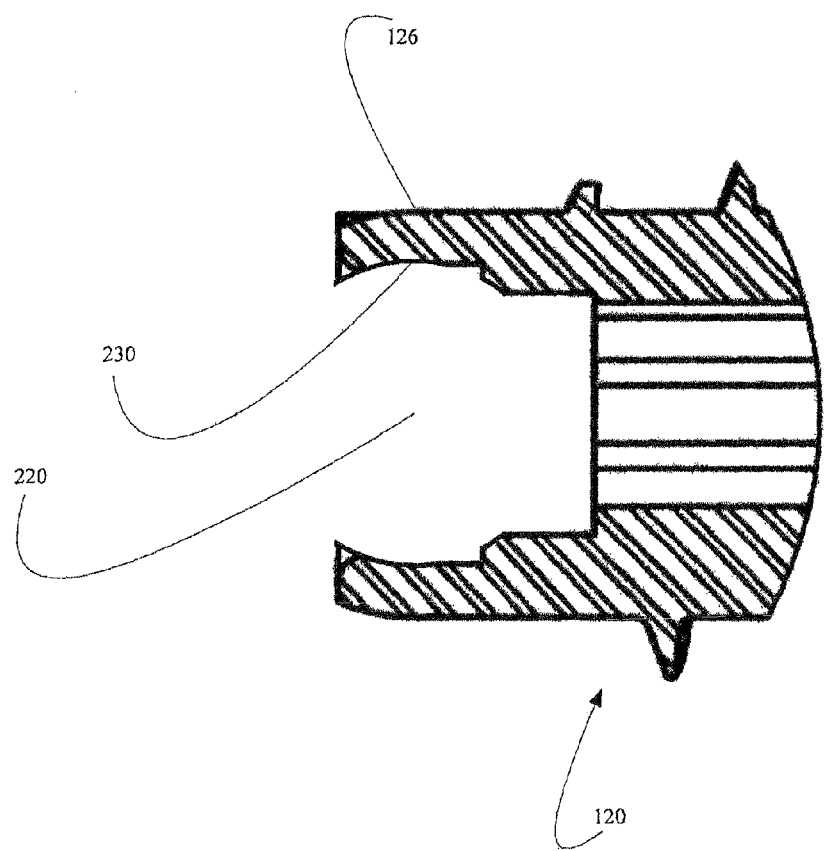

FIG. 1.10
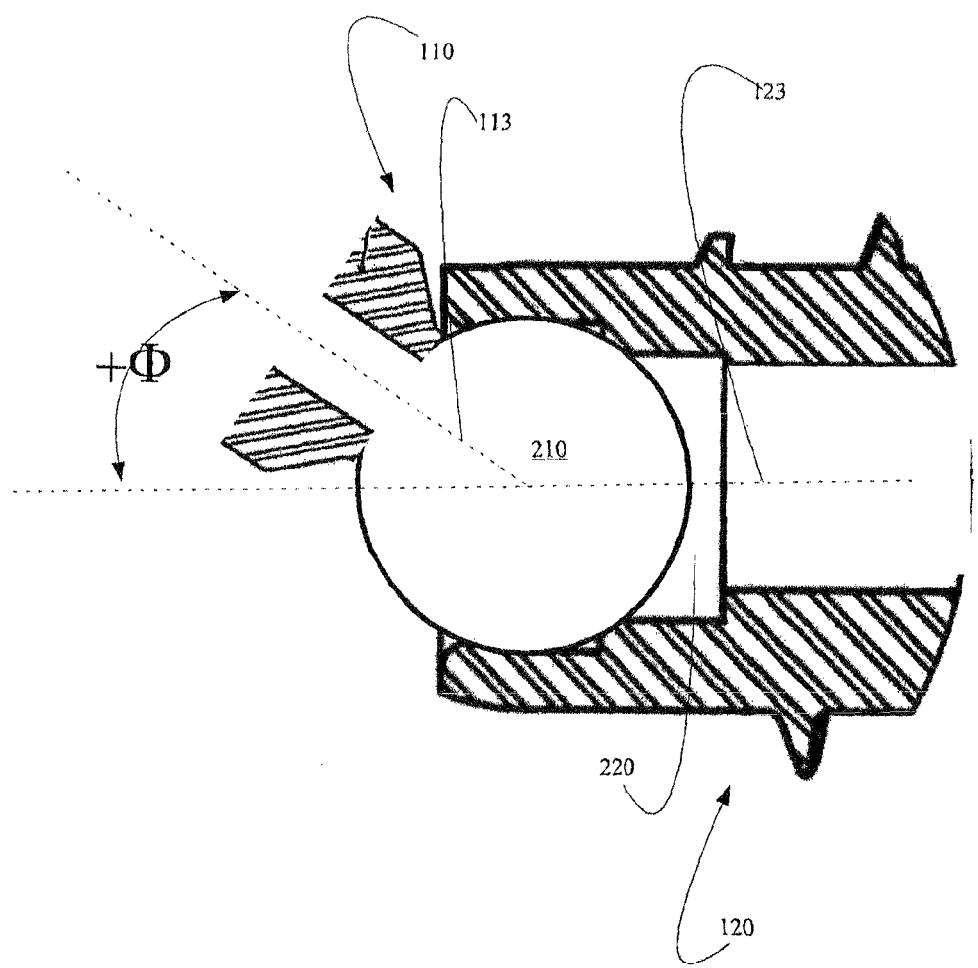

FIG. 1.11
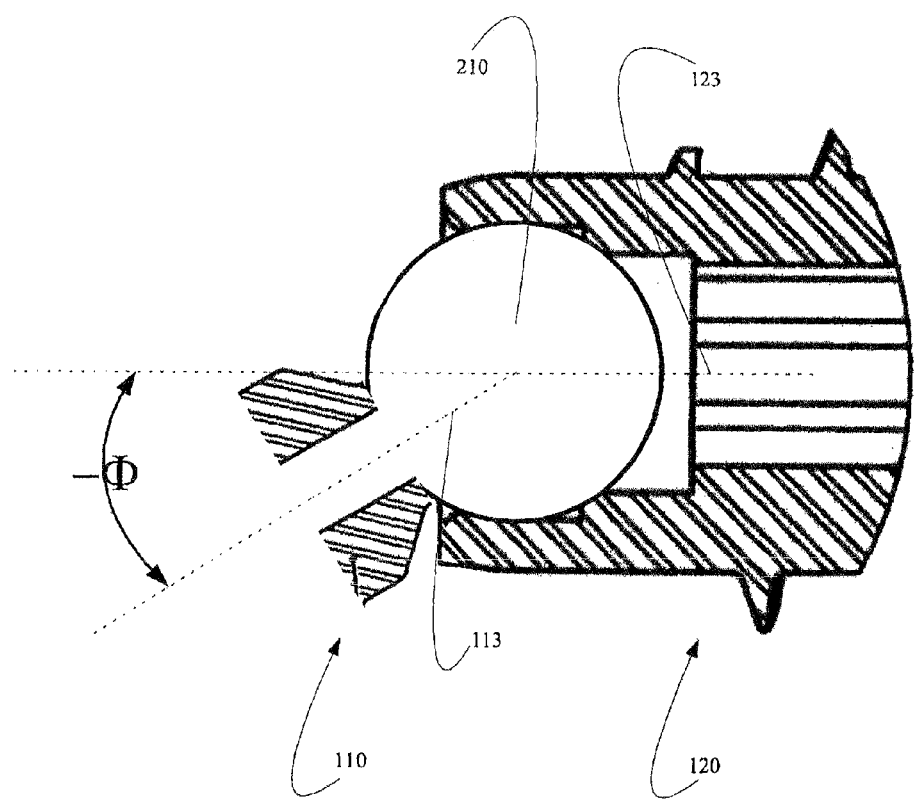

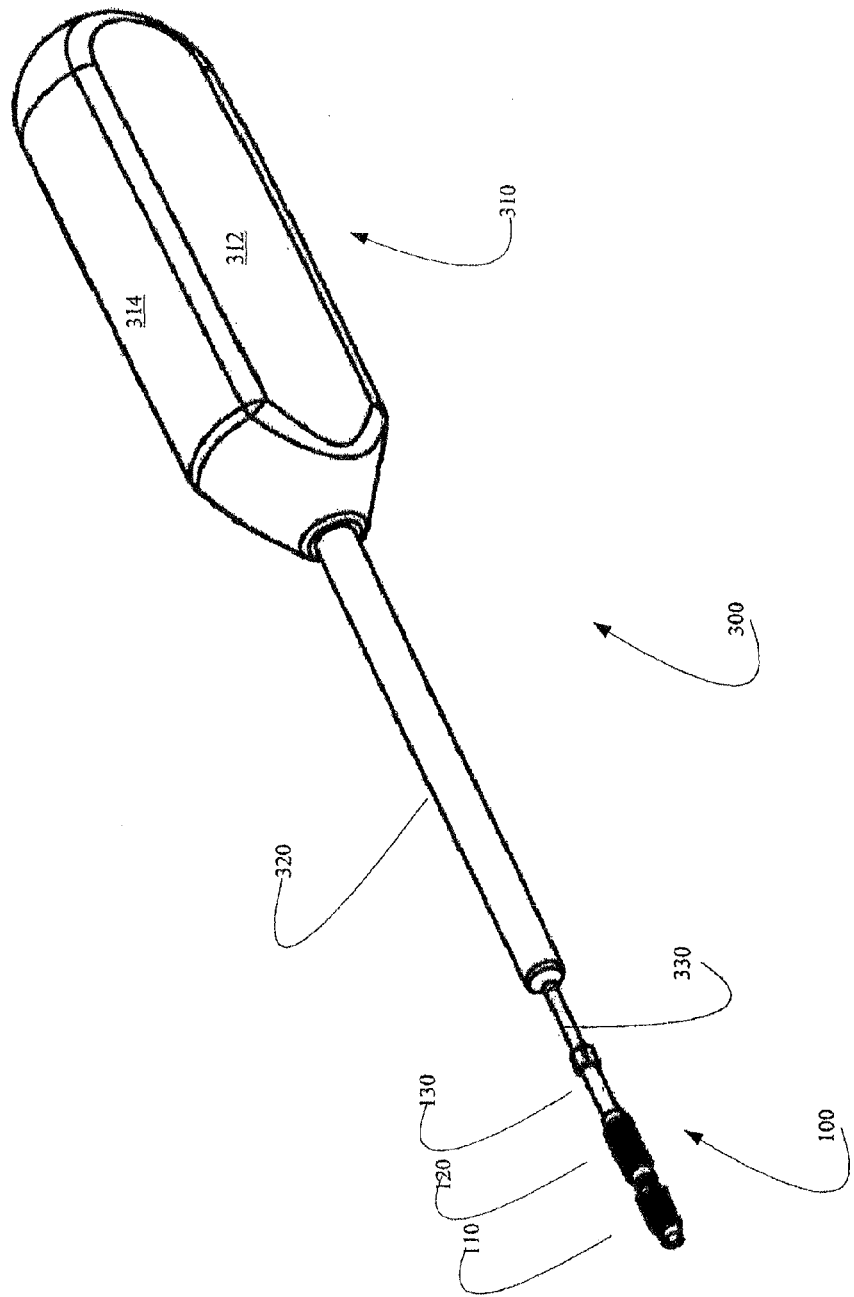
FIG. 2.1

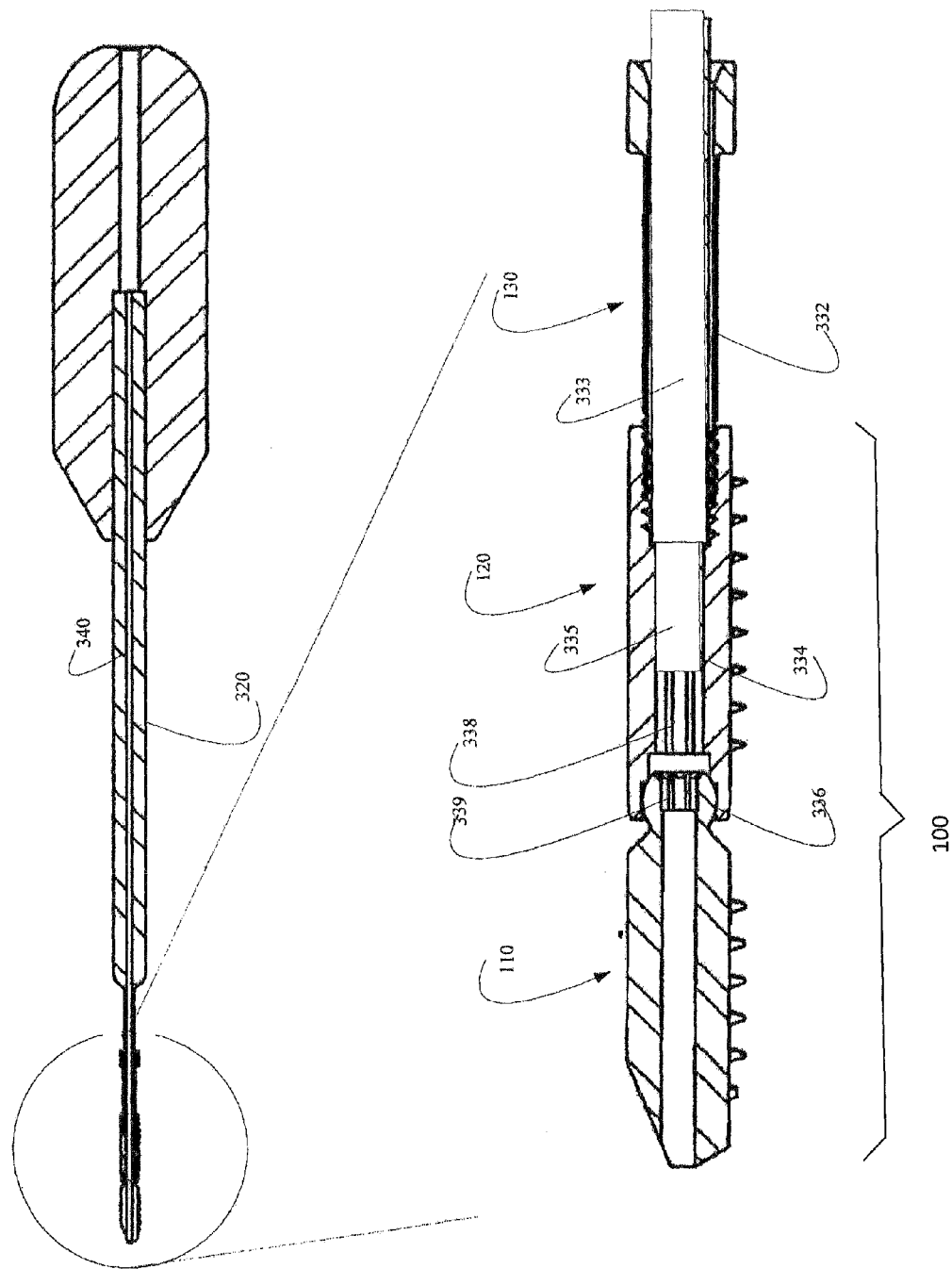

FIG. 2.3
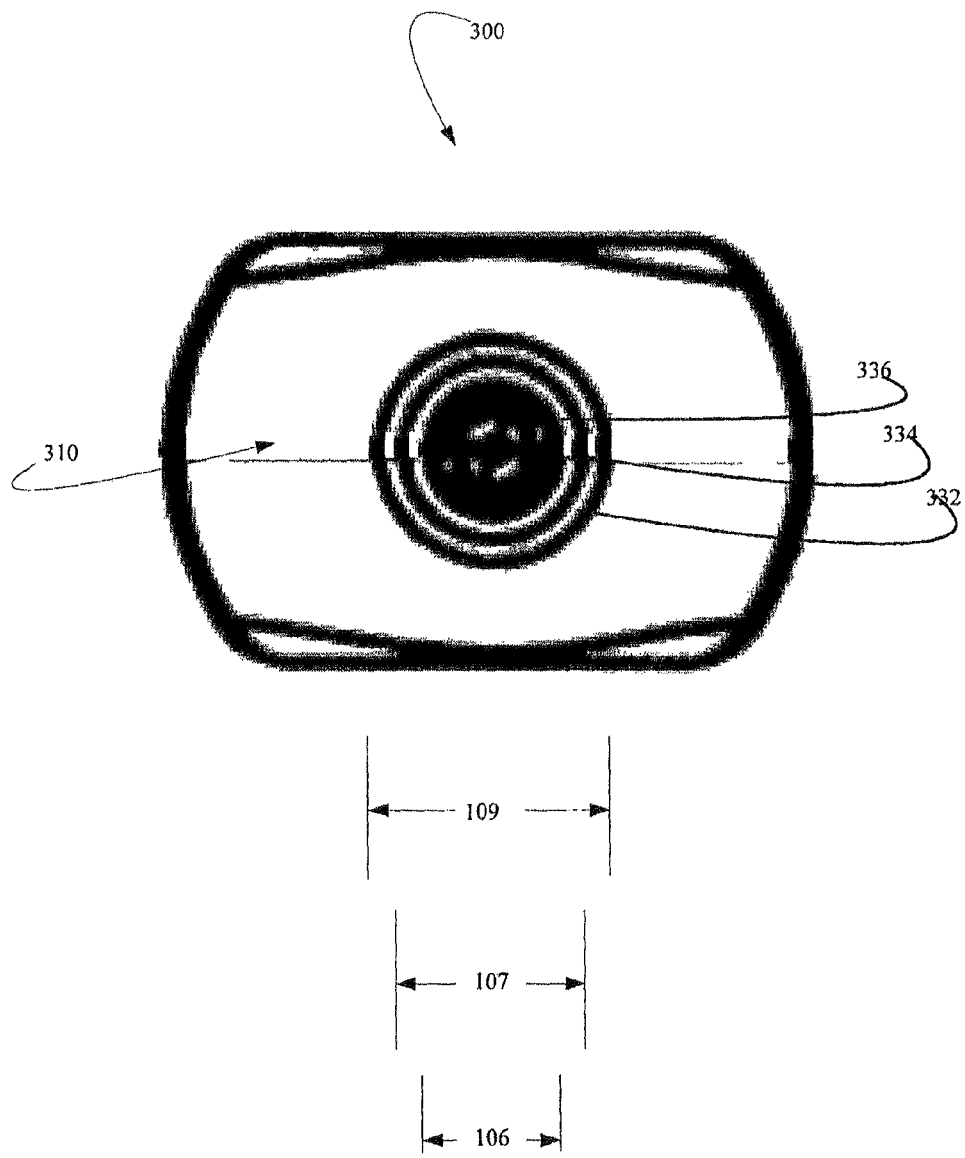

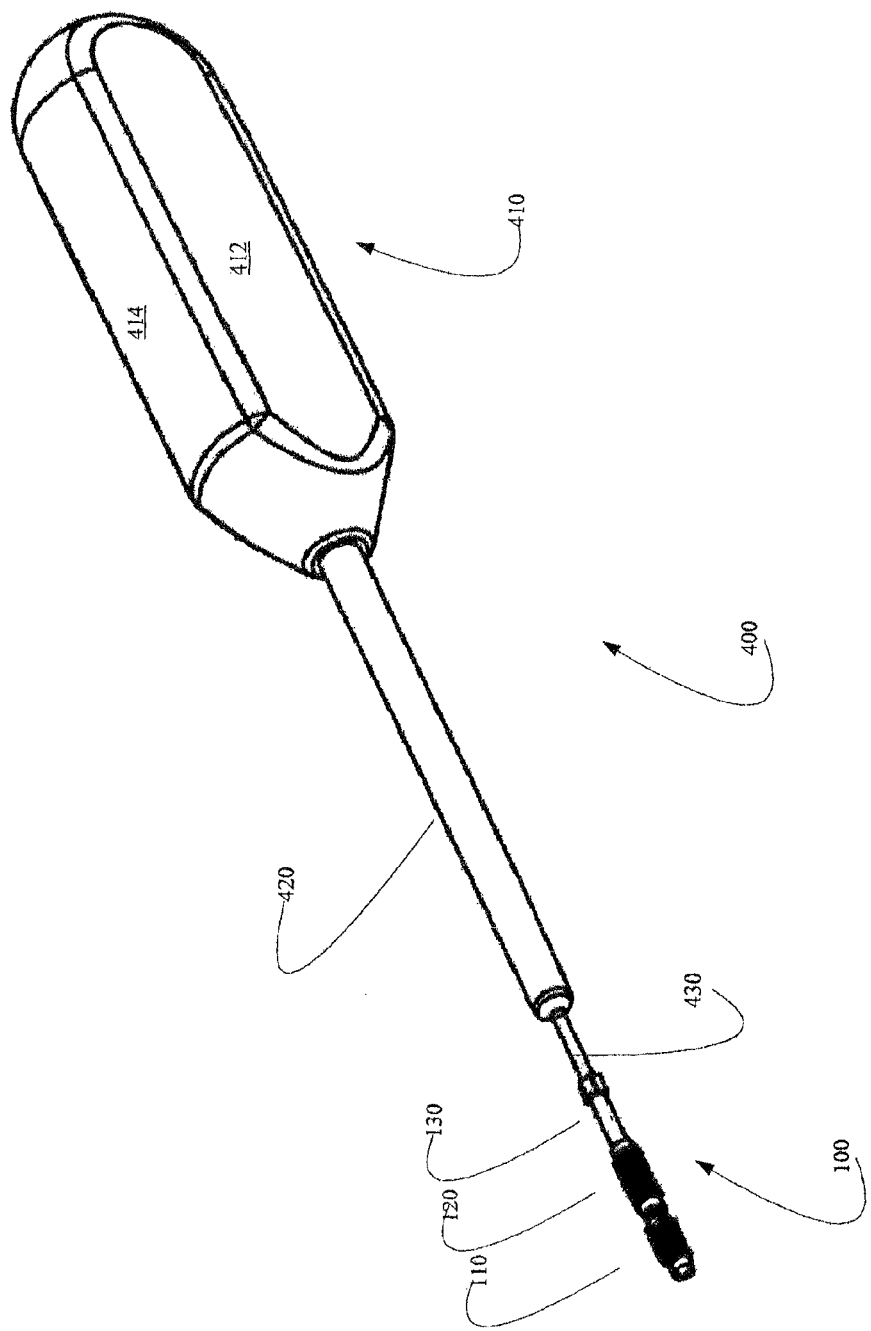
FIG. 3.1

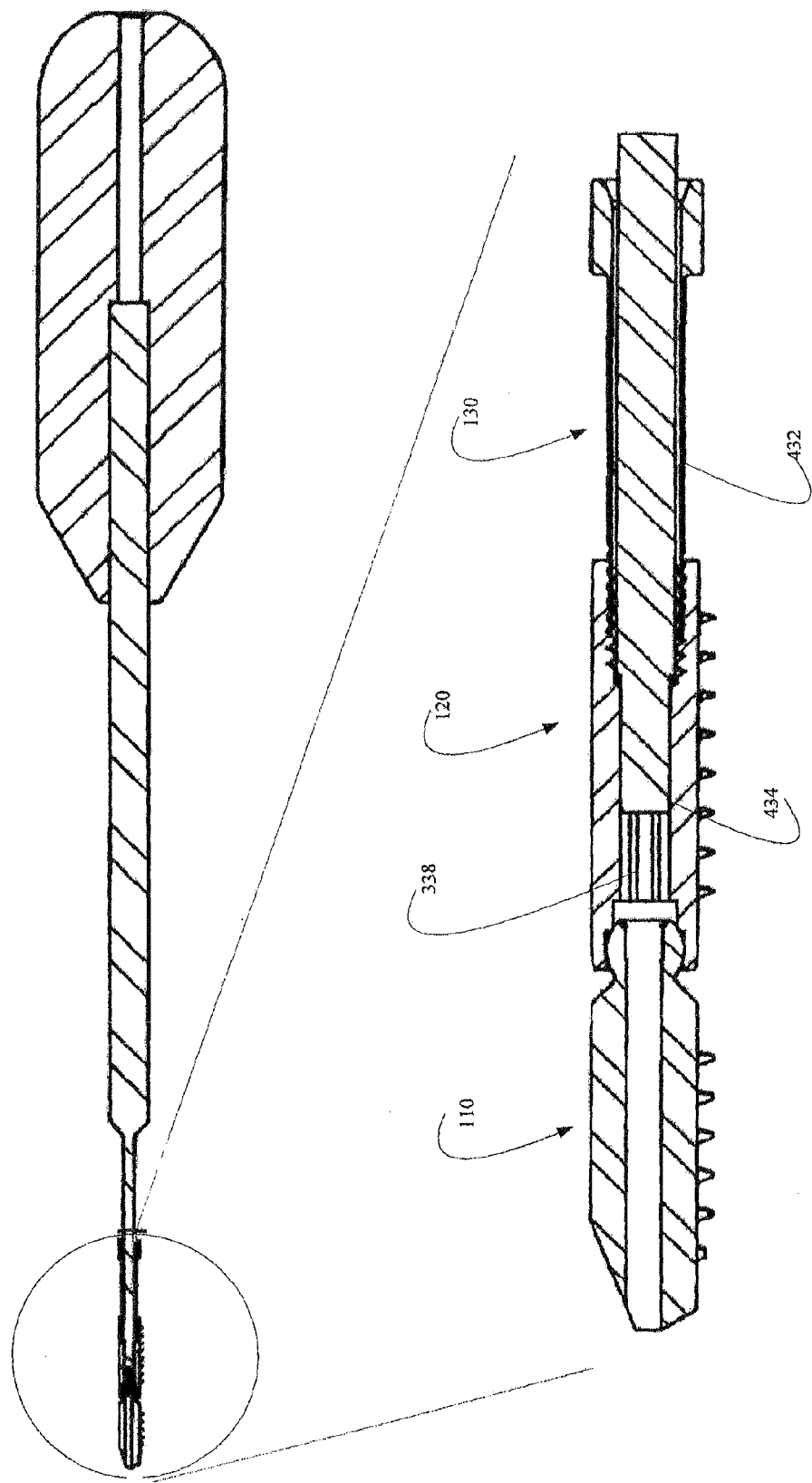
FIG. 3.2

FIG. 3.3
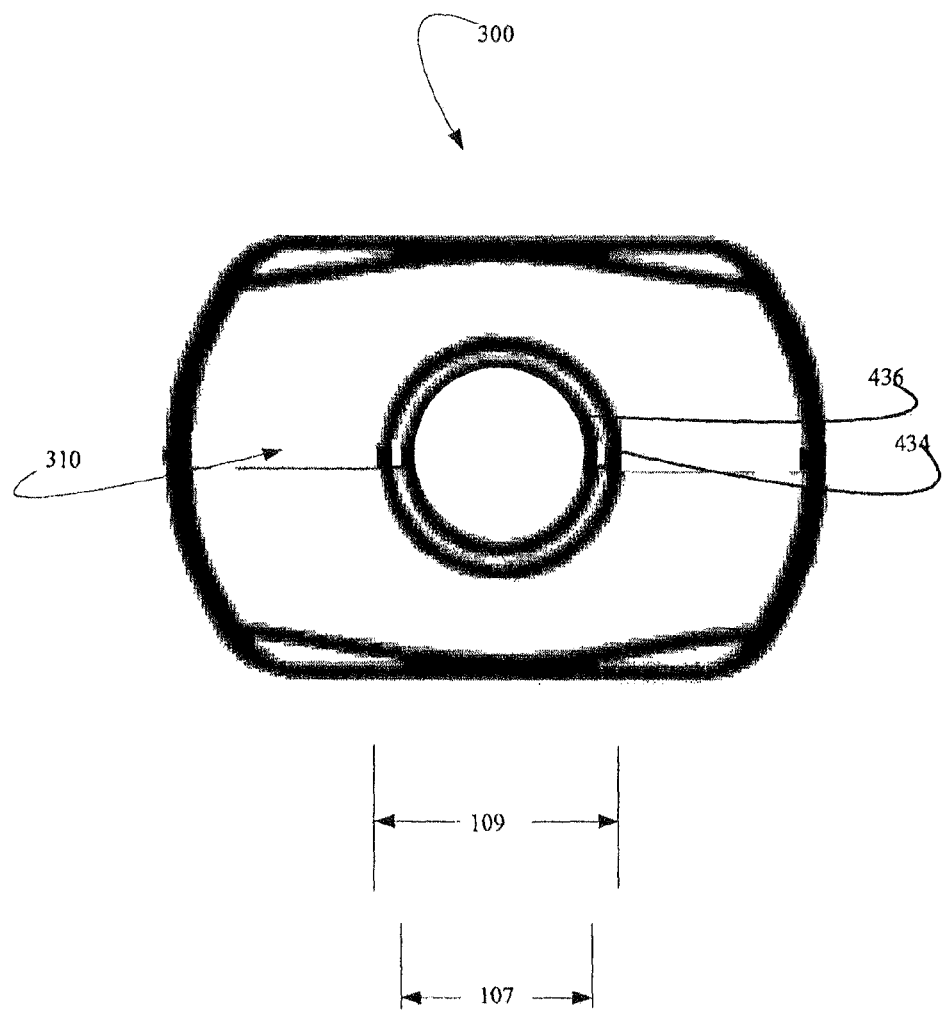

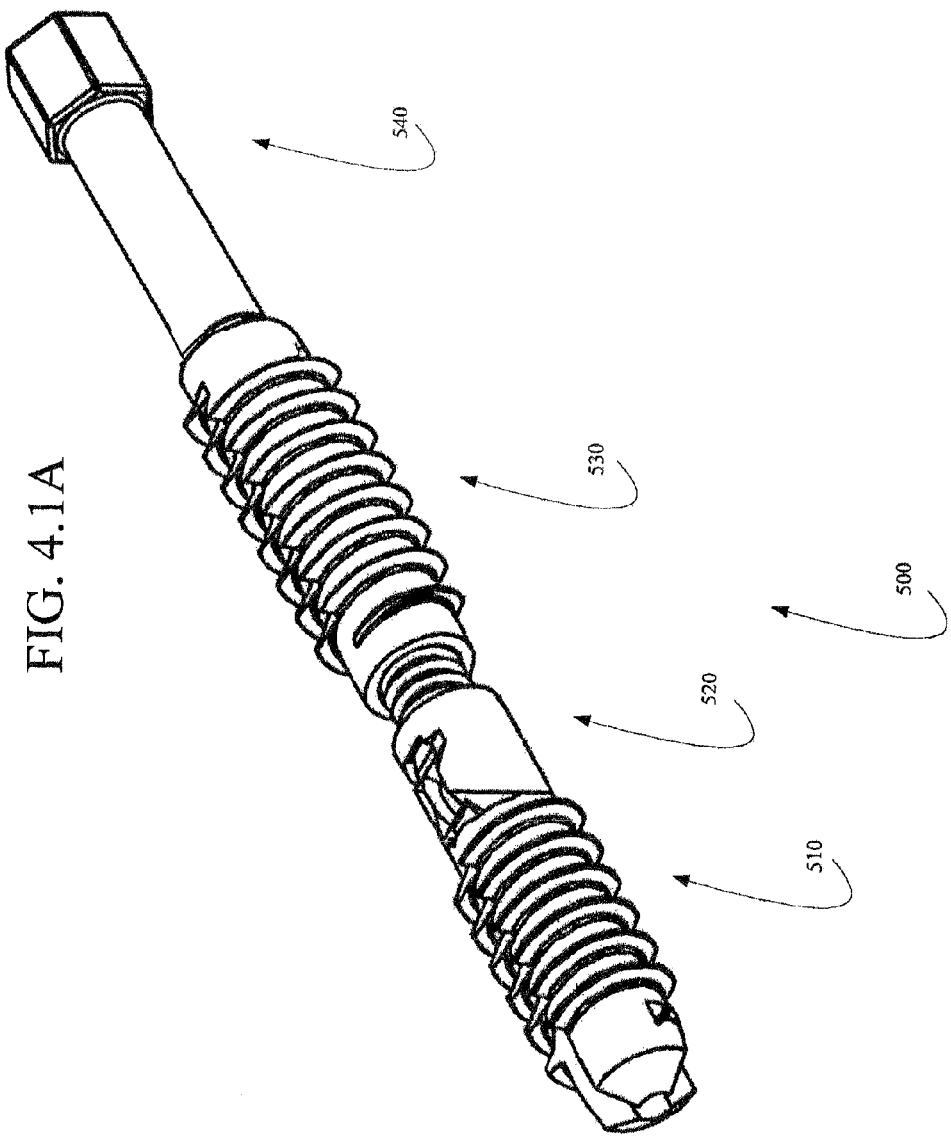
FIG. 4.1A

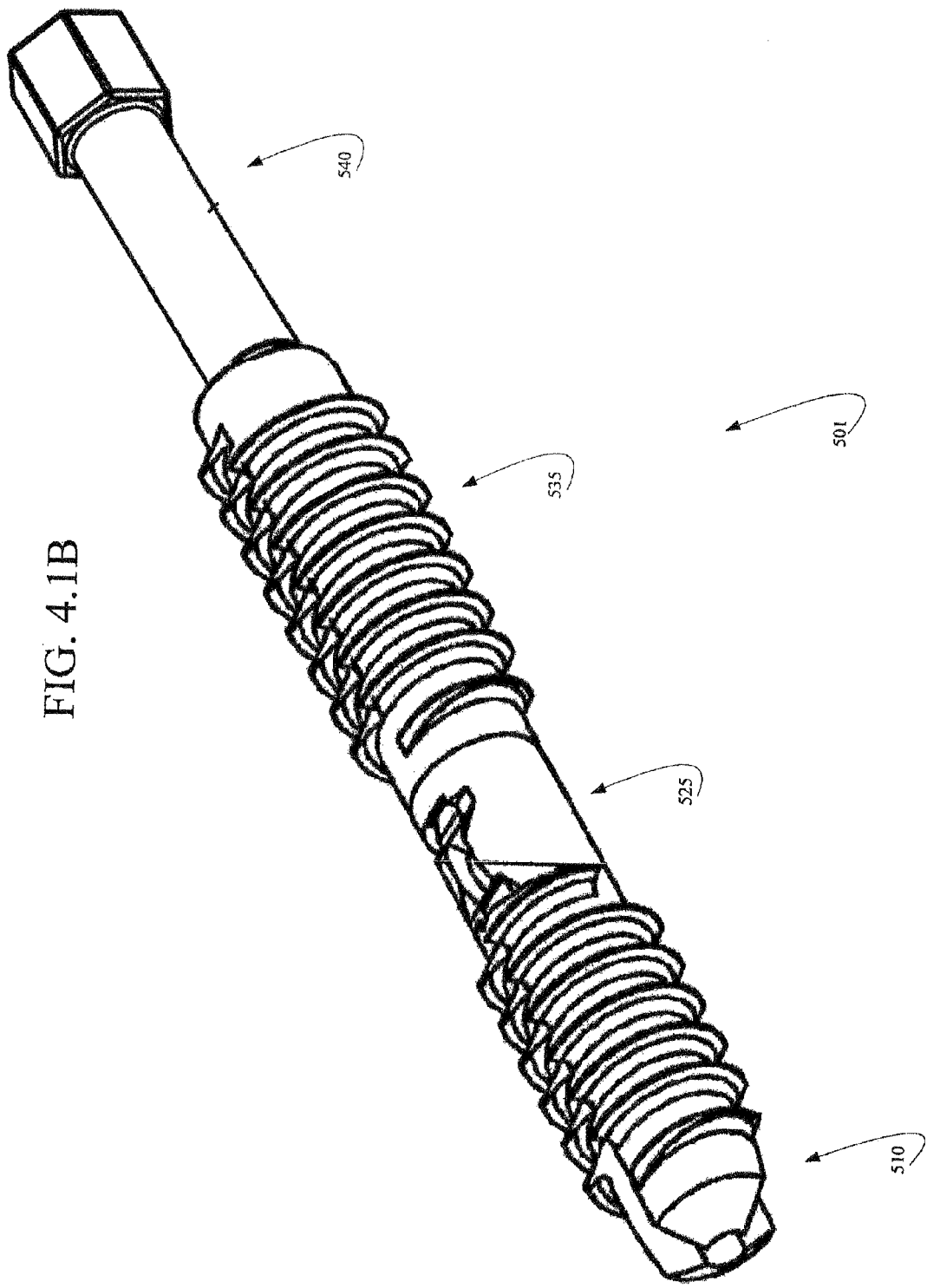
FIG. 4.1B

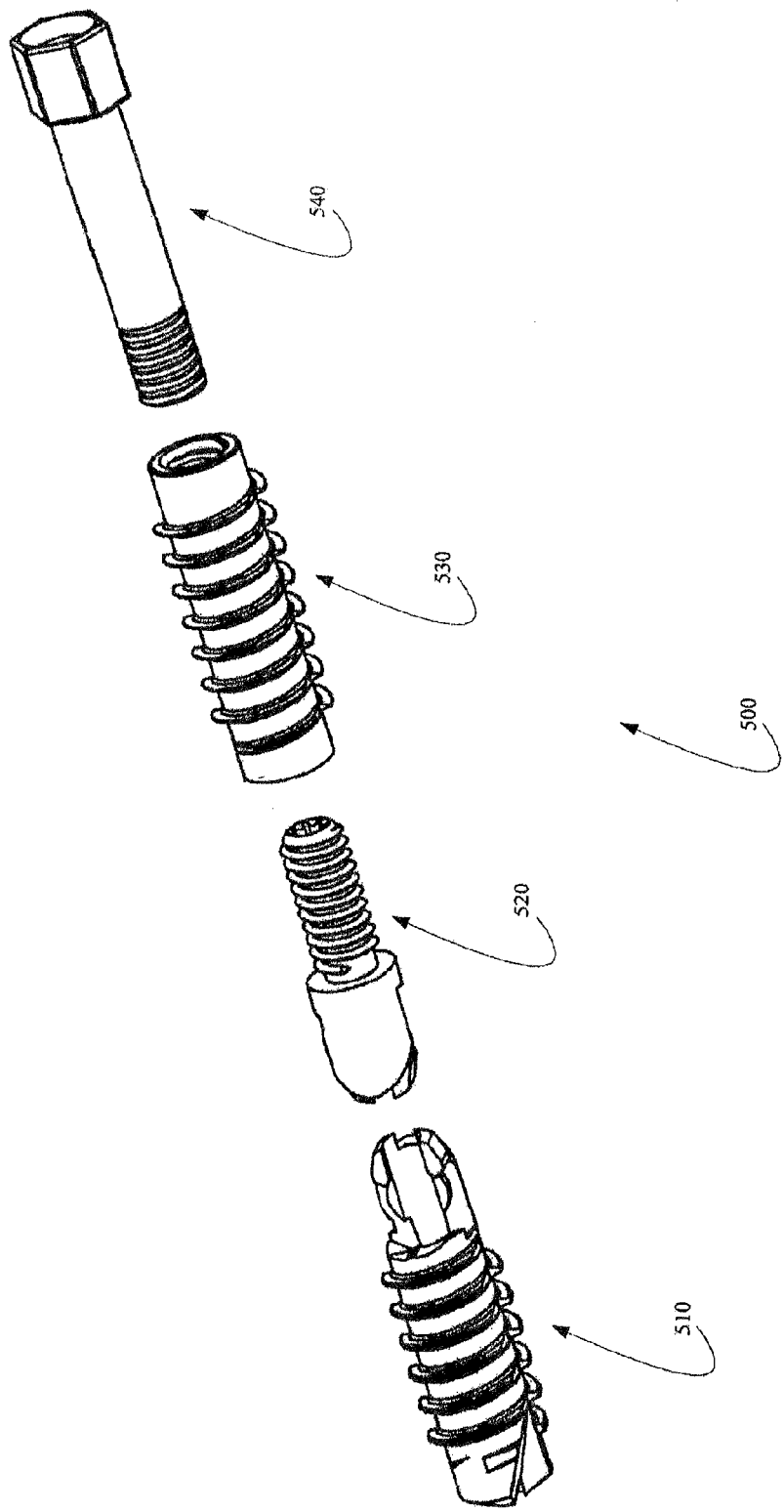
FIG. 4.2A

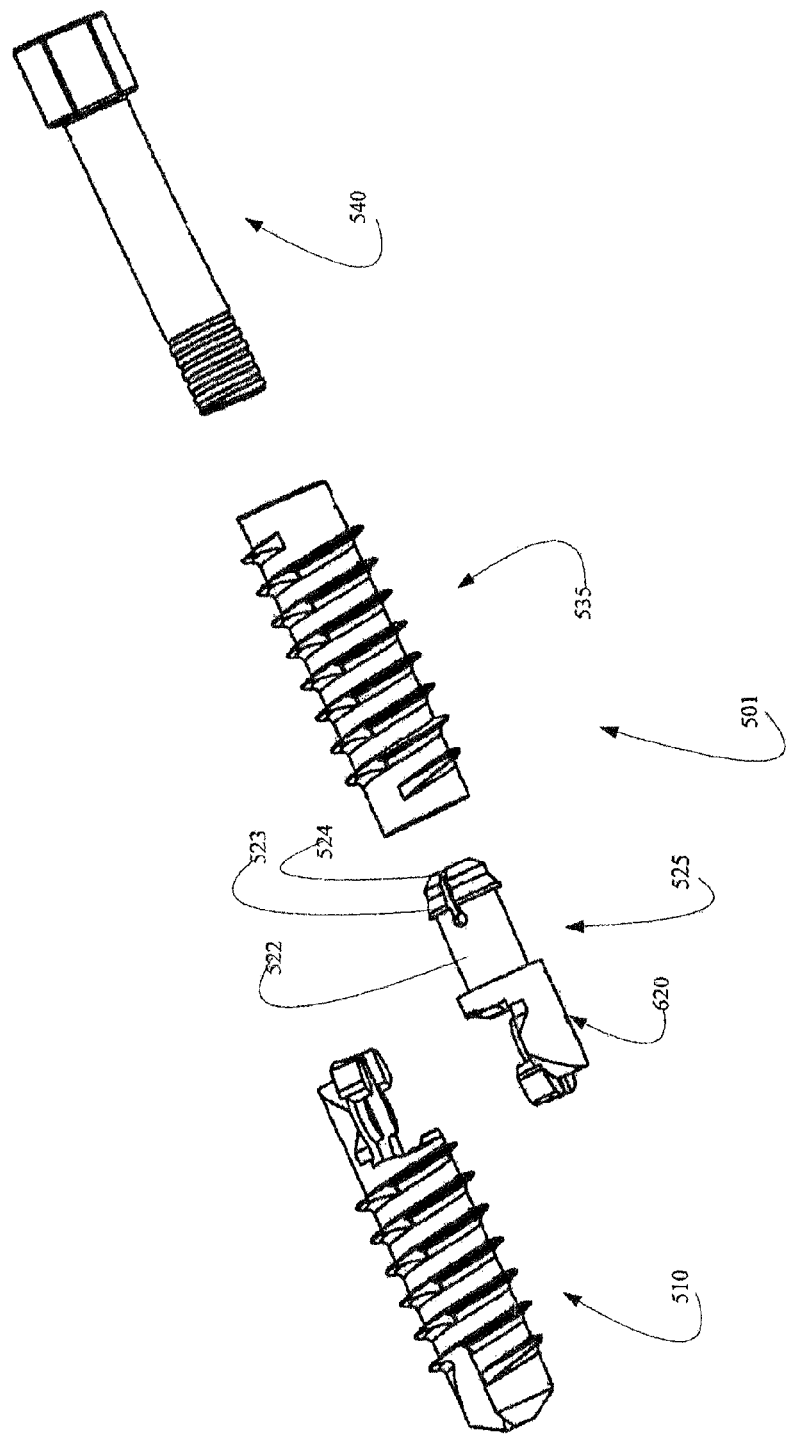
FIG. 4.2B

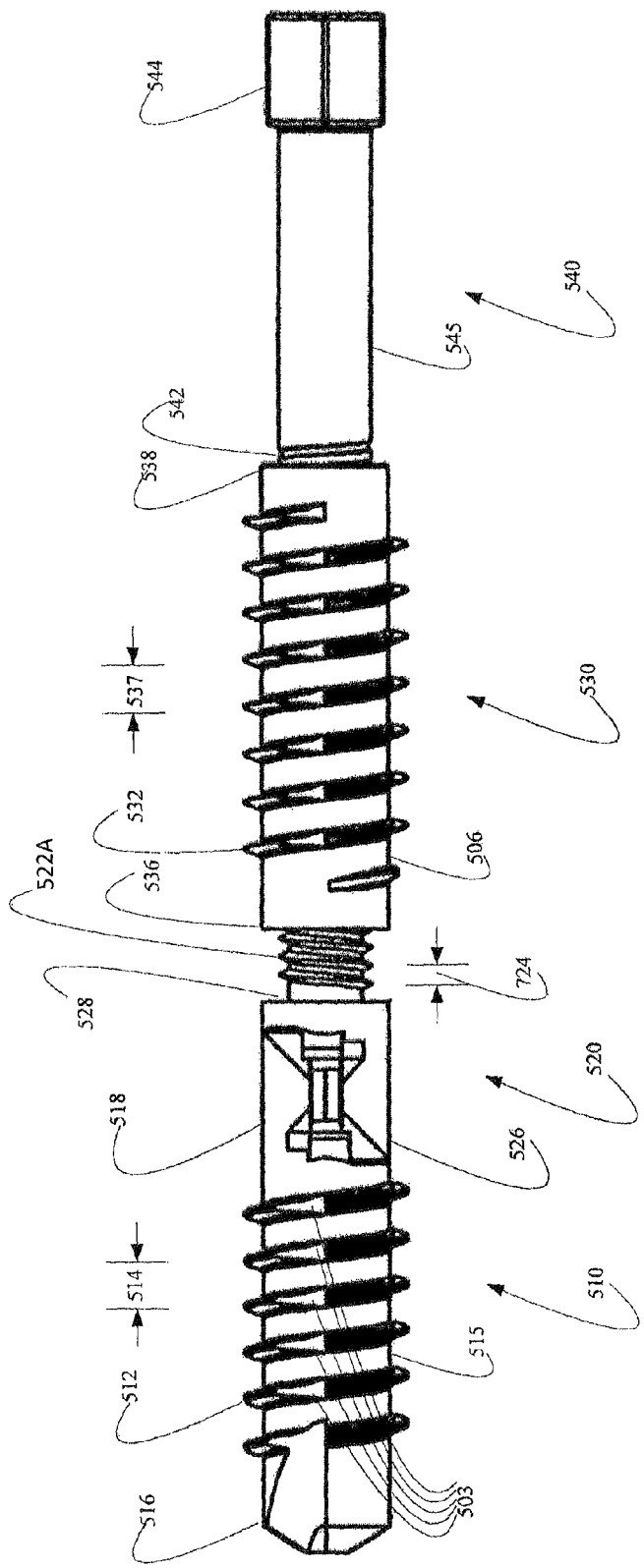
FIG. 4.3A

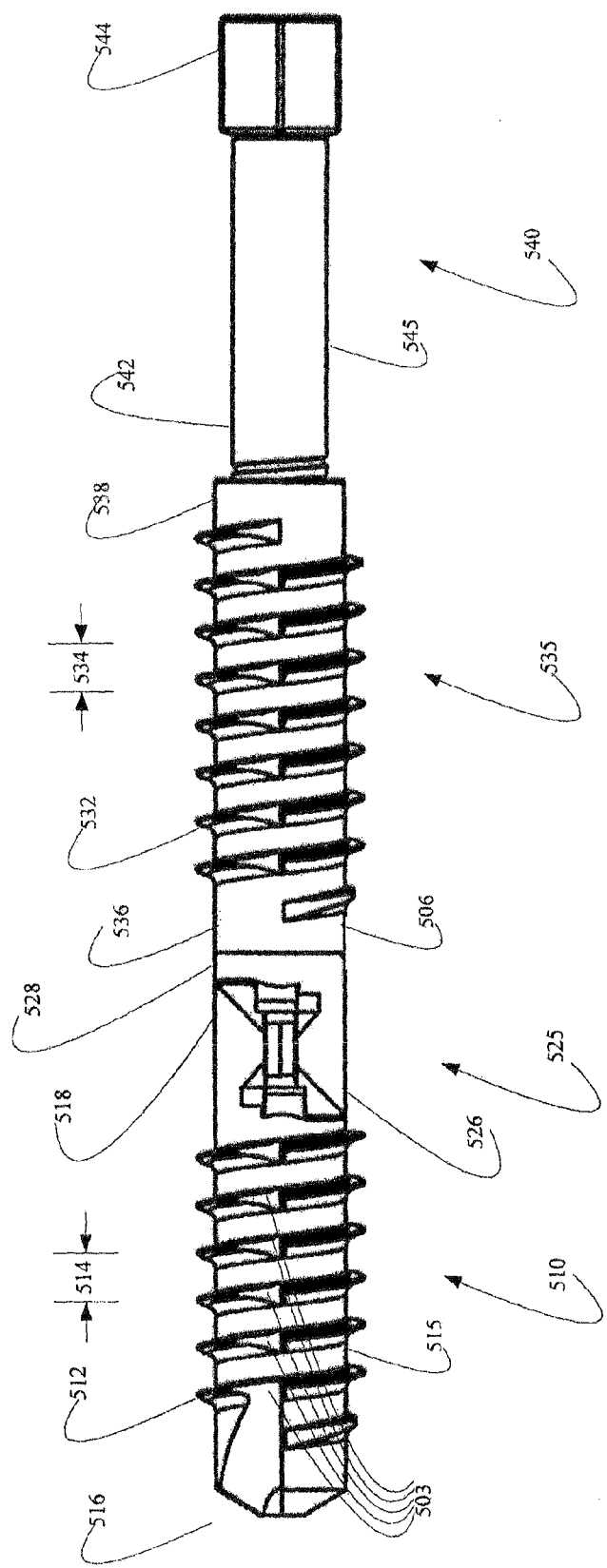
FIG. 4.3B

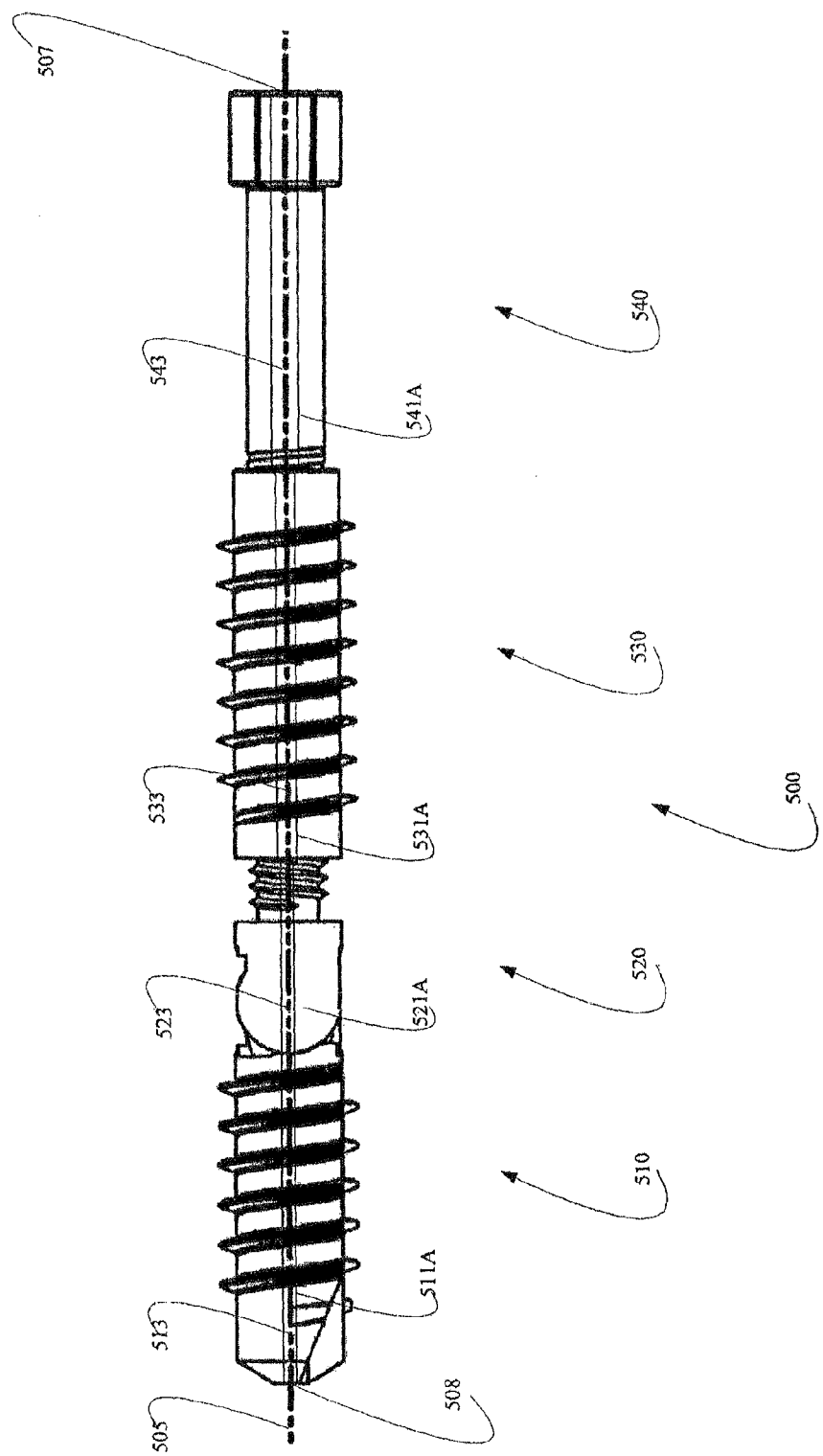
FIG. 4.4A

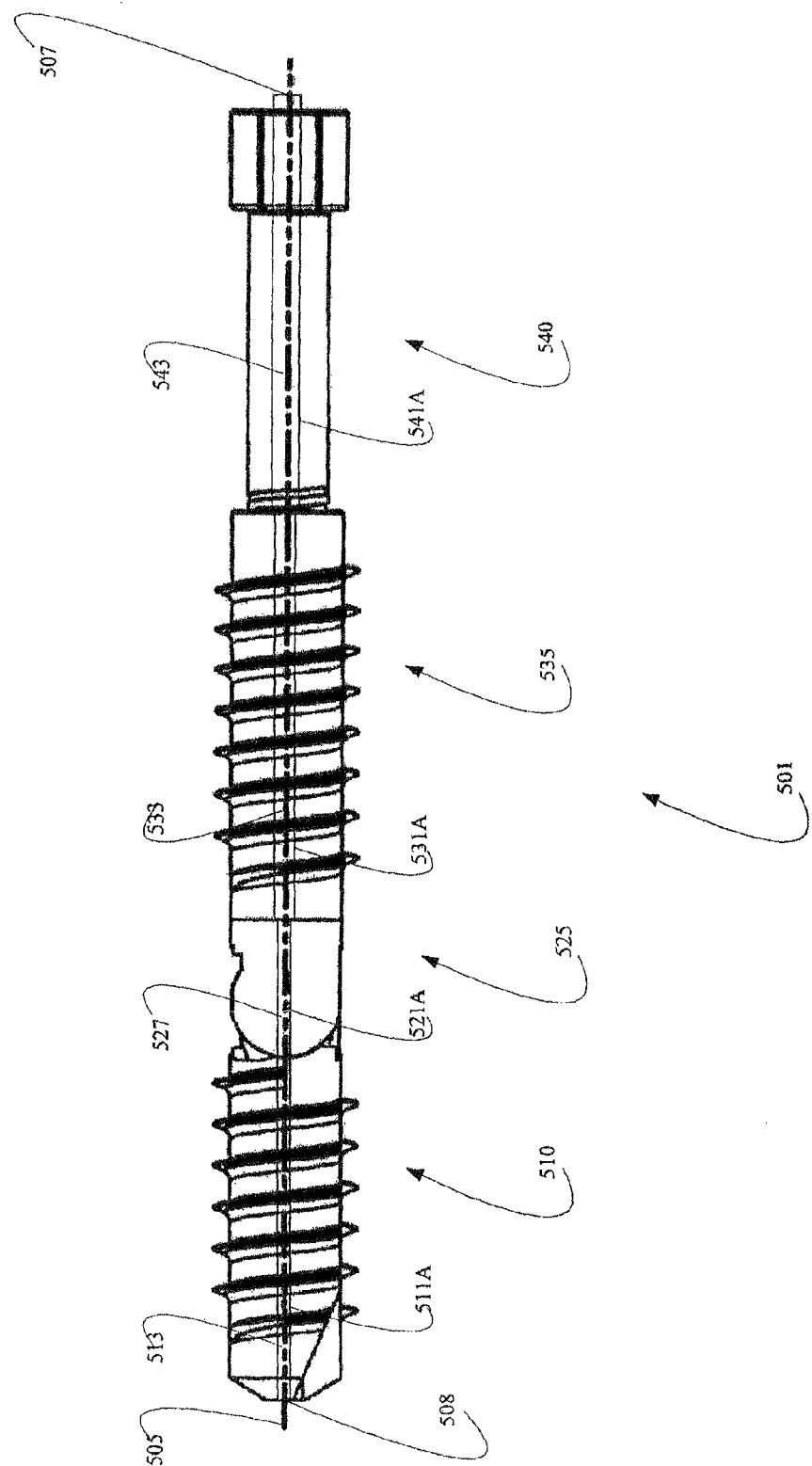
FIG. 4.4B

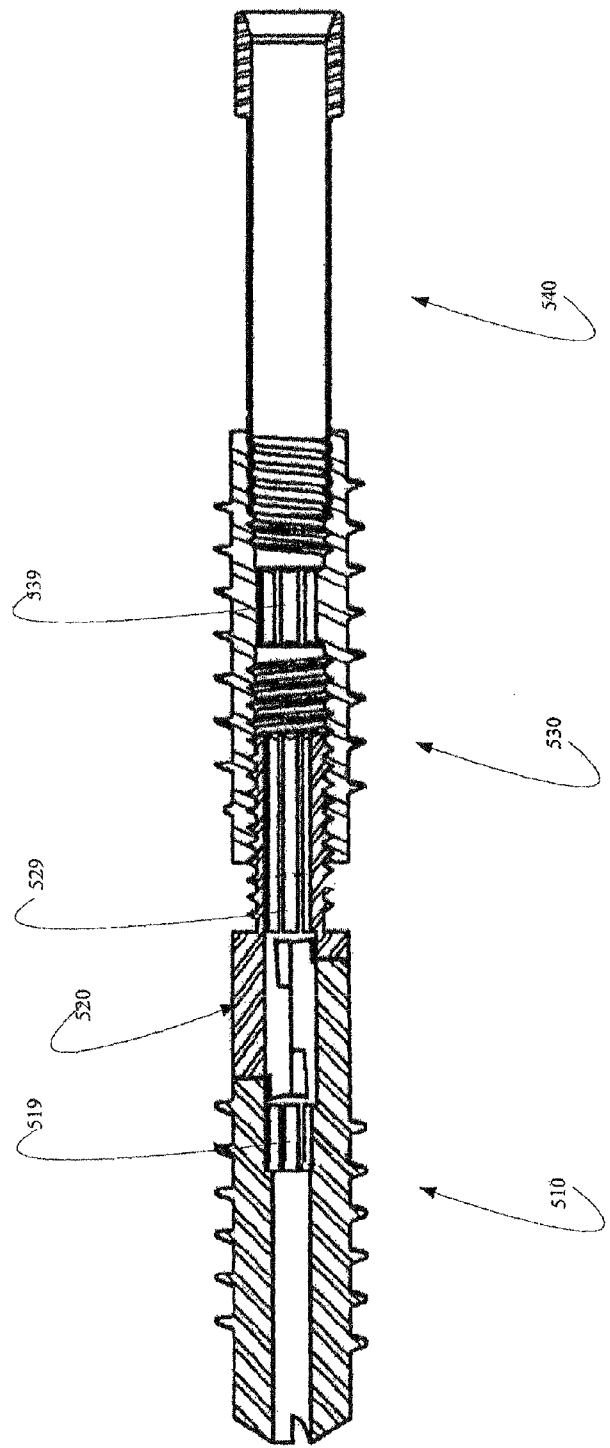
FIG. 4.5A

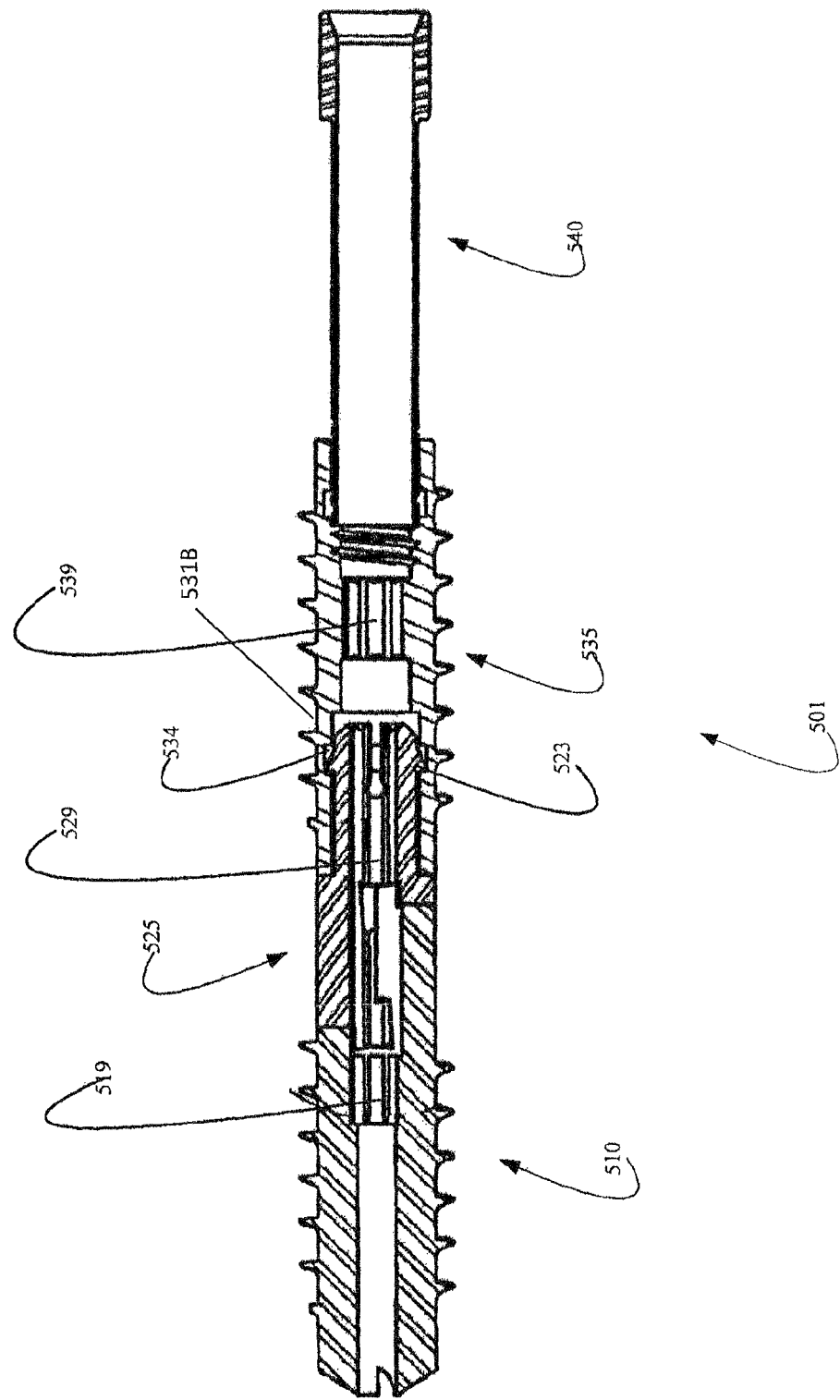
FIG. 4.5B

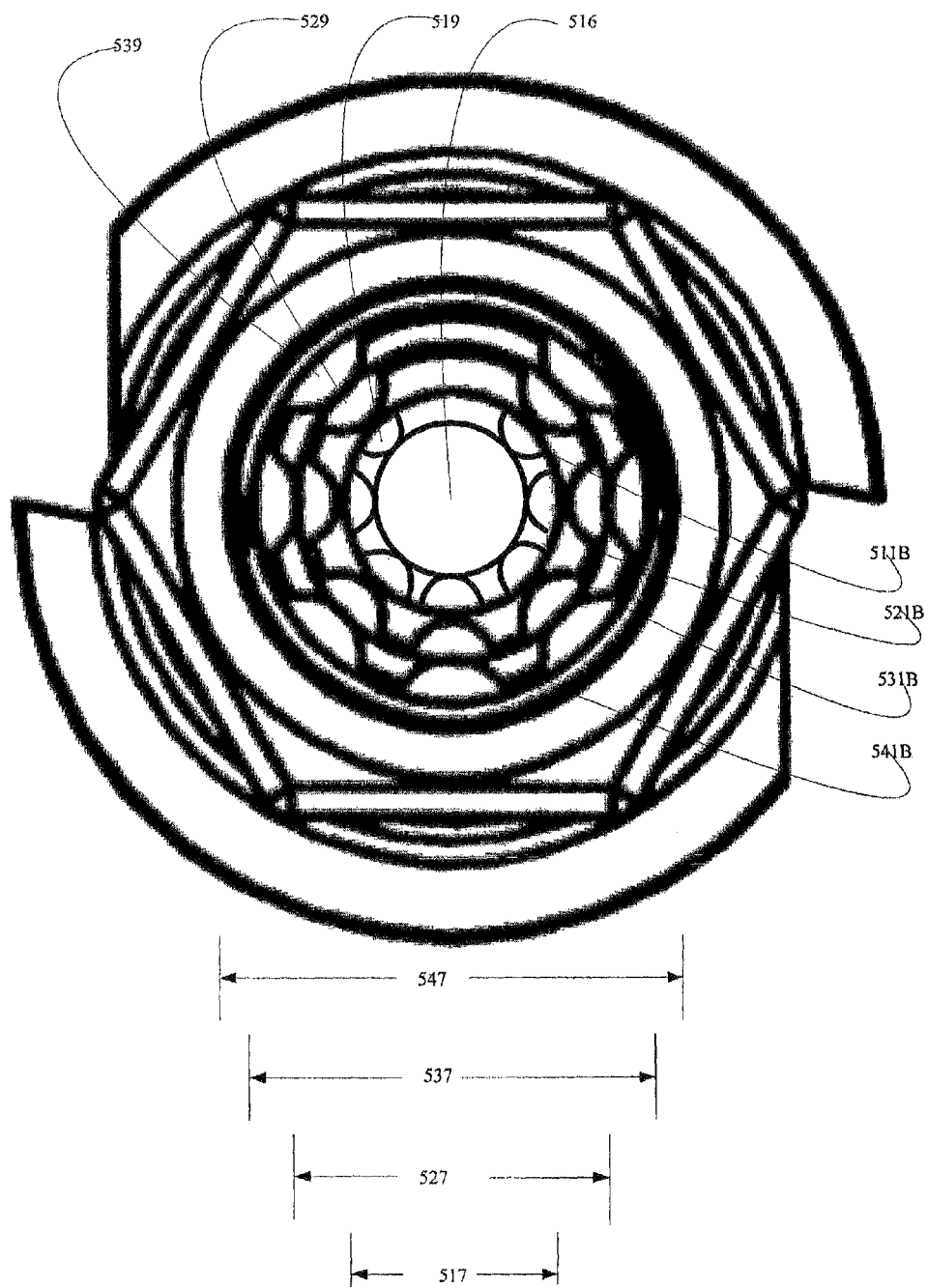
FIG. 4.6

FIG. 4.7
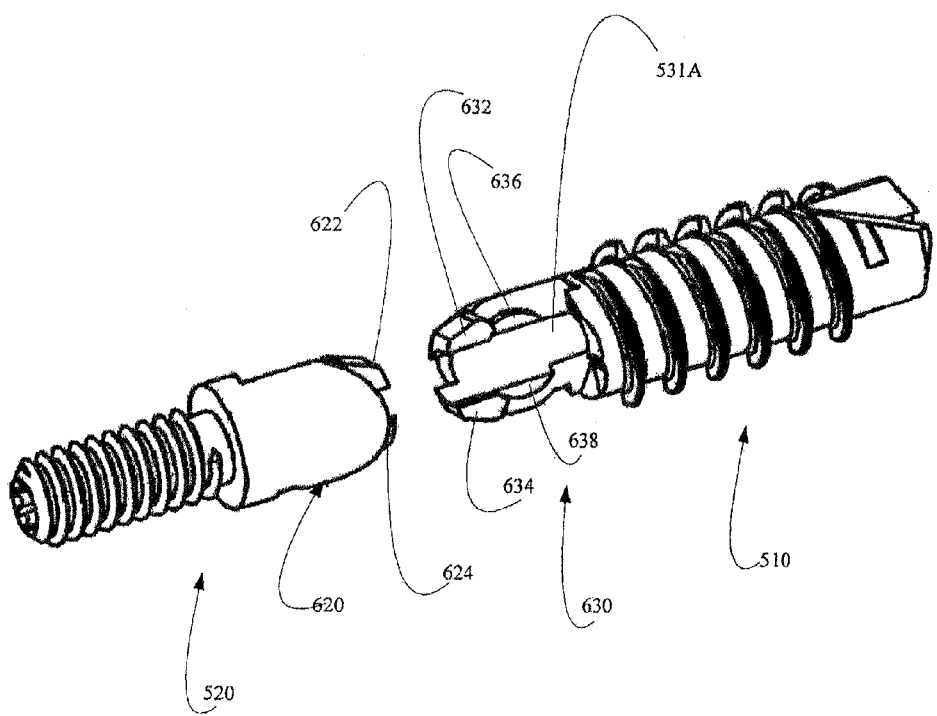

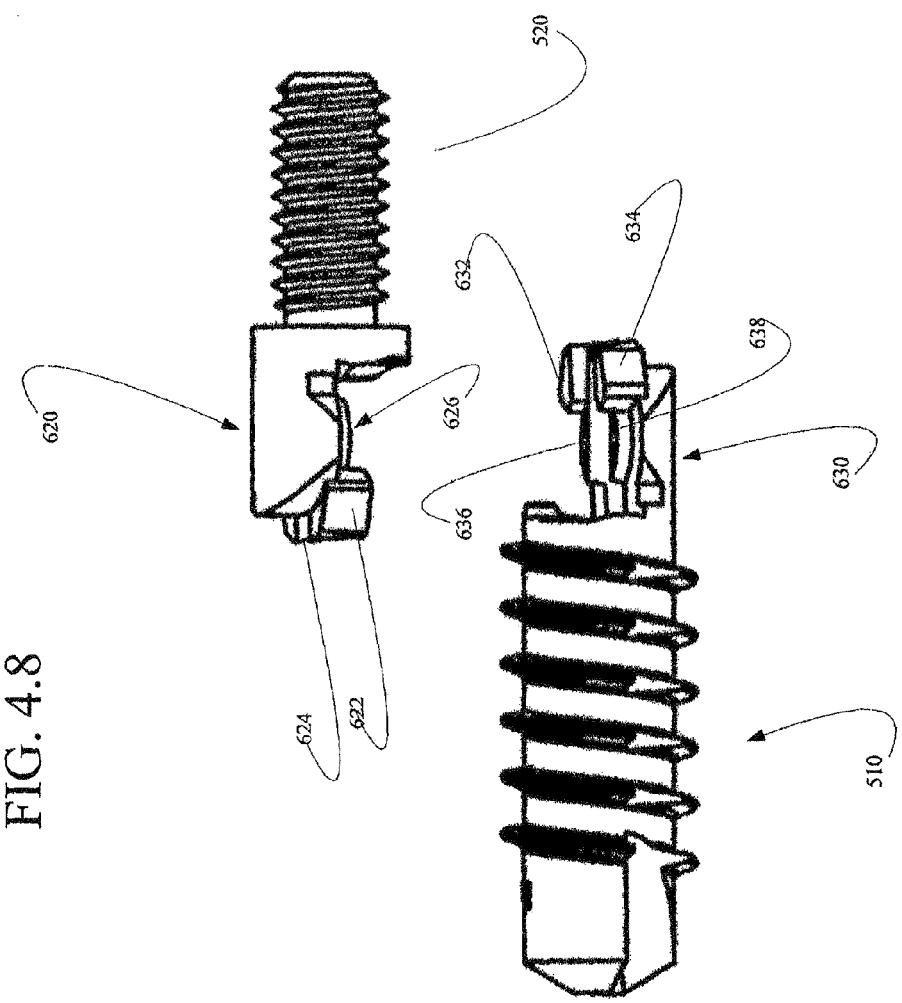
FIG. 4.8

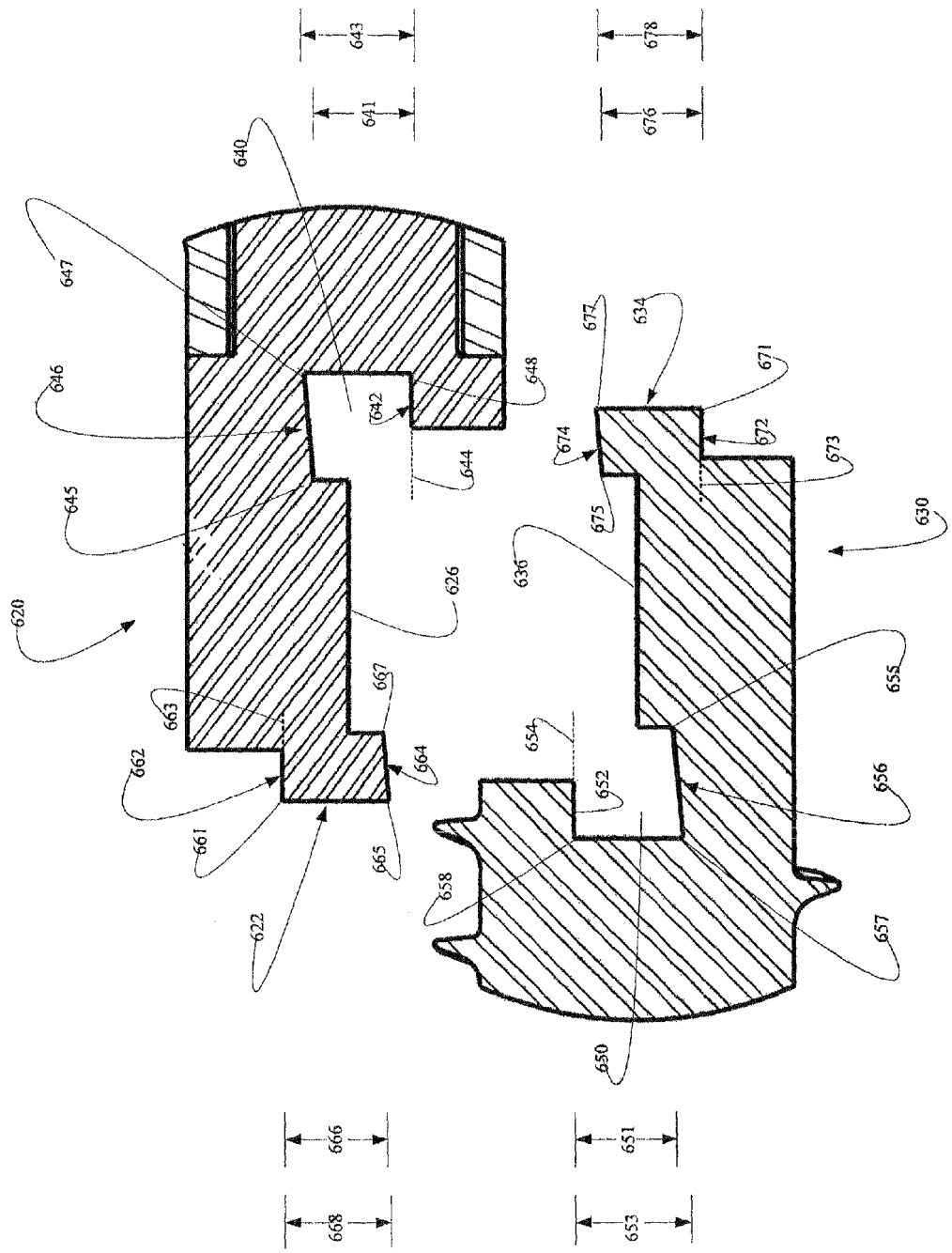
FIG. 4.9A

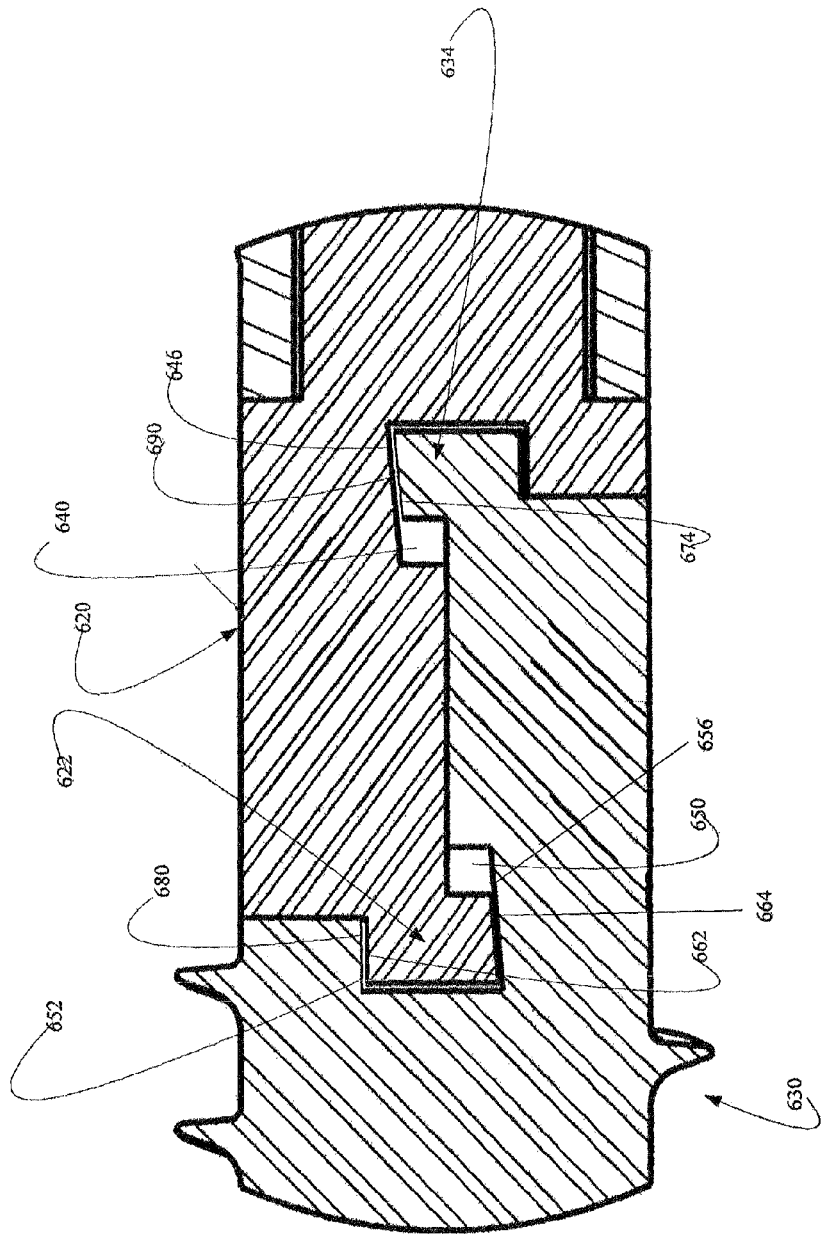
FIG. 4.9B

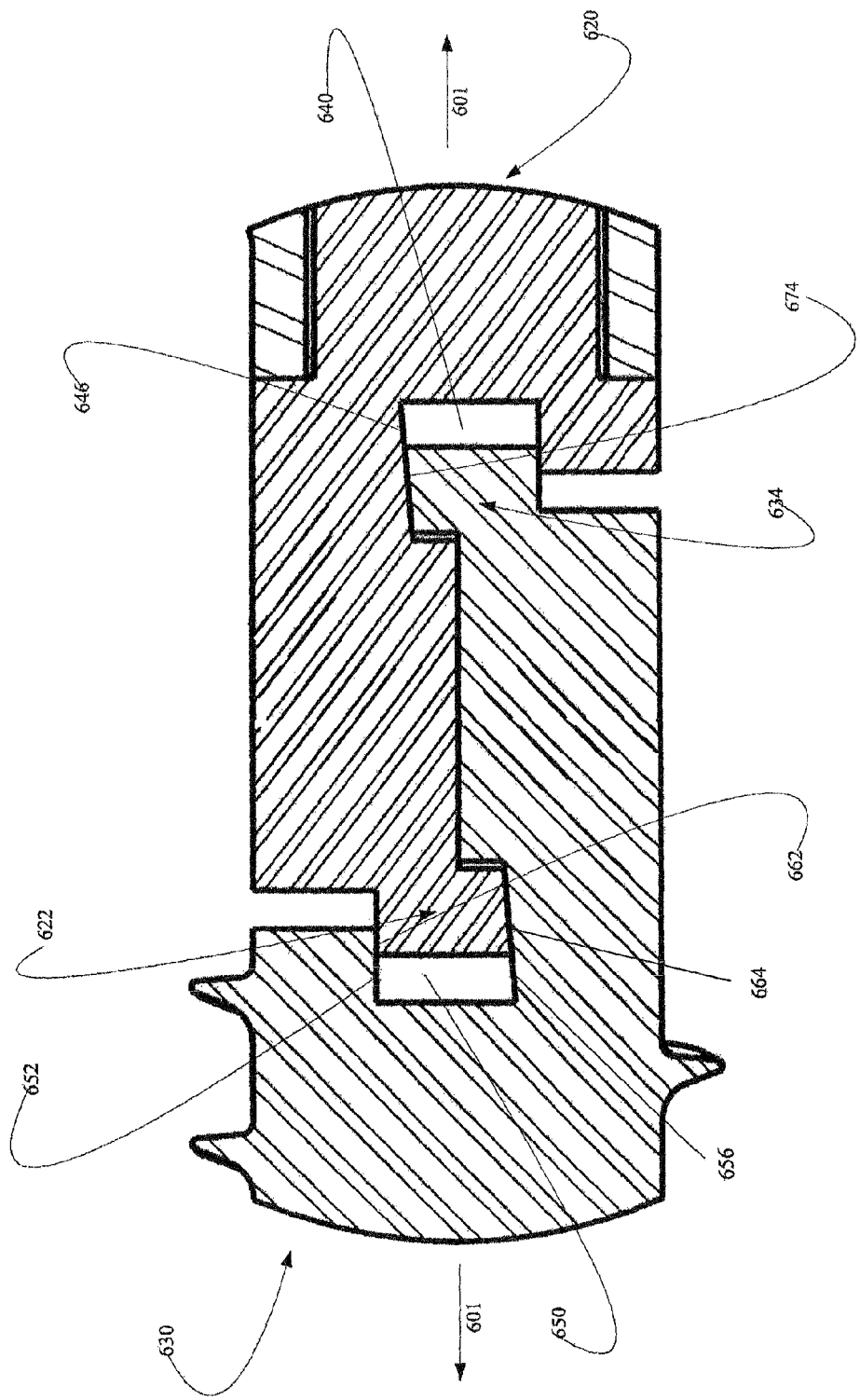
FIG. 4.9C

FIG. 4.10
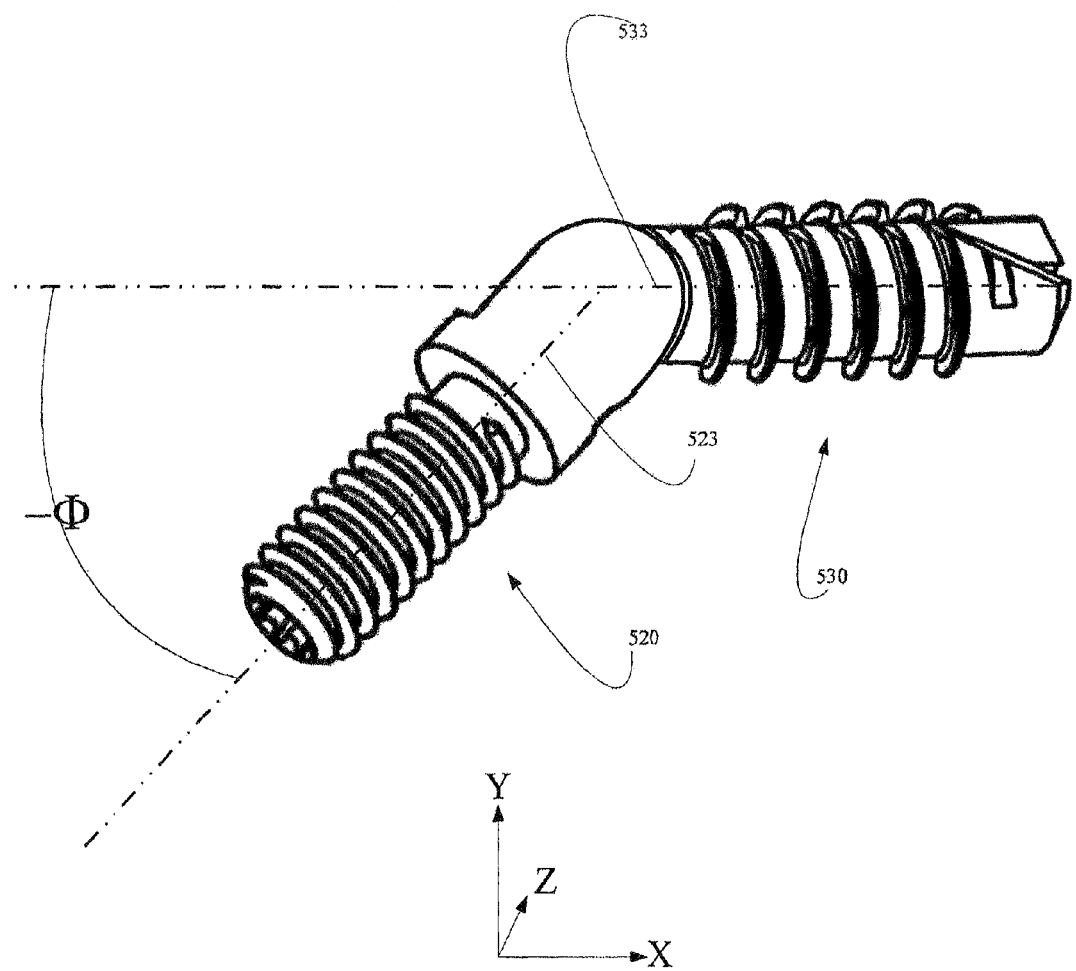

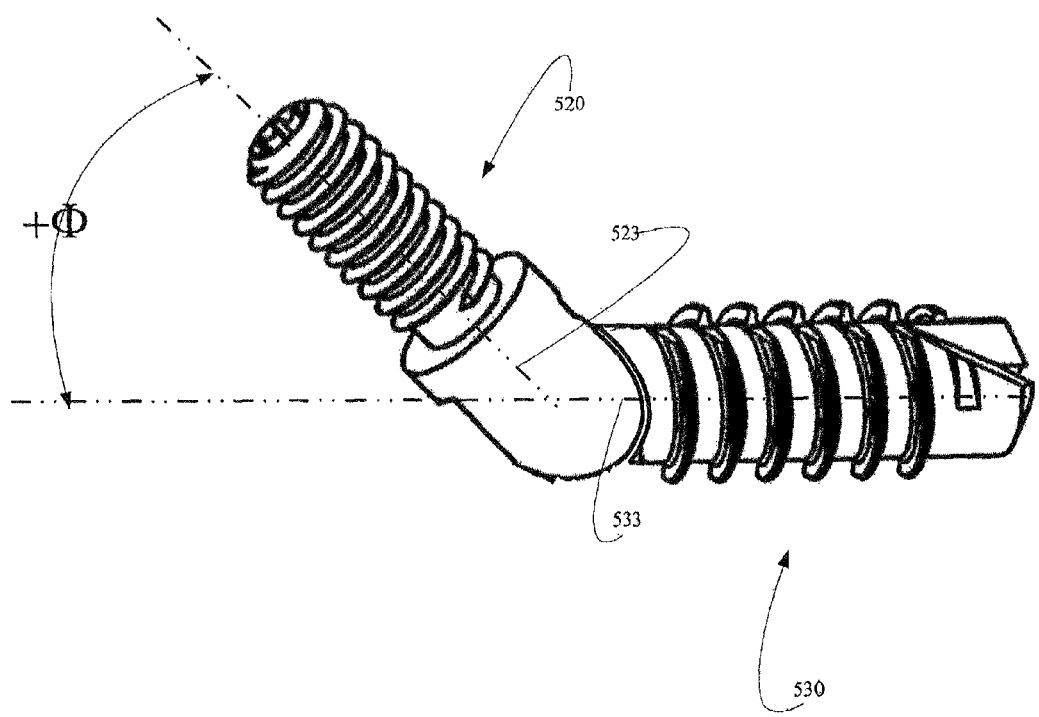
FIG. 4.11

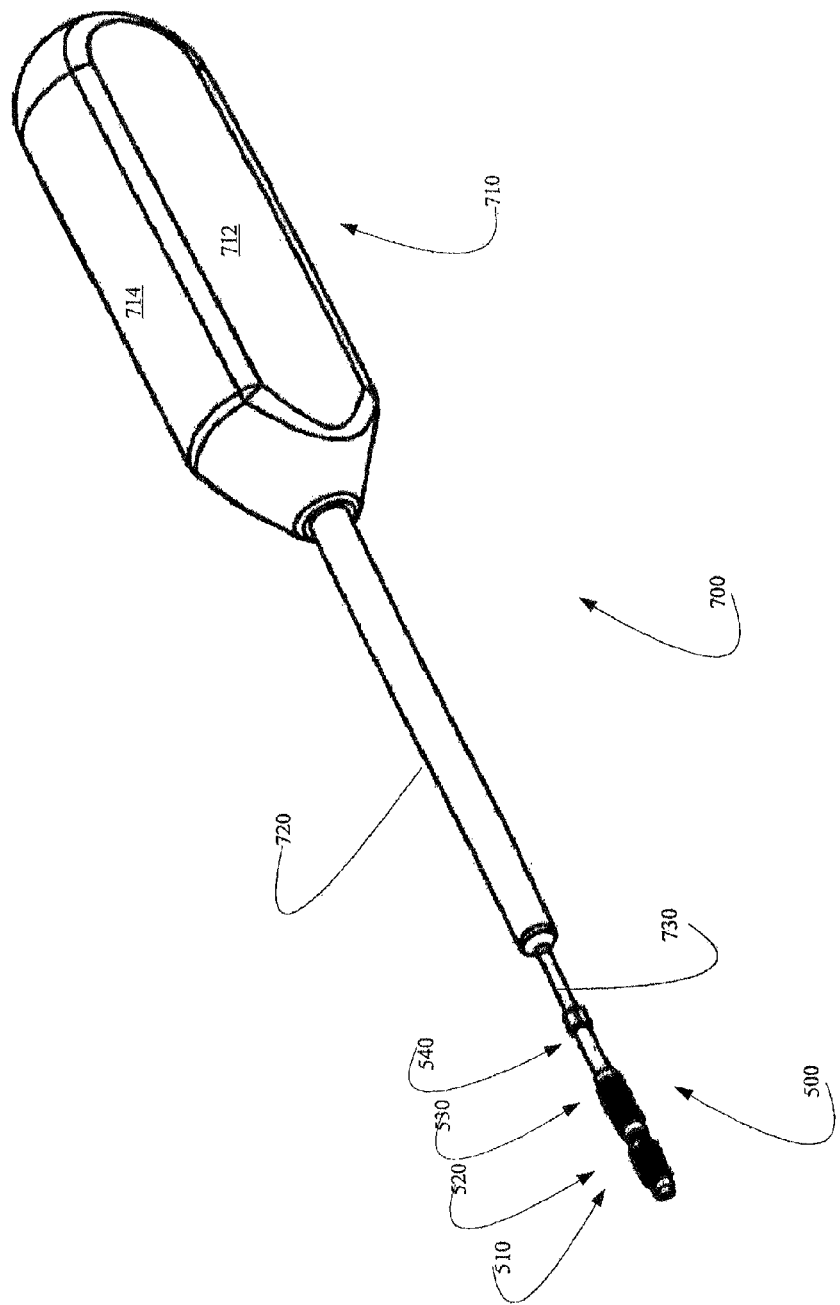
FIG. 5.1

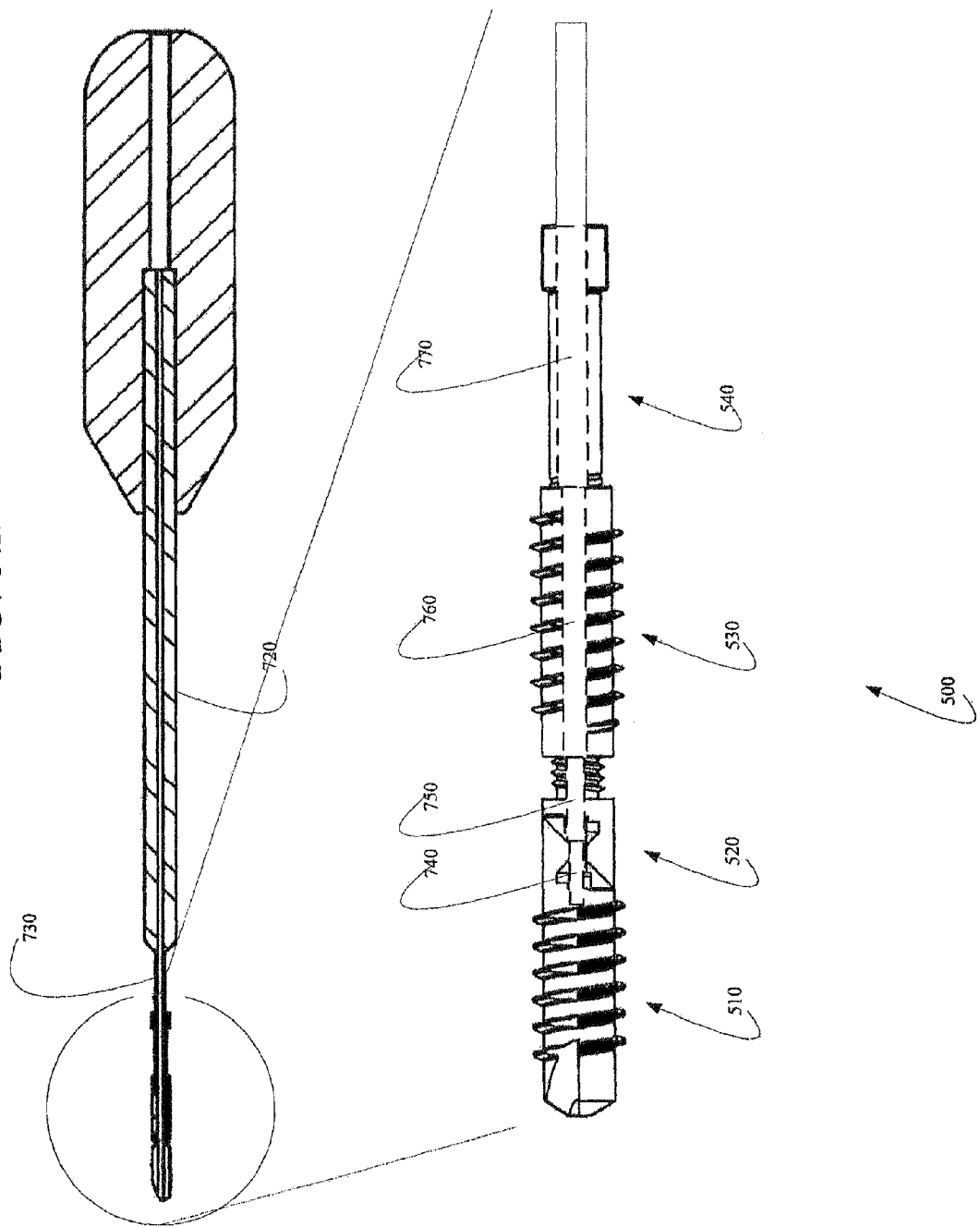
FIG. 5.2

FIG. 5.3
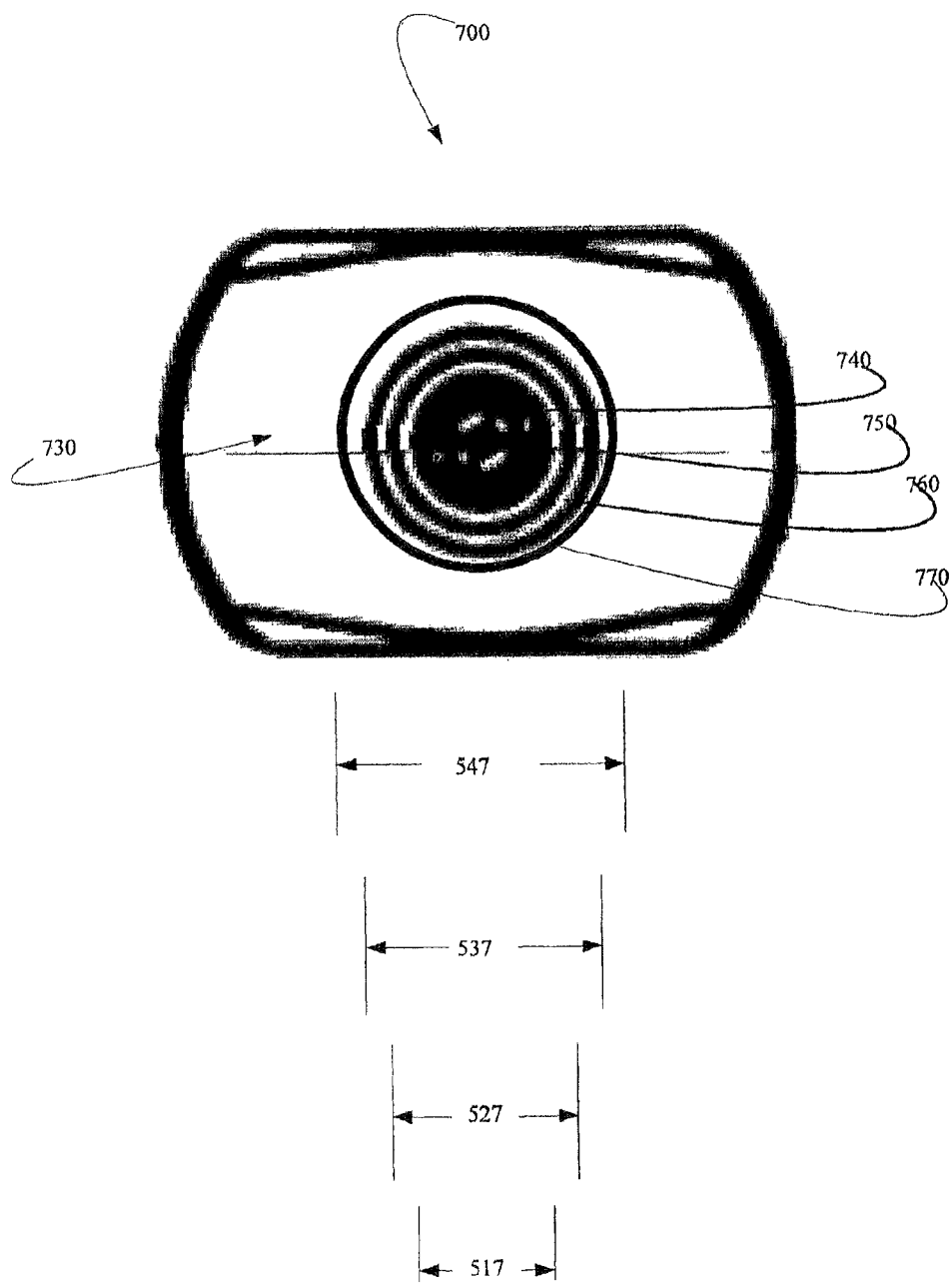

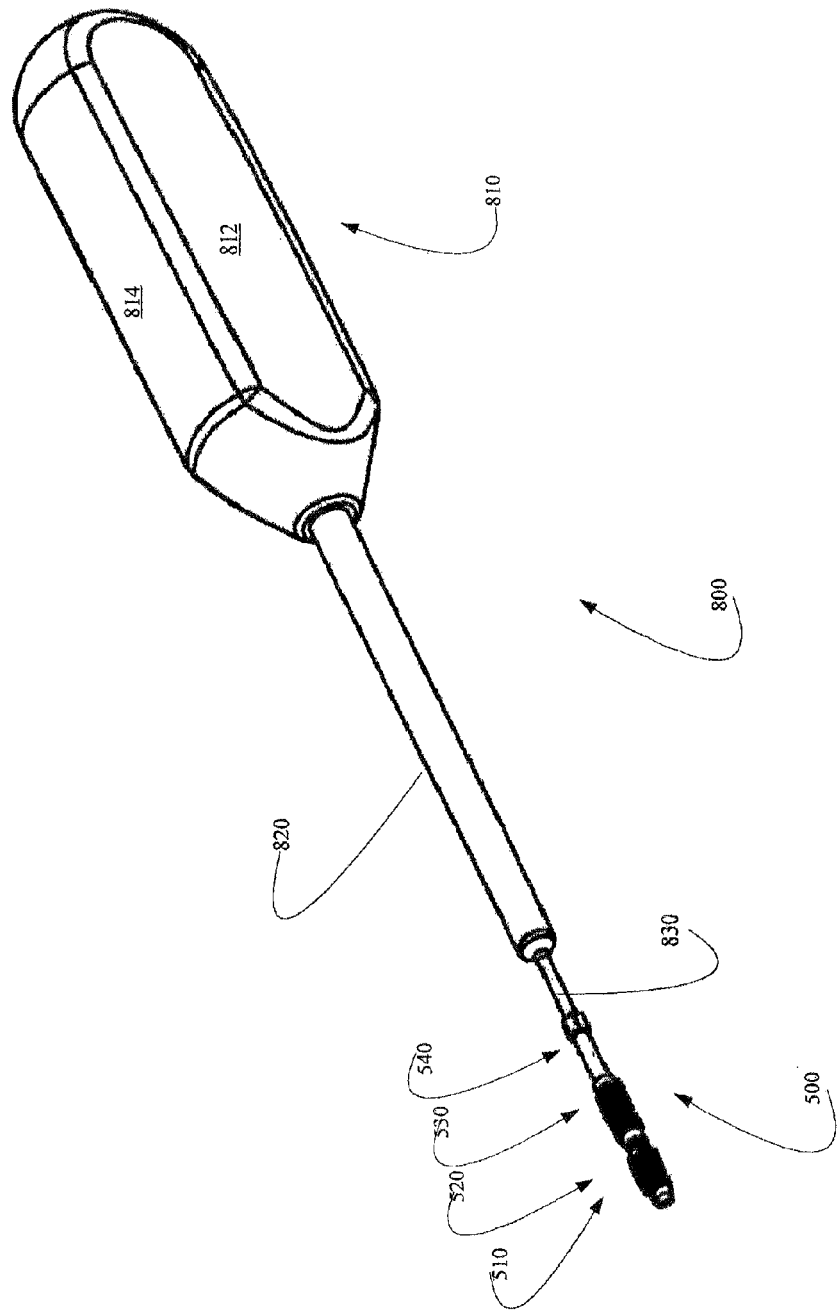

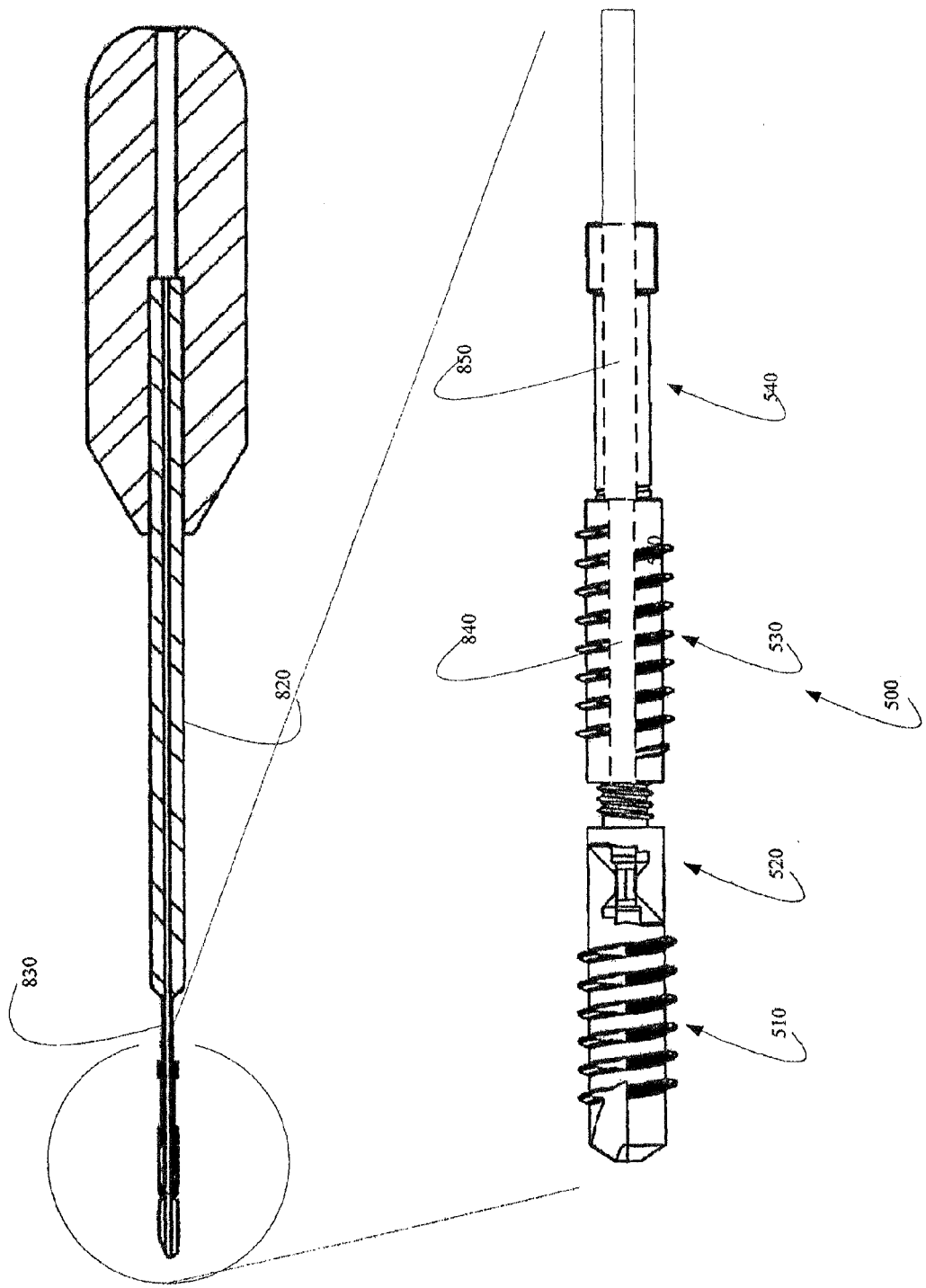
FIG. 6.2

FIG. 6.3
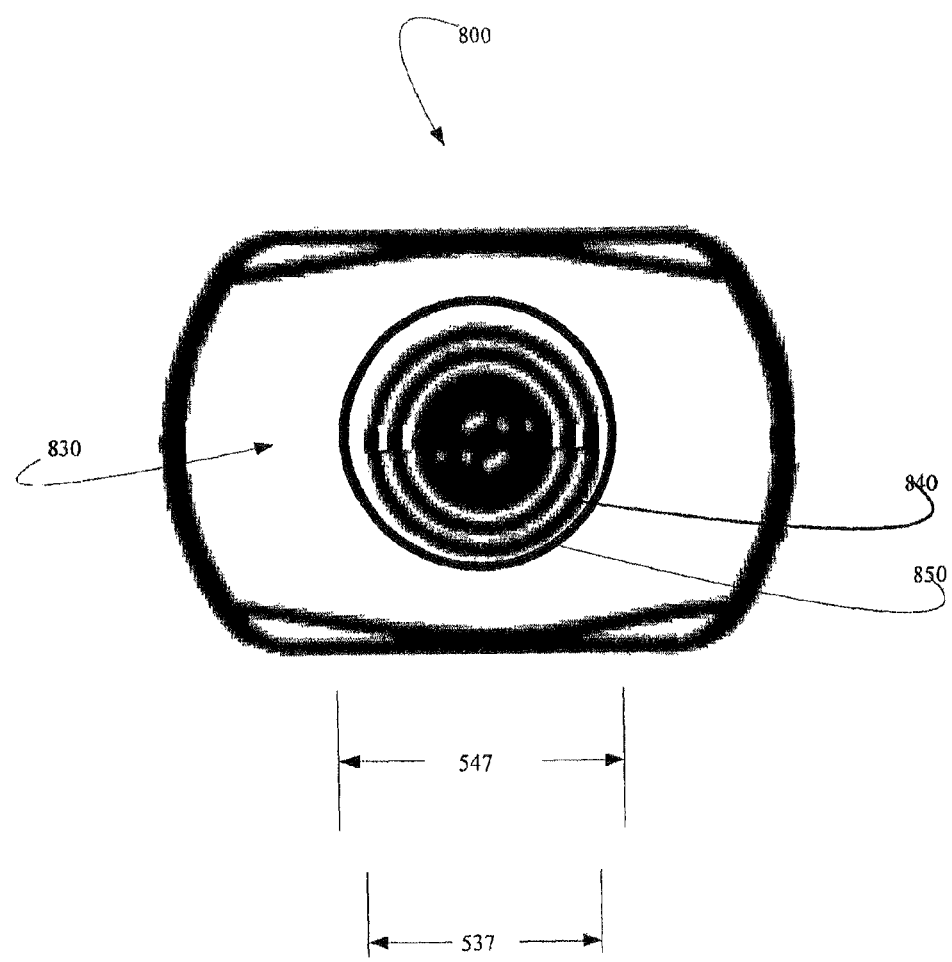

DISTAL INTERPHALANGEAL FUSION DEVICE AND METHOD OF USE

CROSS REFERENCE TO RELATED APPLICATIONS

This application claims priority from U.S. Provisional Application Ser. No. 61/238,098, filed Aug. 28, 2009.

FIELD

Implementations generally relate to a medical device and medical procedure using that device, and more particularly, to a joint fusion assembly for arthroplastic convergence of opposing ends of bones.

BACKGROUND

Patients that suffer from joint disorders often undergo arthrodesis to compress adjacent bones against one another to fixate them for fusion. Joint disorders, such as arthritis in the joints of digits, can be extremely painful. A common procedure to alleviate pain in such patients is to fixate the joint for fusion by arthrodesis. There are a number of arthrodesis techniques that promote fusion of adjacent bones of a digit (e.g., finger or toe). Historically, these techniques utilize a bone screw that draws the adjacent bones together in at a 180 degree angle. The digit then fuses at the joint in a fully-extended orientation.

This fully-extended orientation of the digit in conventional arthrodesis techniques weakens grip strength and is often not esthetically pleasing to the patient. For example, the grip strength of the hand increases when the fingers can oppose each other as the hand grasps an object. If a finger is extended, it cannot properly oppose the other fingers to grasp the object, stabilize the object in the hand, or exert as much force on the object. Moreover, the digits of a human hand rest in a flexed position; therefore, a digit that is fused in an extended position looks abnormal and is not esthetically pleasing.

Accordingly, it would be an advantage to provide a joint assembly that overcomes the disadvantages of previous technology.

SUMMARY

In one implementation, a distal interphalangeal ("DIP") fusion device connects a first bone of a patient to a second, adjacent bone of the patient. The joint assembly includes an anchor assembly and a compressor assembly. The anchor assembly is rotationally coupled to one end of the compressor assembly, such that the compressor assembly may rotate about the anchor assembly within a semi-spherical zone (three degrees of rotational freedom) and translate axially (one degree of translational freedom). In an operative position, the anchor assembly is anchored in an intermediate phalanx of a digit of a patient, the compressor assembly is contained in a distal phalanx of the digit, and the distal phalanx is flexed relative to the intermediate phalanx to create a joint angle. The joint angle is then fixated for fusion by compressing the phalanges together in the flexed position.

In another implementation, the joint assembly includes an anchor element, a compressor base element, and a compressor sleeve element. The anchor element is coupled to the medial end of the compressor base element, allowing planar rotation of the anchor element relative to the compressor base element (a single degree of rotational freedom). The compressor sleeve element is threadably coupled to a distal end of the compressor base element allowing axial rotation of the compressor sleeve element relative to the anchor base element (a single degree of translational freedom). In an operative position, the anchor element is anchored in an intermediate phalanx of a digit of a patient, the compressor element is contained in a distal phalanx of the digit, and the distal phalanx is flexed relative to the intermediate phalanx to create a joint angle. The joint angle is then fixated for fusion by threadably compressing the phalanges together in the flexed position.

In yet another implementation, a method provides for insertion of a joint assembly device into a digit of a patient. A percutaneous probe, such as a K-wire, is used to create a bore through a distal phalanx and the intermediate phalanx of a digit of a patient. A delivery tool is removeably inserted into Applicants' distal interphalangeal ("DIP") fusion device that includes an anchor assembly and a compressor assembly that are coupled together via an articulating linkage. The delivery tool extends through the compressor assembly and at least a portion of the anchor assembly. The delivery tool is then used to insert the joint assembly device into the digit by applying a first rotational (e.g., clockwise rotation) pressure to the joint assembly device at the bore. In this manner, the anchor assembly is inserted into the intermediate phalanx and the compressor assembly is inserted into the distal phalanx.

The delivery tool is removed from the joint assembly device and the distal phalanx is bent relative to the intermediate phalanx. Applicants' compressor tool is inserted into the inserted DIP fusion device, and caused to compress the distal phalanx against the intermediate phalanx by applying a second rotational (e.g., counterclockwise rotation) pressure to the compressor assembly such that the compressor assembly moves away from the anchor assembly and the joint is fixated for fusion.

Another embodiment of the invention is directed to a bone fusion device comprising an anchor assembly, the anchor assembly having a tubular cylindrical body at least a portion of which is covered by external threads adapted to engage hard tissue, the anchor assembly having a first end adapted to engage hard tissue and a second end adapted to rotationally couple with a compressor assembly; and a compressor assembly, the compressor assembly having a tubular cylindrical body at least a portion of which is covered by external threads adapted to engage hard tissue, the compressor assembly having a first end adapted to rotationally couple with the anchor assembly and a second end having a lumen adapted to admit a tool, the external threads on both the anchor assembly and the compressor assembly having substantially the same pitch and diameter.

Another embodiment of the invention is directed to a bone fusion device comprising an anchor assembly, the anchor assembly having a tubular cylindrical body at least a portion of which is covered by external threads adapted to engage hard tissue, the anchor assembly having a first end adapted to engage hard tissue and a second end adapted to rotationally couple with a compressor base assembly through a single plane of rotation; a compressor base assembly having a first end for rotatably coupling to the anchor assembly through a single plane of rotation, the compressor base assembly also having a second end for rotatably coupling to the compressor assembly through an axial plane of rotation, a compressor sleeve assembly, the compressor sleeve assembly having a tubular cylindrical body at least a portion of which is covered by external threads adapted to engage hard tissue, the compressor sleeve assembly having a first end adapted to rotationally couple with the anchor assembly through an axial plane of rotation and a second end having a lumen adapted to admit a tool, the external threads on both the anchor assembly and the compressor sleeve assembly having substantially the same pitch and diameter.

Another embodiment of the invention is directed to a bone fusion device comprising an anchor assembly, the anchor assembly having a tubular cylindrical body at least a portion of which is covered by external threads adapted to engage hard tissue, the anchor assembly having a first end adapted to engage hard tissue and a second end having a portion of a shared articulating linkage; and a compressor assembly, the compressor assembly having a tubular cylindrical body at least a portion of which is covered by external threads adapted to engage hard tissue, the compressor assembly having a first end adapted to rotationally couple with the anchor assembly through the shared articulating linkage and a second end having a lumen adapted to admit a tool, the external threads on both the anchor assembly and the compressor assembly having substantially the same pitch and diameter.

BRIEF DESCRIPTION OF THE DRAWINGS

Implementations will become more apparent from the detailed description set forth below when taken in conjunction with the drawings, in which like elements bear like reference numerals.

FIG. 1.1 is a first perspective view of Applicants' distal interphalangeal ("DIP") fusion device comprising a ball and socket articulating interconnection;

FIG. 1.2 is a second perspective view of the DIP fusion device of FIG. 1.1;

FIG. 1.3 is a first side view of the DIP fusion device of FIG. 1.1;

FIG. 1.4 is a second side view of the DIP fusion device of FIG. 1.1;

FIG. 1.5 is a front view of the device of FIG. 1.1;

FIG. 1.6 illustrates the individual components of the device of FIG. 1.1

FIG. 1.7 illustrates a lumen formed within the device of FIG. 1.1;

FIG. 1.8 depicts an enlarged view of a ball and socket interconnection between an anchor assembly and a compressor assembly;

FIG. 1.9 illustrates a socket portion of Applicants' compressor assembly;

FIG. 1.10 illustrates a portion of Applicants' anchor assembly rotated upwardly from Applicants' compressor assembly;

FIG. 1.11 illustrates a portion of Applicants' anchor assembly rotated downwardly from Applicants' compressor assembly FIG.

FIG. 2.1 depicts a perspective front elevational view of a delivery tool for the DIP fusion device of FIG. 1.1 loaded with the DIP fusion device of FIG. 1.1;

FIG. 2.2 is a sectional side view of the loaded delivery tool seen in FIG. 2.1 where a portion of the delivery tool and the DIP fusion device have been cut away to expose the internal structures therein;

FIG. 2.3 is a front view of Applicants' delivery tool for the DIP fusion device of FIG. 1.1;

FIG. 3.1 is a perspective front view of Applicants' compressor tool for the DIP fusion device of FIG. 1.1 loaded with the DIP fusion device of FIG. 1.1;

FIG. 3.2 depicts a sectional side view of the loaded compressor tool seen in FIG. 3.1 where a portion of the compressor tool and the DIP fusion device of FIG. 1.1 have been cut away to expose the internal structures therein;

FIG. 3.3 is a front view of Applicants' compressor tool for the DIP fusion device of FIG. 1.1;

FIG. 4.1A is a perspective view of one implementation of a second embodiment of Applicants' DIP fusion device;

FIG. 4.1B is a perspective view of a second implementation of the second embodiment of Applicants' DIP fusion device;

FIG. 4.2A illustrates the individual assemblies in the implementation of FIG. 4.1A used to form the DIP fusion device of FIG. 4.1;

FIG. 4.2B illustrates the individual assemblies used to form the DIP fusion device of FIG. 4.1B;

FIG. 4.3A is a first side view illustrating certain elements of the DIP fusion device of FIG. 4.1A;

FIG. 4.3B is a first side view illustrating certain elements of the DIP fusion device of FIG. 4.1B;

FIG. 4.4A is a second side view illustrating certain elements of the DIP fusion device of FIG. 4.1A;

FIG. 4.4B is a second side view illustrating certain elements of the DIP fusion device of FIG. 4.1B;

FIG. 4.5A is a cross-sectional view showing certain internal elements of the DIP fusion device of FIG. 4.1A;

FIG. 4.5B is a second side view illustrating certain elements of the DIP fusion device of FIG. 4.1B;

FIG. 4.6 is an internal view showing a plurality of lumens formed in the various assemblies comprising the DIP fusion devices of FIGS. 4.1A and 4.1B;

FIG. 4.7 is a first perspective view illustrating attachment portions disposed on Applicants' anchor assembly and on Applicants' compressor base assembly;

FIG. 4.8 is a second perspective view illustrating attachment portions disposed on Applicants' anchor assembly and on Applicants' compressor base assembly;

FIG. 4.9A is a block diagram illustrating the attachment portions of FIGS. 4.7 and 4.8;

FIG. 4.9B illustrates Applicants' attachment portions interconnected in an unlocked configuration;

FIG. 4.9C illustrates Applicants' attachment portions interconnected in a locked configuration;

FIG. 4.10 is a perspective view showing the articulating joint of FIG. 4.9 in a first configuration;

FIG. 4.11 is a perspective view showing the articulating joint of FIG. 4.9 in a second configuration;

FIG. 5.1 depicts a perspective front elevational view of a delivery tool for the DIP fusion device of FIG. 4.1;

FIG. 5.2 is a side view of the loaded delivery tool seen in FIG. 5.1 where a portion of the delivery tool and the DIP fusion device have been cut away to expose the internal structures therein;

FIG. 5.3 is a front view of Applicants' delivery tool for the DIP fusion device of FIG. 5.1;

FIG. 6.1 is a perspective front view of Applicants' compressor tool for the DIP fusion device of FIG. 5.1;

FIG. 6.2 depicts a side view of the loaded compressor tool seen in FIG. 6.1 where a portion of the compressor tool and the DIP fusion device of FIG. 5.1 have been cut away to expose the internal structures therein;

FIG. 6.3 is a front view of Applicants' compressor tool for the DIP fusion device of FIG. 5.1;

DETAILED DESCRIPTION

Figure 7:
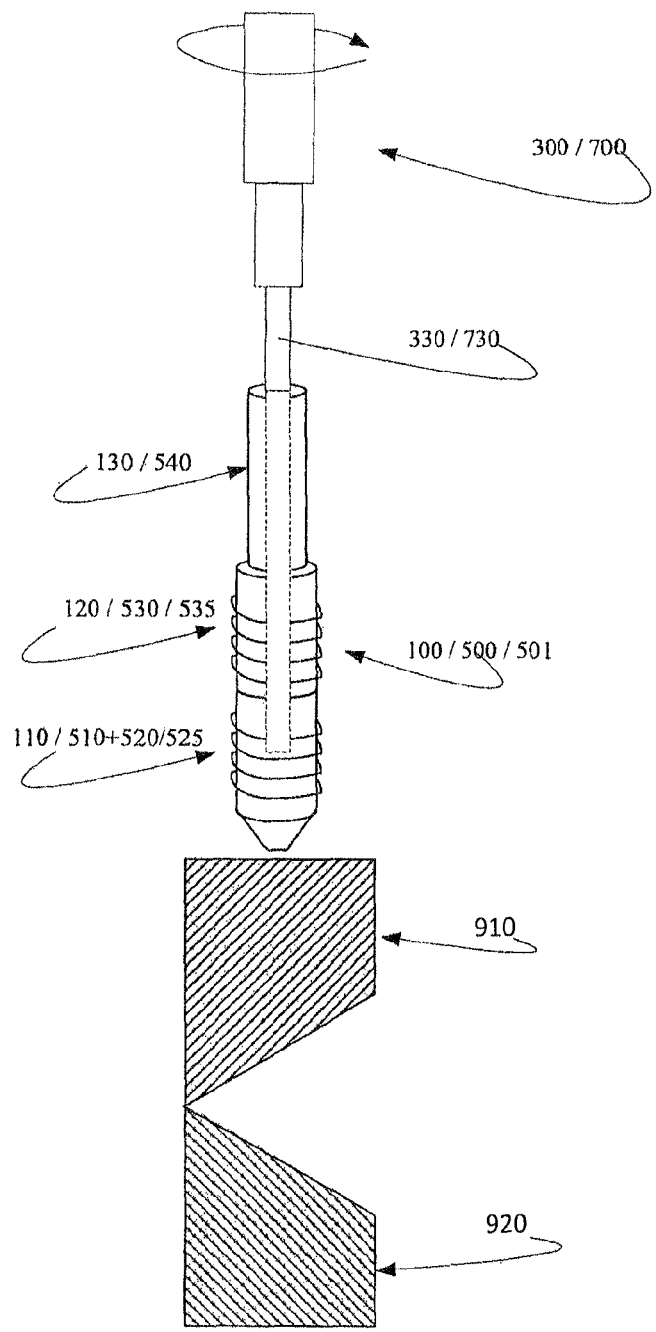
FIG. 7 illustrates Applicants' DIP fusion device loaded on Applicants' delivery tool in preparation for insertion into a distal phalanx and a medial phalanx.

This invention is described in preferred embodiments in the following description with reference to the FIG.s, in which like numbers represent the same or similar elements. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

The described features, structures, or characteristics of the invention may be combined in any suitable manner in one or more embodiments. In the following description, numerous specific details are recited to provide a thorough understanding of embodiments of the invention. One skilled in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

Several implementations disclose Applicants' distal interphalangeal ("DIP") fusion device, comprising a threaded anchor assembly that is coupled with at least one threaded compressor assembly via one or more articulating linkages. The joint assembly is inserted into two, adjacent bones of a digit of a patient (e.g. adjacent bones of a finger, thumb, or toe of a patient) such that the anchor assembly is in an intermediate phalanx while the compressor assembly is in a distal phalanx of the digit. The articulating linkage is then flexed and fixated for fusion of the two bones.

In DIP fusion device 100, the articulating linkage of the joint assembly comprises a ball and socket design. Referring to FIGS. 1.1 to 1.6, DIP fusion device 100 includes an anchor assembly 110, a compressor assembly 120, and an access port assembly 130, interlinked such that end 118 of anchor assembly 110 is rotatably coupled to end 126 of compressor assembly 120, and such that end 128 of compressor assembly 120 is threadably coupled to end 132 of access port assembly 130. In certain embodiments, distal end 134 of access port assembly 130 comprises a knurled feature 234 to facilitate rotation.

Anchor assembly 110 comprises a tubular cylindrical body 115. In certain embodiments, anchor assembly 110 is formed from titanium. In certain embodiments, anchor assembly 110 is formed from stainless steel.

Anchor assembly further comprises a longitudinal axis 113 extending from first end 116 to second end 118. In certain embodiments, anchor assembly 110, comprises a cannular form wherein a bore, lumen or cavity 111A extends from first end 116 to second end 118.

In certain embodiments, anchor assembly 110 comprises a length along longitudinal axis 113 from about 10 mm and about 40 mm. In certain embodiments, anchor assembly 110 comprises a diameter from about 2 mm to about 5 mm.

Compressor assembly 120 comprises a tubular cylindrical body 125. In certain embodiments, compressor assembly 120 is formed from titanium. In certain embodiments, compressor assembly 120 is formed from stainless steel.

Compressor assembly 120 further comprises a longitudinal axis 123 extending from first end 126 to second end 128. In certain embodiments, compressor assembly 120 comprises a cannular form wherein a bore, lumen or cavity 121A extends from first end 126 to second end 128.

In certain embodiments, compressor assembly 120 comprises a length along longitudinal axis 123 from about 10 mm and about 40 mm. In certain embodiments, compressor assembly 120 comprises a diameter from about 2 mm to about 5 mm.

Access port assembly 130 comprises a tubular cylindrical body 135. In certain embodiments, access port assembly 130 is formed from titanium. In certain embodiments, access port assembly 130 is formed from stainless steel.

Access port assembly 130 further comprises a longitudinal axis 133 extending from first end 132 to second end 134. In certain embodiments, access port assembly 130 comprises a cannular form wherein a bore, lumen or cavity 131A extends from first end 132 to second end 134.

In certain embodiments, access port assembly 130 comprises a length along longitudinal axis 133 from about 10 mm and about 40 mm. In certain embodiments, access port assembly 130 comprises a diameter from about 2 mm to about 5 mm.

As shown in FIGS. 1.1 to 1.4, in a straight configuration, DIP fusion device 100 comprises a composite longitudinal axis 105 created by aligning longitudinal axis 113 of anchor assembly 110, longitudinal axis 123 of compressor assembly 120, and longitudinal axis 133 of access port assembly 130. In this straight configuration, cavities 111A, 121A, and 131A, are also aligned to form a continuous lumen extending from a first open end 107 formed in end 134 of access port assembly 130 to second open end 108 formed in end 116 of anchor assembly 110.

In certain embodiments, anchor assembly 110, compressor assembly 120, and the access port assembly 130 comprise one or more external features that facilitate advancement or retraction of DIP fusion device 100, or elements thereof, into or out of hard and/or soft tissues. In the illustrated embodiments, first end 116 of anchor assembly 110 comprises a bit or blade shape. In certain embodiments, each of the anchor assembly 110 and the compressor assembly 120 comprise external threading 112, and 122, respectively, that facilitates advancing DIP fusion device 100 into hard tissue. In certain embodiments, the respective external threadings are formed to include grooves 104 that facilitate cutting of hard tissue, and removal of the debris formed thereby.

In certain embodiments, anchor assembly 110, and/or compressor assembly 120, and/or access port assembly 130, comprise internal features that facilitate collective or independent manipulation, i.e. rotation, of each. In certain embodiments, ridges disposed in one or more lumens formed within Applicants' DIP fusion device releaseably mate with grooved portions formed in Applicants' delivery tool and/or compressor tool.

In certain embodiments, a diameter of a lumen formed in anchor assembly 110, differs from a diameter of a lumen formed in compressor assembly 120, and further differs from a diameter of a lumen formed in access port assembly 130. For example, in certain embodiments the diameter of an anchor assembly lumen is less than the diameter of a compressor assembly lumen. In certain embodiments, the delivery tool and/or the compressor tool is formed to comprise complementary diameter elements such that different portions of the delivery tool and/or the compressor tool can only be inserted into, and releaseably mesh with, the anchor assembly 110, or with the compressor assembly 120, or with access port assembly 130. For example, in certain embodiments different portions of a delivery tool and/or a compressor tool can mesh with different asymmetrical groupings of ridges formed in an anchor assembly lumen, or in the compressor assembly lumen, or in an access port assembly lumen, to collectively or independently manipulate, i.e. rotate, one or more of those elements.

Referring now to FIGS. 1.4 and 1.7, lumen 111A formed in anchor assembly 110 comprises a diameter 106. In certain embodiments, diameter 106 is between about 1 mm and about 4 mm. Lumen 111A is defined by wall 111B. In the illustrated embodiment of FIG. 1.7, an asymmetrical grouping of rounded ridges 119 is disposed longitudinally on wall 111B. Further in the illustrated embodiment of FIG. 1.7, seven rounded ridges 119 comprise an octagonal arrangement with a missing eighth ridge. The missing eighth rounded ridge in the otherwise octagonal pattern creates an asymmetry.

Referring now to FIGS. 1.4 and 1.7, lumen 121A formed in compressor assembly 120 comprises a diameter 107. Lumen 121A is defined by wall 121B. In the illustrated embodiment of FIG. 1.7, an asymmetrical grouping of rounded ridges 129 is disposed longitudinally on wall 121B. Further in the illustrated embodiment of FIG. 1.7, seven rounded ridges 129 comprises an octagonal arrangement with a missing eighth ridge. The missing eighth rounded ridge in the otherwise octagonal pattern creates an asymmetry.

Referring now to FIGS. 1.4 and 1.7, lumen 131 formed in access port assembly 130 comprises a diameter 109. In certain embodiments, diameter 109 is between about 1.5 mm and about 4.5 mm.

In the illustrated embodiment of FIG. 1.7, second open end 108 of lumen 111A comprises a diameter 103. In certain embodiments, diameter 103 is between about 0.5 mm and about 2 mm.

FIG. 1.6 illustrates the individual assemblies comprising a first embodiment of Applicants' DIP fusion device 100. Referring now to FIG. 1.6, anchor assembly 110 comprises a semi-spherical element 210, also referred to herein as ball 210, formed on end 118. Referring now to FIGS. 1.6 and 1.9, compressor assembly 120 is formed to include a semi-spherical cavity 220, i.e. socket 220, in end 126. Arcuate wall 230 defines socket 220. In device 100, the diameters of ball 210 and socket 220 are dimensioned such that semi-spherical element 210 is rotatably disposed in semi-spherical socket 220.

FIGS. 1.10 and 1.11 show a cross-section view of ball 210 rotatably disposed in socket 220. In the illustrated embodiment of FIG. 1.10, anchor assembly 110 has been moved upwardly such that longitudinal axis 113 of anchor assembly 110 and longitudinal axis 123 of compressor assembly 120 define an angle +Φ. FIG. 1.11 shows a cross-section of a semi-spherical element 210 rotatably disposed in socket 220. In the illustrated embodiment of FIG. 1.10, anchor assembly 110 has been moved downwardly such that longitudinal axis 113 of anchor assembly 110 and longitudinal axis 123 of compressor assembly 120 define an angle −Φ.

In certain embodiments, angle Φ can be adjusted to a value between 0 degrees and 30 degrees. In certain embodiments, anchor assembly 110 can be moved with respect to compressor assembly 120 such that the angle Φ comprises a value of 0 to +/−30° off-axis rotation around a 360° conical zone.

As would be appreciated by those of ordinary skill in the art, the articulating linkage of device 100 may comprise other designs that permit rotation about one or more axes of the anchor assembly 110. For example, ball 210 may comprise a portion of the compressor assembly 120 and socket 220 may be formed in end 118 of anchor assembly 110. In certain embodiments, ball 210 may comprise a spherical shape, semi-spherical shape, or other shape, that permits movement within the conical zone described hereinabove. In certain embodiments, the articulating linkage may comprise one or more hinged connections that permit motion within a respective plane, or a combination thereof.

The articulating linkage of Applicants' DIP fusion device 100 may be locked in a certain configuration through a high friction interlocking surface-to-surface compression between the anchor assembly 110 and the compressor assembly 120. In certain embodiments, outer surface 212 of ball 210, and/or wall 230 of socket 220, comprises a plurality of microscopic grooves and dimples formed using Electric Discharge Machining (EDM). In certain embodiments, outer surface 212 of ball 210, and/or wall 230 of socket 220, comprises a plurality of microscopic grooves and dimples formed using an abrasion process. In certain embodiments, outer surface 212 of ball 210, and/or wall 230 of socket 220, comprises a chemical or material coating disposed thereon.

For example, if outer surface 212 of ball 210, and/or wall 230 of socket 220, comprise a plurality of microscopic grooves and dimples formed using Electric Discharge Machining (EDM) that mechanically interlock, when a tensile force is exerted on anchor assembly 110 and compressor assembly 120 the textured surfaces impact one another, and a high friction interlocking connection is created between the anchor assembly 110 and the compressor assembly 120. In this manner, once the articulating linkage is rotated to define a preferred configuration of compressor assembly 120 relative to anchor assembly 110, that preferred configuration can be fixated by pulling the compressor assembly 120 away from the anchor assembly 110, thereby putting anchor assembly 110 and compressor assembly 120 in tension. Placing the ball and socket elements in tension thereby secures or fixates Applicants' DIP fusion device 100 in a preferred configuration.

FIG. 2.1 illustrates Applicants' DIP fusion device 100 removeably disposed on Applicants' delivery tool 300. Delivery tool comprises handle 310, shaft 320, and loading portion 330. FIG. 2.2 shows a cross-section view of DIP fusion device 100 disposed on loading portion 330 of delivery tool 300. Referring now to FIGS. 2.2 and 2.3, loading portion 330 comprises a series of cylindrical assemblies having differing diameters. In the illustrated embodiment of FIGS. 2.2 and 2.3, loading portion 330 comprises tubular assemblies 332, 334, and 336.

Tubular assembly 332 comprises a diameter 109. Interior lumen 131A formed in access port assembly 130 comprises a diameter 109. Therefore, tubular assembly 332 can be inserted into lumen 131A.

Tubular assembly 334 comprises a diameter 107 wherein diameter 107 is less than diameter 109. Interior lumen 121A formed in compressor assembly 120 comprises a diameter 107. Therefore, tubular assembly 332 can be inserted into lumen 131A and lumen 121A.

Tubular assembly 336 comprises a diameter 106 wherein diameter 106 is less than diameter 107. Interior lumen 111A formed in anchor assembly 110 comprises a diameter 106. Therefore, tubular assembly 336 can be inserted into lumen 131A, lumen 121A, and lumen 111A.

Tubular assembly 334 is formed to include an asymmetrical pattern of grooves extending inwardly from an outer surface. A total of 7 grooves are formed in an octagonal arrangement with a missing eighth groove. The missing eighth groove in the otherwise octagonal pattern creates an asymmetry. The afore-described asymmetrical pattern of ridges 129 formed in wall 121B defining lumen 121A can mesh with the asymmetrical pattern of grooves formed in tubular assembly 334 if, and only if, the "missing" ridge of wall 121B is aligned with the "missing" groove of tubular assembly 334.

Tubular assembly 336 is formed to include an asymmetrical pattern of grooves extending inwardly from an outer surface. A total of 7 grooves are formed in an octagonal arrangement with a missing eighth groove. The missing eighth groove in the otherwise octagonal pattern creates an asymmetry. The afore-described asymmetrical pattern of rounded ridges 119 formed in wall 111B defining lumen 111A can mesh with the asymmetrical pattern of grooves formed in tubular assembly 336 if, and only if, the "missing" ridge of wall 111B is aligned with the "missing" groove of tubular assembly 336.

In certain embodiments, delivery tool 300 is "clocked" or marked to indicate the orientation of the "missing" grooves. Using this indication, the plane of operation of the DIP fusion device 100 can be determined visually. Examples or markings or indicators of orientation can include: color markings on the delivery tool 300 and/or DIP fusion device 100, delivery tool handle 310 or delivery tool neck shape or texture, a lock-and-key fit between the out surface of the delivery tool 300 and the inner surface of the DIP fusion device 100, or a combination thereof.

FIG. 3.1 illustrates a compressor tool 400 with DIP fusion device 100 loaded thereon. In the illustrated embodiment of FIG. 3.1, compressor tool 400 comprises a compressor tool handle 410, a neck 420, and a loading region or portion 430.

FIG. 3.2 shows a cross-section view of DIP fusion device 100 disposed on loading portion 430 of compression tool 400. Referring now to FIGS. 3.2 and 3.3, loading portion 430 comprises a series of cylindrical elements having differing diameters. In the illustrated embodiment of FIGS. 3.2 and 3.3, loading portion 430 comprises tubular assemblies 432 and 434.

Tubular assembly 432 comprises a diameter 109. Interior lumen 131A formed in access port assembly 130 comprises a diameter 109. Therefore, tubular assembly 432 can be inserted into lumen 131A.

Tubular assembly 434 comprises a diameter 107 wherein diameter 107 is less than diameter 109. Interior lumen 121A formed in compressor assembly 120 comprises a diameter 107. Therefore, tubular assembly 432 can be inserted into lumen 131A and lumen 121A.

Tubular assembly 434 is formed to include an asymmetrical pattern of grooves extending inwardly from an outer surface. A total of 7 grooves are formed in an octagonal arrangement with a missing eighth groove. The missing eighth groove in the otherwise octagonal pattern creates an asymmetry. The afore-described asymmetrical pattern of ridges 129 formed in wall 121B defining lumen 121A can mesh with the asymmetrical pattern of grooves formed in tubular assembly 334 if, and only if, the "missing" ridge of wall 121B is aligned with the "missing" groove of tubular assembly 334.

In certain embodiments, compression tool 400 is "clocked" or marked to indicate the orientation of the "missing" grooves. Using this indication, the plane of operation of the DIP fusion device 100 can be determined visually. Examples of markings or indicators of orientation can include: color markings on the compression tool 400 and/or DIP fusion device 100, compression tool handle 410 or compression tool neck shape or texture, a lock-and-key fit between the outer surface of the compression tool 400 and the inner surface of the DIP fusion device 100, or a combination thereof.

In certain embodiments, the loading region 430 of the compressor tool 400 may be shorter than the loading portion 330 of the delivery tool 300. For example, as shown in an enlarged cut away perspective of FIG. 3.2, the compressor tool 400 may be inserted into DIP fusion device 100 such that loading region 430 extends into the compressor assembly 120 and access port assembly 130 but does not extend into the anchor assembly 110. In this manner, the compressor tool 400 may be used to manipulate (e.g, rotate) the compressor assembly 120 independent of the anchor assembly 110.

Two implementations of a second embodiment of Applicants' distal interphalangeal ("DIP") fusion device include an articulating linkage comprising a pair of interlocking and moveable assemblies. The first implementation, shown in FIGS. 4.1A to 4.5A, DIP fusion device 500 includes anchor assembly 510, a compressor base assembly 520, a compressor sleeve assembly 530, and an access port assembly 540, interlinked such that end 518 of anchor assembly 510 is rotatably coupled to end 526 of compressor base assembly 520, and wherein end 528 of compressor base assembly 520 is threadably coupled to end 536 of compressor sleeve assembly 530, and wherein end 538 of compressor sleeve assembly 530 is threadably coupled to end 542 of access port assembly 540. In certain embodiments, distal end 544 of access port assembly 540 comprises a knurled configuration.

The second implementation, shown in FIGS. 4.1B to 4.5B, DIP fusion device 501 includes anchor assembly 510, a compressor base assembly 525, a compressor sleeve assembly 535, and an access port assembly 540, interlinked such that end 518 of anchor assembly 510 is rotatably coupled to end 526 of compressor base assembly 525, and wherein end 528 of compressor base assembly 525 is rotatably coupled to end 536 of compressor sleeve assembly 535, and wherein end 538 of compressor sleeve assembly 535 is threadably coupled to end 542 of access port assembly 540. In certain embodiments, distal end 544 of access port assembly 540 comprises a knurled configuration.

Referring to FIG. 4.2B, compressor base assembly 525 comprises tubular member 522 attached to, and extending outwardly from, attachment portion 620. An annular ridge 523 is disposed on the distal end of tubular member 522. A groove 524 bifurcates annular ridge 523.

Referring to FIGS. 4.4B and 4.5B, compressor sleeve assembly 535 comprises annular groove 534 formed in wall 531B of lumen 531A. Tubular member 522 is inserted into lumen 531A such that annular ridge 523 is disposed in annular groove 534 thereby rotatably interconnecting compressor base assembly 525 and compressor sleeve assembly 535.

Anchor assembly 510 comprises a tubular cylindrical body 515. In certain embodiments, anchor assembly 510 is formed from titanium. In certain embodiments, anchor assembly 510 is formed from stainless steel.

Anchor assembly 510 further comprises a longitudinal axis 513 extending from first end 516 to second end 518. In certain embodiments, anchor assembly 510 comprises a cannular form wherein a bore, lumen or cavity 511A extends from first end 516 to second end 518.

In certain embodiments, anchor assembly 510 comprises a length along longitudinal axis 513 from about 10 mm and about 40 mm. In certain embodiments, anchor assembly 510 comprises a diameter from about 2 mm to about 5 mm.

In certain embodiments, compressor base assembly 520/525 is formed from titanium. In certain embodiments, compressor base assembly 520/525 is formed from stainless steel.

Compressor base assembly 520/525 further comprises a longitudinal axis 527 extending from first end 526 to second end 528. In certain embodiments, compressor base assembly 520/525 comprises a cannular form wherein a bore, lumen or cavity 521 extends from first end 526 to second end 528.

In certain embodiments, compressor base assembly 520/525 comprises a length along longitudinal axis 527 from about 5 mm and about 40 mm. In certain embodiments, compressor base assembly 520/525 comprises a diameter from about 2 mm to about 5 mm.

Compressor sleeve assembly 530/535 comprises a tubular cylindrical body 506. In certain embodiments, compressor sleeve assembly 530/535 is formed from titanium. In certain embodiments, compressor sleeve assembly 530/535 is formed from stainless steel.

Compressor sleeve assembly 530/535 further comprises a longitudinal axis 533 extending from first end 536 to second end 538. In certain embodiments, compressor sleeve assembly 530/535 comprises a cannular form wherein a bore, lumen or cavity 531A extends from first end 536 to second end 538.

In certain embodiments, compressor sleeve assembly 530/535 comprises a length along longitudinal axis 533 from about 10 mm and about 40 mm. In certain embodiments, compressor sleeve assembly 530/535 comprises a diameter from about 2 mm to about 5 mm.

Access port assembly 540 comprises a tubular cylindrical body 545. In certain embodiments, access port assembly 540 is formed from titanium. In certain embodiments, access port assembly 540 is formed from stainless steel.

Access port assembly 540 further comprises a longitudinal axis 543 extending from first end 542 to second end 544. In certain embodiments, access port assembly 540 comprises a cannular form wherein a bore, lumen or cavity 541A extends from first end 542 to second end 544.

In certain embodiments, access port assembly 540 comprises a length along longitudinal axis 543 from about 10 mm and about 40 mm. In certain embodiments, access port assembly 540 comprises a diameter from about 2 mm to about 5 mm.

As shown in FIGS. 4.1A to 4.4A and in FIGS. 4.1B to 4.4B, in a straight configuration DIP fusion device 500/501 comprises a composite longitudinal axis 505 created by aligning longitudinal axis 513 of anchor assembly 510, longitudinal axis 527 of compressor base assembly 520/525, longitudinal axis 533 of compressor sleeve assembly 530/535, and longitudinal axis 543 of access port assembly 540. In this straight configuration, cavities 511A, 521A, 531A, and 541A, are also aligned to form a continuous lumen extending from a first open end 507 formed in end 544 of access port assembly 540 to second open end 508 formed in end 516 of anchor assembly 510.

In certain embodiments, anchor assembly 510 and compressor sleeve assembly 530/535, comprise one or more external features that facilitate advancement or retraction of DIP fusion device 500, or elements thereof, into or out of hard and/or soft tissues. In the illustrated embodiments, first end 516 of anchor assembly 510 comprises a bit or blade shape.

In certain embodiments, each of the anchor assembly 510 and the compressor sleeve assembly 530/535 comprise external threading 512, and 532, respectively, that facilitates advancing DIP fusion device 500/501 into hard tissue. In certain embodiments, the respective external threadings are formed to include grooves 503 that facilitate cutting of hard tissue, and removal of the debris formed thereby.

Referring now to FIG. 4.3A, in DIP fusion device 500 a compressor base threading 522A comprises a compressor base pitch 724 that matches a compressor sleeve pitch 537 of compressor sleeve threading 532. In certain embodiments, the matching pitches comprise a 1:1 ratio. In certain embodiments, the matching pitches comprise a ratio, such as 1:2, 2:1 or 4:3, for example.

In certain embodiments, anchor assembly 510, and/or compressor base assembly 520/525, and/or compressor sleeve assembly 530/535, and/or access port assembly 540, comprise internal features that facilitate collective or independent manipulation, i.e. rotation, of each. In certain embodiments, ridges disposed in one or more lumens formed within Applicants' DIP fusion device releaseably mate with grooved portions formed in Applicants' delivery tool 700 and/or compressor tool 800.

In certain embodiments, a diameter of a lumen formed in anchor assembly 510, differs from a diameter of a lumen formed in compressor base assembly 520/525, and further differs from a diameter of a lumen formed in compressor sleeve assembly 530/535, and further differs from a diameter of a lumen formed in access port assembly 540. For example, in certain embodiments the diameter of an anchor assembly lumen is less than the diameter of a compressor assembly lumen. In certain embodiments, the delivery tool and/or the compressor tool is formed to comprise complementary diameter elements such that different portions of the delivery tool 700 and/or the compressor tool 800 can only be inserted to and releaseably mesh with the anchor assembly 510, or with the compressor base assembly 520/525, or with the compressor sleeve assembly 530/535, or with access port assembly 540. For example, in certain embodiments different portions of a delivery tool and/or a compressor tool can mesh with different asymmetrical groupings of ridges formed in an anchor assembly lumen, or in a compressor base lumen, or in the a compressor sleeve lumen, or in an access port lumen, to collectively or independently manipulate, i.e. rotate, one or more of those elements.

Referring now to FIGS. 4.4A, 4.4B, 4.5A, 4.5B, and 4.6, lumen 511A formed in anchor assembly 510 comprises a diameter 517. In certain embodiments, diameter 527 is between about 0.5 mm and about 2 mm, Lumen 511A is defined by wall 511B. In the illustrated embodiment of FIG. 4.6, an asymmetrical grouping of rounded ridges 519 is disposed longitudinally on wall 511B. Further in the illustrated embodiment of FIG. 4.6, seven rounded ridges 519 comprises an octagonal arrangement with a missing eighth ridge. The missing eighth rounded ridge in the otherwise octagonal pattern creates an asymmetry.

Referring now to FIGS. 4.4A, 4.4B, 4.5A, 4.5B, and 4.6, lumen 521A formed in compressor base assembly 520/525 comprises a diameter 527. In certain embodiments, diameter 517 equals diameter 527. In other embodiments, diameter 517 differs from diameter 527.

Lumen 521A is defined by wall 521B, In the illustrated embodiment of FIG. 4.6, an asymmetrical grouping of rounded ridges 529 is disposed longitudinally on wall 521B. Further in the illustrated embodiment of FIG. 4.6, seven rounded ridges 529 comprises an octagonal arrangement with a missing eighth ridge. The missing eighth rounded ridge in the otherwise octagonal pattern creates an asymmetry.

Referring now to FIGS. 4.4A, 4.4B, 4.5A, 4.5B, and 4.6, lumen 531A formed in compressor sleeve assembly 530/535 comprises a diameter 537. Lumen 531A is defined by wall 531B. In the illustrated embodiment of FIG. 4.6, an asymmetrical grouping of rounded ridges 539 is disposed longitudinally on wall 531B. Further in the illustrated embodiment of FIG. 4.6, seven rounded ridges 539 comprises an octagonal arrangement with a missing eighth ridge. The missing eighth rounded ridge in the otherwise octagonal pattern creates an asymmetry.

Referring now to FIGS. 4.4A and 4.6, lumen 541A formed in access port assembly 540 comprises a diameter 547. In certain embodiments, diameter 547 is between about 1.5 mm and about 4.5 mm.

Referring now to FIGS. 4.7 and 4.8, compressor base assembly 520/525 comprises attachment portion 620, and anchor assembly 510 comprises attachment portion 630. Attachment portion 630 comprises locking wedge 632, locking wedge 634, semi-circular platform 636, and semi-circular platform 638. In the illustrated embodiment of FIG. 4.7, locking wedge 632 and semi-circular platform 636 are disposed on one side of lumen 531A. Locking wedge 634 and semi-circular platform 638 are disposed on an opposite side of lumen 531A. Attachment portion 620 comprises locking wedge 622, locking wedge 624, semi-circular platform 626, and semi-circular platform 628.

Referring now to FIG. 4.9A, attachment portion 620 is formed to include annular groove 640. Annular groove 640 is defined in part by wall 642 and opposing wall 646. Wall 642 and wall 646 are not parallel. Rather, a distance 643 separates end 648 of wall 642 and the corresponding end 647 of wall 646. Line 644 is an extension of wall 642. A distance 641 separates end 645 of wall 646 from extension 644. Distance 641 is less than distance 643. As a result wall 646 inclines downwardly with respect to wall 642.

Locking wedge 622 comprises surface 662 and opposing surface 664. Surfaces 662 and 664 are not parallel. Rather, a distance 668 separates end 661 of surface 662 from end 665 of surface 664. Line 663 is an extension of surface 662. A distance 666 separates end 667 of surface 664 from extension 663. Distance 666 is less than distance 668. As a result, surface 664 of locking wedge 622 inclines with respect to surface 662.

Locking wedge 624 is formed and dimensioned in accord with the above-recited description of locking wedge 622. Therefore, both locking wedge 622 and locking wedge 624 comprise trapezoidal-shaped elements with inclining distal surfaces.

Attachment portion 630 is formed to include annular groove 650. Annular groove 650 is defined in part by wall 652 and opposing wall 656. Wall 652 and wall 656 are not parallel. Rather, a distance 653 separates end 658 of wall 652 and the corresponding end 657 of wall 656. Line 654 is an extension of wall 652. A distance 651 separates a end 655 of wall 656 from extension 654. Distance 651 is less than distance 653. As a result wall 656 inclines upwardly with respect to wall 652.

Locking wedge 634 comprises surface 672 and opposing surface 674. Surfaces 672 and 674 are not parallel. Rather, a distance 678 separates end 671 of surface 672 from end 677 of surface 674. Line 673 is an extension of surface 672. A distance 676 separates end 675 of surface 674 from extension 673. Distance 676 is less than distance 678. As a result, surface 674 of locking wedge 634 inclines with respect to surface 672.

Locking wedge 632 is formed and dimensioned in accord with the above-recited description of locking wedge 634. Therefore, both locking wedge 632 and locking wedge 634 comprise trapezoidal-shaped elements with inclining distal surfaces.

Distance 668 is less than distance 653, but greater than distance 651. Similarly, distance 678 is less than distance 643, but greater than distance 641.

FIG. 4.9B illustrates attachment portion 620 interconnected with attachment portion 630 in an unlocked configuration. Locking wedge 622 is rotatably disposed within annular groove 650 such that a gap 680 exists between wall 652 of annular groove 650 and surface 662 of locking wedge 622. Locking wedge 624 is similarly rotationally disposed within annular groove 650.

Locking wedge 634 is rotatably disposed within annular groove 640 such that a gap 690 exists between wall 646 of annular groove 640 and surface 674 of locking wedge 634. Locking wedge 632 is similarly rotationally disposed within annular groove 640.

When attachment portions 620 and 630 are interconnected as shown in FIG. 4.9B, anchor assembly 510 can be rotated in both a first direction and an opposing second direction with respect to compressor base assembly 520/525. FIG. 4.10 illustrates such a first rotation of anchor assembly 510 with respect to compressor base assembly 520/525. In the illustrated embodiment of FIG. 4.10, longitudinal axis 533 of anchor assembly 510 and longitudinal axis 527 of compressor base assembly 520/525 define an angle −Φ.

FIG. 4.11 illustrates rotation of anchor assembly 510 with respect to compressor base assembly 520/525 in a second direction. In the illustrated embodiment of FIG. 4.11, longitudinal axis 533 of anchor assembly 510 and longitudinal axis 527 of anchor assembly 510 define an angle +Φ.

In certain embodiments, angle Φ can vary between 0 degrees and 70 degrees. In certain embodiments and prior to insertion, anchor assembly 510 can be moved with respect to compressor base assembly 520/525 such that the angle Φ comprises a value of 0 to +/−70° off-axis rotation along one plane. Applicants' DIP fusion device 500/501 permits articulation of anchor assembly 510 with respect to compressor base assembly 520/525 in one plane only, that is, through a single plane of rotation. Anchor assembly 510 cannot rotate with respect to compressor base assembly 520/525 in the X/Z plane or in the Y/Z plane.

After insertion of DIP fusion device 500/501 into an intermediate phalanx and a distal phalanx, rotation of compressor base assembly 520/525 with respect to anchor assembly 510 is limited by hard tissues disposed adjacent to device 500/501. For example, in certain embodiments after insertion of device 500/501 into an intermediate phalanx and a distal phalanx compressor base assembly 520/525 can be rotated with respect to anchor assembly 510 about +/−30° off-axis in one plane.

FIG. 4.9C illustrates attachment portion 620 interconnected with attachment portion in a locked configuration. Referring now to FIGS. 4.9A and 4.9C, if tensile force 601 is exerted on the interconnected attachment portions 620 and 630, inclined surface 664 of locking wedge 622 slides upwardly along inclined wall 656 of annular groove 650. Because distance 668 is greater than distance 651, surface 664 of locking wedge 622 impacts wall 656 of annular groove 650, thereby forcing surface 662 of locking wedge 622 into wall 652 of annular groove 650, and thereby precluding rotation of attachment portion 620 with respect to attachment portion 630, and locking the configuration of attachment portions 620 and 630 in place. The tensile force 601 similarly jams inclined locking wedge 624 into annular groove 650 further locking the configuration of attachment portions 620 and 630 in place.

Similarly, if tensile force 601 is exerted on the interconnected attachment portions 620 and 630, inclined surface 674 of locking wedge 634 slides downwardly along inclined wall 646 of annular groove 640. Because distance 678 is greater than distance 641, surface 674 of locking wedge 634 impacts wall 646 of annular groove 640, thereby forcing surface 672 of locking wedge 634 into wall 642 of annular groove 640, and thereby precluding rotation of attachment portion 620 with respect to attachment portion 630, and locking the configuration of attachment portions 620 and 630 in place. The tensile force 601 similarly jams inclined locking wedge 632 into annular groove 640 further locking the configuration of attachment portions 620 and 630 in place.

In certain embodiments, surfaces 662 and 664 of locking wedge 622, the corresponding surfaces of locking wedge 634, surfaces 672 and 674 of locking wedge 634, the corresponding surfaces of locking wedge 632, the surfaces of walls 642 and 646 of annular groove 640, and the surfaces of walls 652 and 654 of annular groove 650, comprise a plurality of microscopic grooves and dimples formed using Electric Discharge Machining (EDM). In certain embodiments, surfaces 662 and 664 of locking wedge 622, the corresponding surfaces of locking wedge 634, surfaces 672 and 674 of locking wedge 634, the corresponding surfaces of locking wedge 632, the surfaces of walls 642 and 646 of annular groove 640, and the surfaces of walls 652 and 654 of annular groove 650, comprise a plurality of microscopic grooves and dimples formed using an abrasion process. In certain embodiments, surfaces 662 and 664 of locking wedge 622, the corresponding surfaces of locking wedge 634, surfaces 672 and 674 of locking wedge 634, the corresponding surfaces of locking wedge 632, the surfaces of walls 642 and 646 of annular groove 640, and the surfaces of walls 652 and 654 of annular groove 650, comprise a chemical or material coating disposed thereon.

When a tensile force is exerted on anchor assembly 510 and compressor base assembly 520/525, textured surfaces of locking wedges 622 and 624 impact textured walls of annular groove 650, and textured surfaces of locking wedges 632 and 634 impact textured walls of annular groove 640, and a high friction interlocking connection is created between the anchor assembly 510 and the compressor base assembly 520/525. In this manner, once the articulating linkage between anchor assembly 510 and compressor base assembly 520/525 is rotated to define a preferred configuration, that preferred configuration can be fixated by pulling the compressor base assembly 520/525 away from the anchor assembly 510 in tension. Placing compressor base assembly 520/525 and anchor assembly 510 in tension thereby secures or fixates Applicants' DIP fusion device 500/501 in a preferred configuration.

FIG. 5.1 illustrates Applicants' DIP fusion device 500 removeably disposed on Applicants' delivery tool 700. Delivery tool comprises handle 710, shaft 720, and loading portion 730. FIG. 5.2 shows a cross-section view of DIP fusion device 500 disposed on loading portion 730 of delivery tool 700. Referring now to FIGS. 5.2 and 5.3, loading portion 730 comprises a series of cylindrical elements having differing diameters. In the illustrated embodiment of FIGS. 5.2 and 5.3, loading portion 730 comprises tubular assemblies 740, 750, 760, and 770.

Tubular assembly 770 comprises a diameter 547. Interior lumen 541A formed in access port assembly 540 comprises a diameter 547. Therefore, tubular assembly 770 can be inserted into lumen 541A.

Tubular assembly 760 comprises a diameter 537 wherein diameter 537 is less than diameter 547. Interior lumen 531A formed in compressor sleeve assembly 530/535 comprises a diameter 537. Therefore, tubular assembly 760 can be inserted into lumen 541A and lumen 531A.

Tubular assembly 750 comprises a diameter 527 wherein diameter 527 is less than diameter 537. Interior lumen 521A formed in compressor base assembly 520/525 comprises a diameter 537. Therefore, tubular assembly 750 can be inserted into lumen 541A, lumen 531A, and lumen 521A.

Tubular assembly 740 comprises a diameter 517 wherein diameter 517 is less than diameter 527. Interior lumen 511A formed in anchor assembly 510 comprises a diameter 517. Therefore, tubular assembly 740 can be inserted into lumen 541A, lumen 531A, and lumen 521A, and lumen 511A.

Tubular assembly 760 is formed to include an asymmetrical pattern of grooves extending inwardly from an outer surface. A total of 7 grooves are formed in an octagonal arrangement with a missing eighth groove. The missing eighth groove in the otherwise octagonal pattern creates an asymmetry. The afore-described asymmetrical pattern of rounded ridges 539 formed in wall 531B defining lumen 531A disposed in compressor sleeve assembly 530/535 can mesh with the asymmetrical pattern of grooves formed in tubular assembly 760 if, and only if, the "missing" ridge of wall 531B is aligned with the "missing" groove of tubular assembly 760.

Tubular assembly 750 is formed to include an asymmetrical pattern of grooves extending inwardly from an outer surface. A total of 7 grooves are formed in an octagonal arrangement with a missing eighth groove. The missing eighth groove in the otherwise octagonal pattern creates an asymmetry. The afore-described asymmetrical pattern of rounded ridges 529 formed in wall 529B defining lumen 521A formed in compressor base assembly 520/525 can mesh with the asymmetrical pattern of grooves formed in tubular assembly 750 if, and only if, the "missing" ridge of wall 521B is aligned with the "missing" groove of tubular assembly 750.

Tubular assembly 740 is formed to include an asymmetrical pattern of grooves extending inwardly from an outer surface. A total of 7 grooves are formed in an octagonal arrangement with a missing eighth groove. The missing eighth groove in the otherwise octagonal pattern creates an asymmetry. The afore-described asymmetrical pattern of rounded ridges 519 formed in wall 519B defining lumen 511A formed in anchor assembly 510 can mesh with the asymmetrical pattern of grooves formed in tubular assembly 740 if, and only if, the "missing" ridge of wall 511B is aligned with the "missing" groove of tubular assembly 740.

In certain embodiments, delivery tool 700 is "clocked" or marked to indicate the orientation of the "missing" grooves. Using this indication, the plane of operation of the DIP fusion device 500 can be determined visually. Examples or markings or indicators of orientation can include: color markings on the delivery tool 700 and/or DIP fusion device 500, delivery tool handle 710 or delivery tool neck shape or texture, a lock-and-key fit between the out surface of the delivery tool 700 and the inner surface of the DIP fusion device 500, or a combination thereof.

FIG. 6.1 illustrates a compressor tool 800 with DIP fusion device 500 loaded thereon. In the illustrated embodiment of FIG. 6.1, compressor tool 800 comprises a compressor tool handle 810, a neck 820, and a loading region 830.

FIG. 6.2 shows a cross-section view of DIP fusion device 500 disposed on loading portion 830 of compression tool 800. Referring now to FIGS. 6.2 and 6.3, loading portion 830 comprises a series of cylindrical elements having differing diameters. In the illustrated embodiment of FIGS. 6.2 and 6.3, loading portion 830 comprises tubular assemblies 840 and 850.

Tubular assembly 850 comprises a diameter 547. Interior lumen 541A formed in access port assembly 540 comprises a diameter 547. Therefore, tubular assembly 850 can be inserted into lumen 541A.

Tubular assembly 840 comprises a diameter 537 wherein diameter 537 is less than diameter 547. Interior lumen 531A formed in compressor sleeve assembly 530/535 comprises a diameter 537. Therefore, tubular assembly 840 can be inserted into lumen 541A and lumen 531A.

Tubular assembly 840 is formed to include an asymmetrical pattern of grooves extending inwardly from an outer surface. A total of 7 grooves are formed in an octagonal arrangement with a missing eighth groove. The missing eighth groove in the otherwise octagonal pattern creates an asymmetry. The afore-described asymmetrical pattern of rounded ridges 539 formed in wall 531B defining lumen 531A formed in compressor sleeve assembly can mesh with the asymmetrical pattern of grooves formed in tubular assembly 840 if, and only if, the "missing" ridge of wall 531B is aligned with the "missing" groove of tubular assembly 840.

In certain embodiments, compression tool 800 is "clocked" or marked to indicate the orientation of the "missing" grooves. Using this indication, the plane of operation of the DIP fusion device 500 can be determined visually. Examples or markings or indicators of orientation can include: color markings on the compression tool 800 and/or DIP fusion device 500, compression tool handle 810 or compression tool neck shape or texture, a lock-and-key fit between the out surface of the compression tool 800 and the inner surface of the DIP fusion device 500, or a combination thereof.

In certain embodiments, the loading region 830 of the compressor tool 800 may be shorter than the loading region 730 of the delivery tool 700. For example, as shown in an enlarged cut away perspective of FIG. 6.2, the compressor tool 800 may be inserted into DIP fusion device 500 such that loading region 830 extends into the compressor sleeve assembly 530/535 and access port assembly 540 but does not extend into the anchor assembly 510 or the compressor base assembly 520/525. In this manner, the compressor tool 800 may be used to manipulate (e.g., rotate) the compressor sleeve assembly 530/535 independent of the anchor assembly 510 and/or the compressor base assembly 520/525.

FIGS. 7 through 11 illustrate the utility of Applicants' DIP fusion device 100 and 500/501. Referring to FIG. 7, DIP fusion device 100 or 500/501 is inserted into two adjacent bones, such as an intermediate phalanx 920 and a distal phalanx 910. The surfaces of the two adjacent bones are altered in preparation for fixation, such as by removal of cartilage and debris to facilitate bone-to-bone contact and shaped to facilitate angular fixation. For example, as shown in FIG. 7, the surfaces of the intermediate and distal phalanx have been shaped to facilitate a flexed fixation between the two adjacent bones 910 and 920.

The DIP fusion device 100 or 500/501 is advanced into the two adjacent bones using delivery tool 200 or 700, respectively. Using DIP fusion device 100, loading portion 330 of delivery tool 200 is inserted into DIP fusion device 100 such that a plurality of grooves formed in tubular assembly 336 portion of loading portion 330 mate with a plurality of rounded ridges 119 disposed on wall 111B of lumen 111A formed in anchor assembly 110, and such that a plurality of grooves formed in tubular assembly 334 portion of loading portion 330 mate with a plurality of ridges 129 disposed on wall 121B of lumen 121A formed in compressor assembly 120. Delivery tool is rotated clockwise to insert DIP fusion device 100 into bones 910 and 920.

Using DIP fusion device 500/501, loading portion 730 of delivery tool 700 is inserted into DIP fusion device 500/501 such that a plurality of grooves formed in tubular assembly 740 portion of loading portion 730 mate with a plurality of rounded ridges 519 disposed on wall 511B of lumen 511A formed in anchor assembly 110, and such that a plurality of grooves formed in tubular assembly portion 750 of loading portion 730 mate with a plurality of rounded ridges 529 disposed on wall 521B of lumen 521A formed in compressor base assembly 520/525, and such that a plurality of grooves formed in tubular assembly portion 760 of loading portion 730 mate with a plurality of rounded ridges 539 disposed on wall 531B of lumen 531A formed in compressor sleeve assembly 530/535. Delivery tool 300 or 700 is rotated clockwise to insert DIP fusion device 500 into bones 910 and 920.

Figure 8:
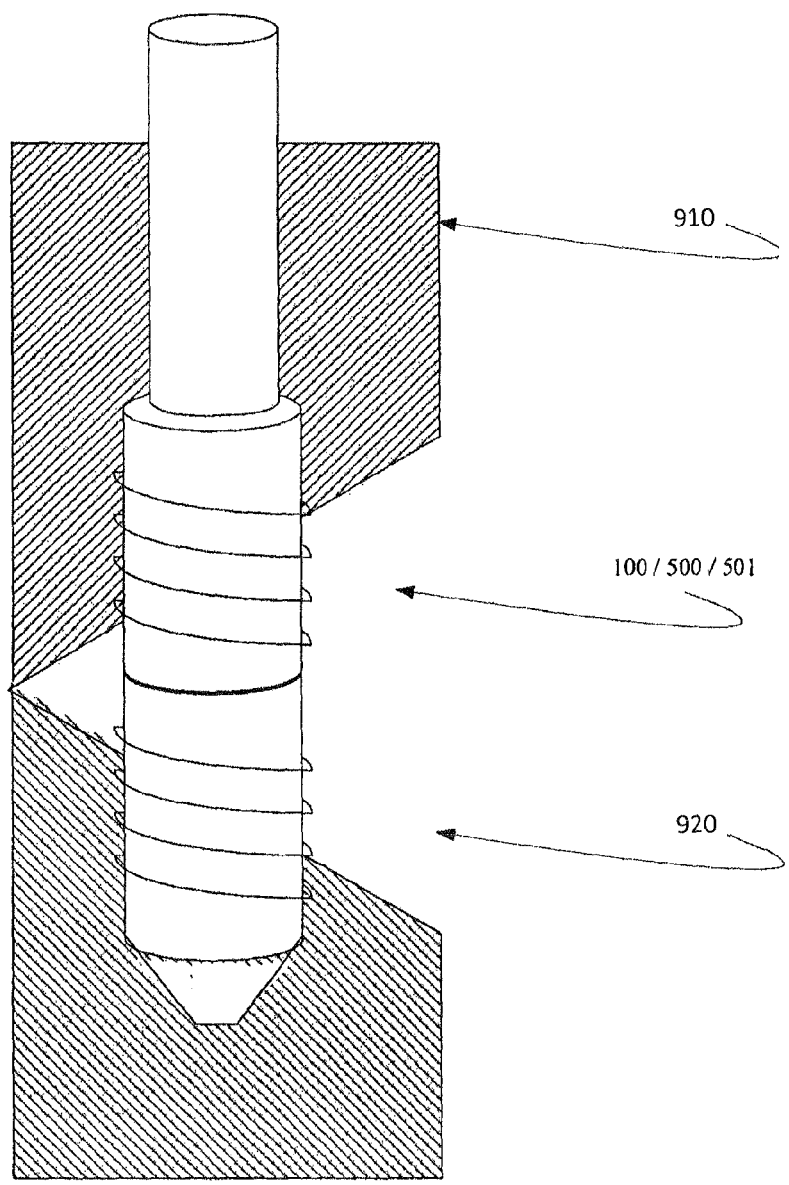
FIG. 8 illustrates Applicants' DIP fusion device inserted into a distal phalanx and a medial phalanx.

FIG. 8 illustrates DIP fusion device 100 or 500/501 disposed in bones 910 and 920 such that anchor assembly 110, or anchor assembly 510 in combination with compressor base assembly 520/525, is disposed in medial phalanx 920, and such that compressor assembly 120, or compressor sleeve assembly 530/535, is disposed in distal phalanx 910, and such that access port assembly 130 or 540 extends outwardly from distal phalanx 910. DIP fusion device 100 or 500/501 is positioned such that the articulating joint formed by anchor assembly 110 and compressor assembly 120, or the articulating joint formed by anchor assembly 510 in combination with compressor base assembly 520/525 and compressor sleeve assembly 530/535, is disposed in the joint separating phalanges 910 and 920.

Figure 9:
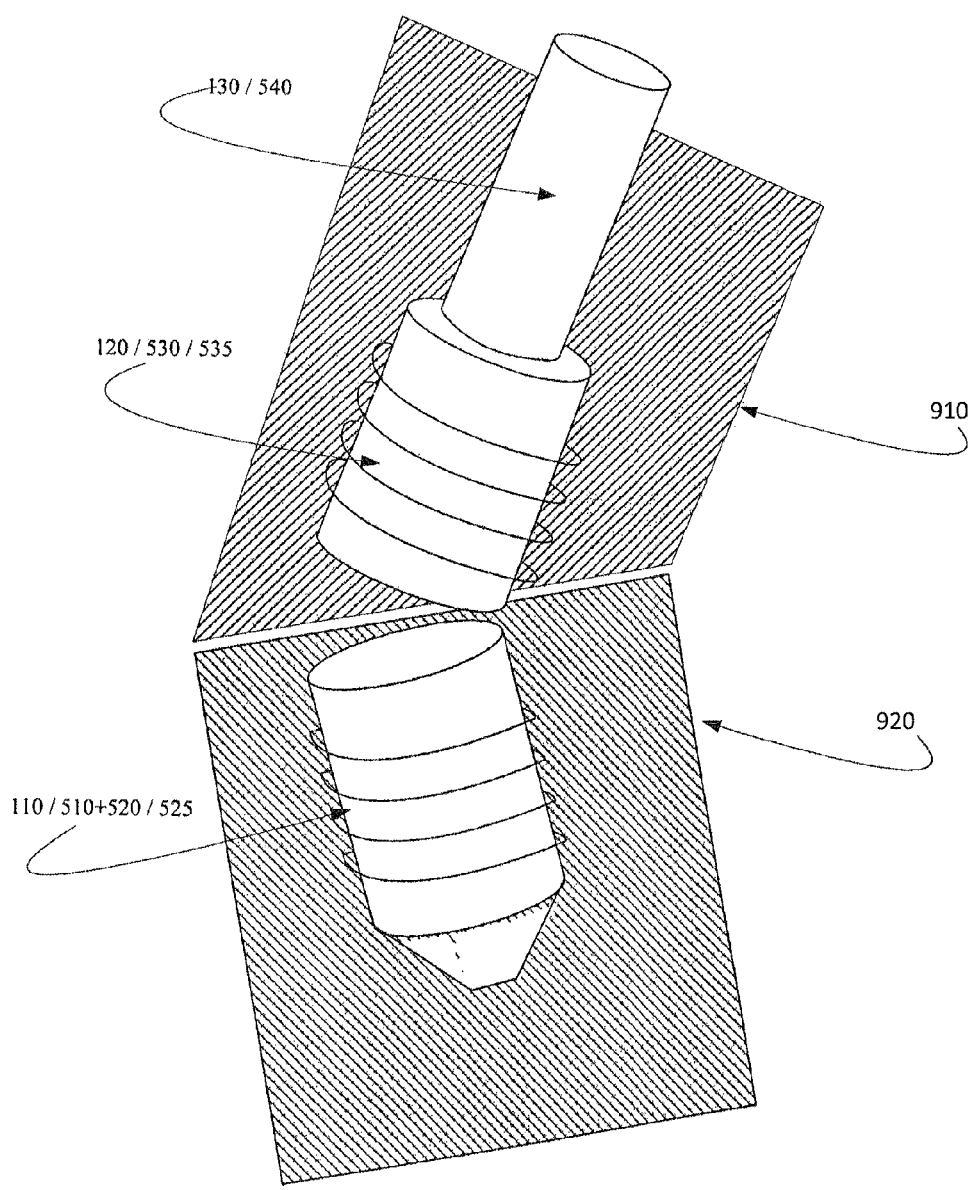
FIG. 9 illustrates the distal phalanx disposed in a flexed configuration with respect to the medial phalanx.

FIG. 9 illustrates distal phalanx 910 having been moved into a "flex" position with respect to medial phalanx 920. By moving distal phalanx 910 with respect to medial phalanx 920, compressor assembly 120 or compressor base assembly 520/525 is caused to articulate around the joint interconnecting compressor assembly 120 or compressor base assembly 520/525 and anchor assembly 110 or anchor assembly 510, respectively.

Figure 10:
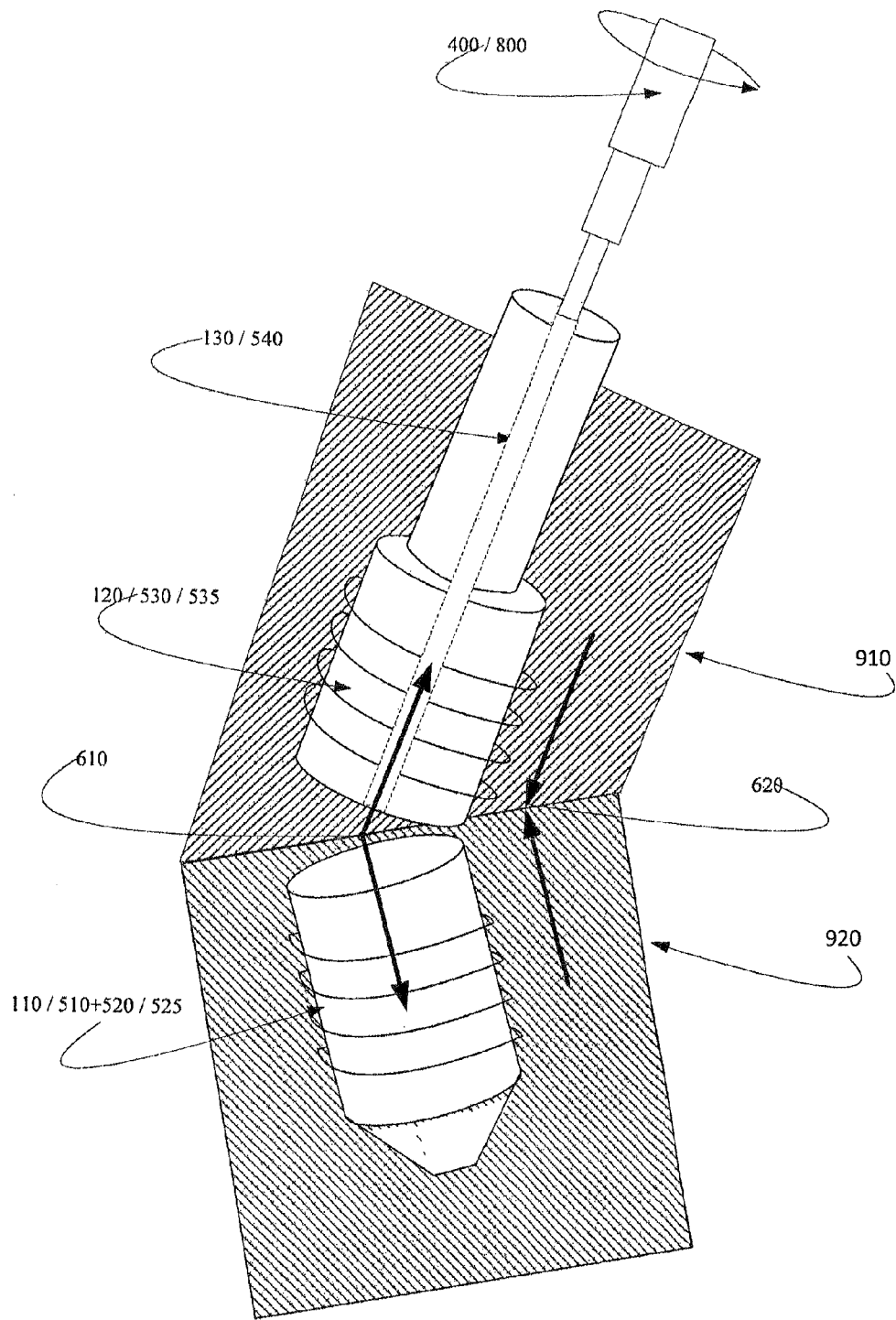
FIG. 10 illustrates Applicants' compressor tool being used to bring Applicants' inserted DIP fusion device into tension, and the distal phalanx and medial phalanx being brought into compression.

FIG. 10 illustrates compressor tool 400 or 800 inserted into compressor assembly 120 or compressor sleeve assembly 530/535, but not inserted into anchor assembly 110 or either anchor assembly 510 or compressor base assembly 520/525, respectively. When using DIP fusion device 100, loading portion 330 of compressor tool 400 is inserted into DIP fusion device 100 such that a plurality of ridges formed in tubular assembly portion 434 of loading portion 430 mate with a plurality of ridges 129 disposed on wall 121B of lumen 121 formed in compressor assembly 120. Compressor Tool 400 is rotated counter-clockwise to move compressor assembly 120 away from anchor assembly 110. Such movement of compressor assembly 120 away from anchor assembly 110 places Applicants' DIP fusion device 100 under tensile forces 610. In addition, such movement of compressor assembly 120 away from anchor assembly 110 places distal phalanx 910 and medial phalanx 920 in compression by compressive forces 620.

When using DIP fusion device 500/501, loading portion 830 of compressor tool 800 is inserted into DIP fusion device 500/501 such that a plurality of grooves formed in tubular assembly portion 760 of loading portion 730 mate with a plurality of rounded ridges 539 disposed on wall 531B of lumen 531A formed in compressor sleeve assembly 530/535. Compressor Tool 800 is rotated counter-clockwise to move compressor sleeve assembly 530/535 and compressor base assembly 520/525 move away from the Anchor Assembly 510. Such movement of compressor sleeve assembly 530/535 and compressor base assembly 520/525 move away from the Anchor Assembly 510 places Applicants' DIP fusion device 500/501 under tensile forces 610. In addition, such movement of/525 places distal phalanx 910 and medial phalanx 920 in compression by compressive forces 620.

Figure 11:
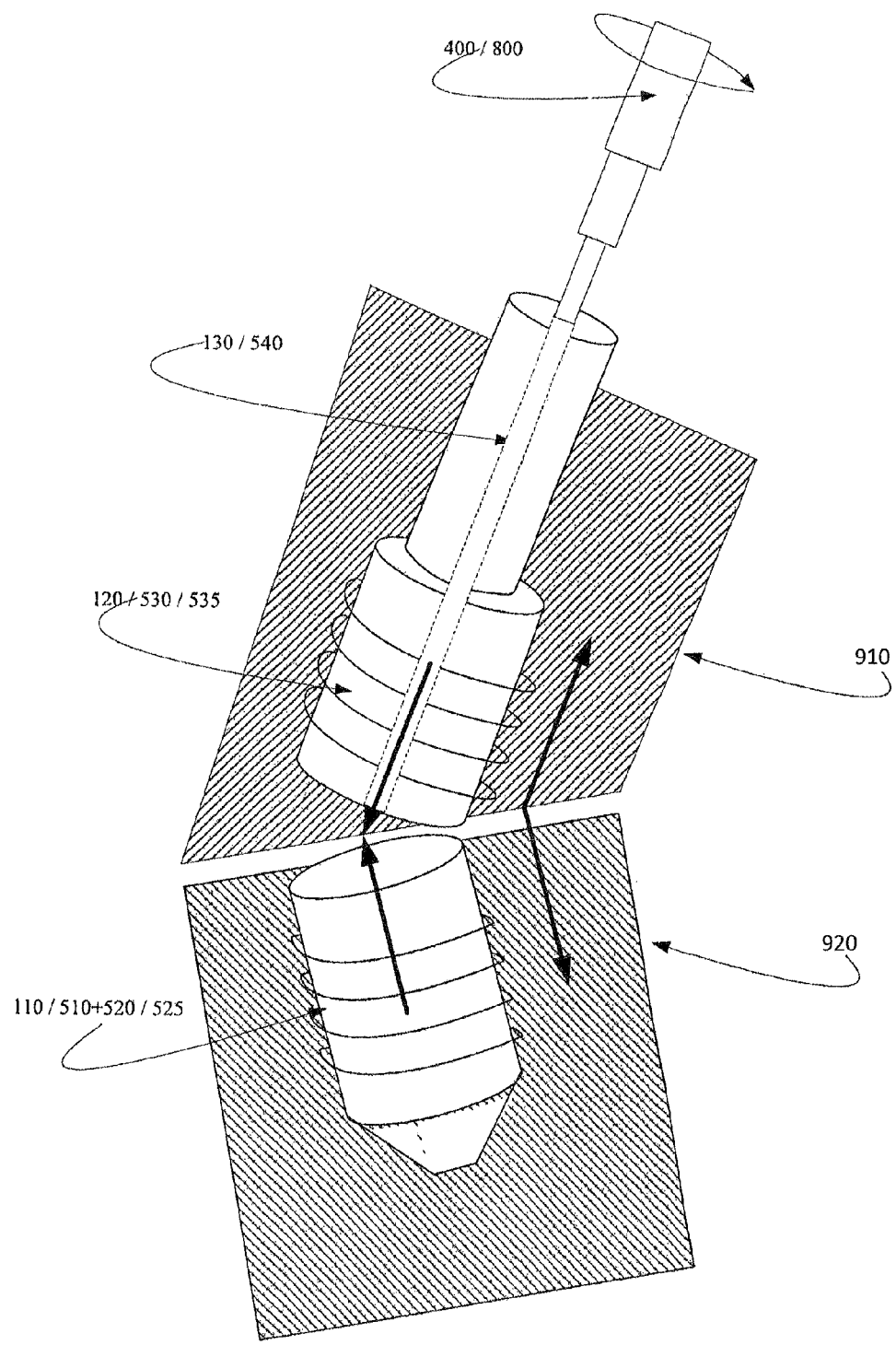
FIG. 11 illustrates Applicants' compressor tool being used to bring Applicants' inserted DIP fusion device out of tension, and the distal phalanx and medial phalanx being brought out of compression.

FIG. 11 illustrates compressor tool 400 or 800 inserted into compressor assembly 120 or compressor sleeve assembly 530/535, but not inserted into anchor assembly 110 or either anchor assembly 510 or compressor base assembly 520/525, respectively, as described hereinabove. When using DIP fusion device 100, loading portion 330 of compressor tool 400 is inserted into DIP fusion device 100 such that a plurality of ridges formed in tubular assembly portion 434 of loading portion 430 mate with a plurality of ridges 129 disposed on wall 121B of lumen 121A formed in compressor assembly 120. Delivery tool 300 is rotated clockwise to move compressor assembly 120 toward from anchor assembly 110. Such movement of compressor assembly 120 toward anchor assembly 110 removes Applicants' DIP fusion device 100 from the tensile forces of FIG. 10. In addition, such movement of compressor assembly 120 toward anchor assembly 110 removes distal phalanx 910 and medial phalanx 920 from compression.

When using DIP fusion device 500/501, loading portion 830 of compressor tool 800 is inserted into DIP fusion device 500/501 such that a plurality of grooves formed in tubular assembly portion 760 of loading portion 730 mate with a plurality of rounded ridges 539 disposed on wall 531B of lumen 531A formed in compressor sleeve assembly 530/535. If Compressor Tool 800 is rotated clockwise, then compressor sleeve assembly 530/535 moves toward compressor base assembly 520/525. Such movement of compressor sleeve assembly 530/535 and compressor base assembly 520/525 toward the Anchor Assembly 510 removes Applicants' DIP fusion device 500/501 from the tensile forces 610 of FIG. 10, In addition, such movement of compressor sleeve assembly 530/535 and compressor base assembly 520/525 toward the Anchor Assembly 510 removes distal phalanx 910 and medial phalanx 920 from compression.

Iterative rotation of Applicants' compressor tool in opposite directions as shown in FIGS. 10 and 11 may be used to bring distal phalanx 910 and medial phalanx 920 into and out of compression. Such iterative movement of the phalanges may be needed to adjust the orientation of distal phalanx 910 with respect to medial phalanx 920.

Figure 12:
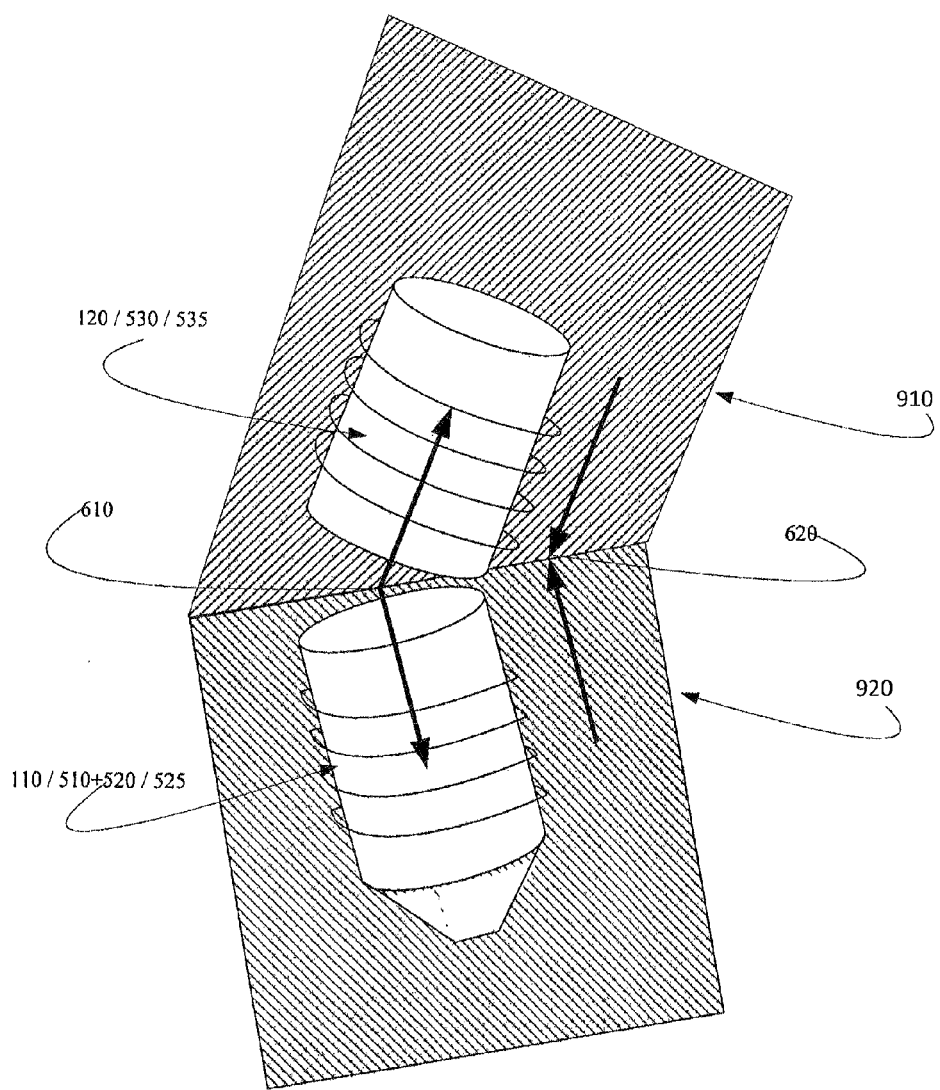
FIG. 12 shows Applicants' inserted DIP fusion device remaining in tension, and the distal phalanx and medial phalanx remaining in compression, after removal of an access port assembly portion of Applicants' DIP fusion device.

FIG. 12 shows access port assembly 130 or 540 having been removed from the inserted DIP fusion device 100, 500, 501. When using DIP fusion device 100, anchor assembly 110 remains disposed in medial phalanx 920, and compressor assembly 120 remains disposed in distal phalanx 920, such that distal phalanx 910 and medial phalanx 920 are held in compression with respect to one another.

When using DIP fusion device 500/501, anchor assembly 510 remains disposed in intermediate phalanx 920, and compressor sleeve assembly 530/535 in combination with compressor base assembly 520/525 remains disposed in distal phalanx 910, such that distal phalanx 910 and medial phalanx 920 are held in compression with respect to one another.

The embodiments of the invention also comprise kits that include one or more of the bone fusion apparatus of varying sizes and diameters to fit the application, delivery and compression tools, K-wires, drills and drill bits and a case for holding the tools and parts. Components of the kit may be sterile and/or sterilizable (e.g., autoclavable). In some examples, components of the kit, such as bone fusion apparatus and/or wires, may be intended for single use. In some examples, components of the kit, such as drills and/or drivers, may be intended or suitable for repeated use.

It will be understood that various modifications may be made to the embodiments disclosed herein. Therefore, the above description should not be construed as limiting, but merely as exemplifications of preferred embodiments. Those skilled in the art will envision other modifications that come within the scope and spirit of the claims appended hereto. All patents and references cited herein are explicitly incorporated by reference in their entirety.

We claim:

1. A bone fusion device comprising:
   an anchor assembly, the anchor assembly having a tubular cylindrical body at least a portion of which is covered by external threads adapted to engage hard tissue, the anchor assembly having a first end adapted to engage hard tissue and a second end adapted to rotationally couple with a compressor assembly;
   a compressor assembly, the compressor assembly having a tubular cylindrical body at least a portion of which is covered by external threads adapted to engage hard tissue, the compressor assembly having a first end adapted to rotationally couple with the anchor assembly and a second end having a lumen adapted to admit a tool, the external threads on both the anchor assembly and the compressor assembly having substantially the same pitch and diameter; and
   an articulating linkage for rotationally coupling the anchor assembly to the compressor assembly, wherein the articulating linkage comprises a locking feature such that the anchor assembly and the compressor assembly become locked in a fixed orientation when a tensile force is exerted on the anchor assembly and the compressor assembly after they are coupled, wherein the articulating linkage rotationally couples one end of the compressor assembly to the anchor assembly so that the compressor assembly may rotate about the anchor assembly within a semi-spherical zone, so as to have three degrees of rotational freedom, and translate axially, so as to have one degree of translational freedom, said device further comprising an access port assembly that threadably attaches to the second end of the compressor assembly.

2. The bone fusion device of claim 1 wherein the articulating linkage comprises a ball-and-socket joint.

3. The bone fusion device of claim 1 wherein the articulating linkage comprises a semi-spherical socket adapted to receive a semi-spherical ball.

4. The bone fusion device of claim 1 wherein the articulating linkage comprises a semi-spherical socket adapted to receive a semi-spherical ball, the socket located at the second end of the anchor assembly, and the compressor assembly having at its first end the semi-spherical ball.

5. The bone fusion device of claim 1 wherein the articulating linkage comprises a semi-spherical socket adapted to receive a semi-spherical ball, the socket located at the first end of the compressor assembly, and the anchor assembly having at its second end the semi-spherical ball.

6. The bone fusion device of claim 1, wherein the locking feature comprises textured surface elements on either or both of the anchor assembly and the compressor assembly.

7. The bone fusion device of claim 6, wherein the locking feature comprises a plurality of microscopic grooves and dimples located on either or both of the anchor assembly and the compressor assembly.

* * * * *